US012779089B2

(12) United States Patent
Si et al.

(10) Patent No.: US 12,779,089 B2
(45) **Date of Patent: *Nov. 3, 2026**

(54) BIOENGINEERED VASCULAR NETWORK

(71) Applicant: The Regents of the University of Michigan, Ann Arbor, MI (US)

(72) Inventors: Ming-Sing Si, Ann Arbor, MI (US); Josue Chery, Ann Arbor, MI (US); Shuyun Wang, Ann Arbor, MI (US)

(73) Assignee: The Regents of the university of Michigan, Ann Arbor, MI (US)

( * ) Notice: Subject to any disclaimer, the term of this patent is extended or adjusted under 35 U.S.C. 154(b) by 170 days.

This patent is subject to a terminal disclaimer.

(21) Appl. No.: 18/108,903

(22) Filed: Feb. 13, 2023

(65) Prior Publication Data

US 2024/0139378 A1 May 2, 2024

Related U.S. Application Data

(63) Continuation of application No. 16/466,735, filed as application No. PCT/US2017/064646 on Dec. 5, 2017, now Pat. No. 11,577,002.

(60) Provisional application No. 62/430,635, filed on Dec. 6, 2016.

(51) Int. Cl.

| | |
|---|---|
| ***A61L 27/50*** | (2006.01) |
| ***A61L 27/22*** | (2006.01) |
| ***A61L 27/38*** | (2006.01) |
| ***A61L 27/52*** | (2006.01) |
| ***C12M 1/00*** | (2006.01) |
| ***C12M 1/12*** | (2006.01) |
| ***C12M 3/00*** | (2006.01) |
| ***C12M 3/06*** | (2006.01) |

(52) U.S. Cl.

CPC ........... *A61L 27/507* (2013.01); *A61L 27/225* (2013.01); *A61L 27/3808* (2013.01); *A61L 27/3834* (2013.01); *A61L 27/3839* (2013.01); *A61L 27/3895* (2013.01); *A61L 27/52* (2013.01); *C12M 21/08* (2013.01); *C12M 23/16* (2013.01); *C12M 25/10* (2013.01); *C12M 29/10* (2013.01)

(58) Field of Classification Search

CPC .. A61L 27/507; A61L 27/225; A61L 27/3808; A61L 27/3834; A61L 27/3839; A61L 27/3895; A61L 27/52; C12M 21/08; C12M 23/16; C12M 25/10; C12M 29/10

See application file for complete search history.

(56) References Cited

U.S. PATENT DOCUMENTS

| | | | |
|---|---|---|---|
| 4,963,489 | A | 10/1990 | Naughton et al. |
| 5,559,022 | A | 9/1996 | Naughton et al. |
| 5,672,346 | A | 9/1997 | Srour et al. |
| 5,827,735 | A | 10/1998 | Young et al. |

FOREIGN PATENT DOCUMENTS

| | | |
|---|---|---|
| WO | WO 2008008229 A2 | 1/2008 |
| WO | WO 2014011775 A1 | 1/2014 |
| WO | WO 2018/106652 | 6/2018 |

OTHER PUBLICATIONS

Trkov S, Eng G, Di Liddo R, Parnigotto PP, Vunjak-Novakovic G. Micropatterned three-dimensional hydrogel system to study human endothelial-mesenchymal stem cell interactions. 2010; J Tissue Eng Regen Med. 4(3):205-215. doi:10.1002/term.231 (Year: 2010).*

Akhtar et al., "Characterizing the elastic properties of tissues" Materials Today 2011; 14(3):96-105.

Alexander et al., "Epigenetic Control of Smooth Muscle Cell Differentiation and Phenotypic Switching in Vascular Development and Disease" Annual Review of Physiology. 2012; 74:13-40.

Bae, H. et al. Building vascular networks. Science translational medicine 2012; 4(160):23.

Bettex et al., "Is our heart a well-designed pump? The heart along animal evolution" European heart journal 2014; 35(34):2322-2332.

Bersini et al., "Cell-microenvironment interactions and architectures in microvascular systems" Biotechnology Advances. 2016; 34(6):1113-1130.

Blum et al., "Complex cell rearrangements during intersegmental vessel sprouting and vessel fusion in the zebrafish embryo" Developmental Biology. 2008; 316(2):312-322.

Bonifacino et al., "Current Protocols in Cell Biology" John Wiley & Sons. 2000 TOC.

Brinkmann et al., "VE-cadherin interacts with cell polarity protein Pals1 to regulate vascular lumen formation" Molecular Biology of the Cell. 2016; 27(18):2811-2821.

Caplan et al., "Body Management: Mesenchymal Stem Cells Control the Internal Regenerator" Stem Cells Translational Medicine. 2015; 4:695-701.

Chaki et al., "Integration of signaling and cytoskeletal remodeling by Nck in directional cell migration" BioArchitecture. 2013; 3:57-63.

Crisan et al., "A Perivascular Origin for Mesenchymal Stem Cells in Multiple Human Organs" Cell Stem Cell. 2008; 3:301-313.

Datta et al., "Bioprinting for vascular and vascularized tissue biofabrication" Acta Biomaterialia. 2017; 51:1-20.

Davis et al., "An alpha 2 beta 1 integrin-dependent pinocytic mechanism involving intracellular vacuole formation and coalescence regulates capillary lumen and tube formation in three-dimensional collagen matrix." Experimental cell research, 1996; 224:39-51.

Del Toro et al., "Identification and functional analysis of endothelial tip cell-enriched genes" Blood. 2010; 116:4025-4033.

Demou et al., "Microgenomics profile the endogenous angiogenic phenotype in subpopulations of aggressive Melanoma" Journal of Cellular Biochemistry. 2008; 105(2):562-573.

(Continued)

*Primary Examiner* — Maria G Leavitt
*Assistant Examiner* — Kodye Lee Abbott
(74) *Attorney, Agent, or Firm* — Thomas A. Isenbarger

(57) ABSTRACT

Provided herein is technology relating to engineered tissues and particularly, but not exclusively, to methods, compositions, and systems for engineering a biosynthetic vascular network.

11 Claims, 36 Drawing Sheets

(56) References Cited

OTHER PUBLICATIONS

De Smet et al., "Mechanisms of Vessel Branching Filopodia on Endothelial Tip Cells Lead the Way" Arteriosclerosis, Thrombosis, and Vascular Biology. 2009; 29:639-649.
D'Uva et al., "Beta-Catenin/HuR Post-Transcriptional Machinery Governs Cancer Stem Cell Features in Response to Hypoxia" PLOS ONE 2013; 8(11): e80742.
Eilken et al., "Dynamics of endothelial cell behavior in sprouting angiogenesis" Current Opinion in Cell Biology. 2010; 22(5):617-625.
Evrard et al., "Endothelial to mesenchymal transition is common in atherosclerotic lesions and is associated with plaque instability" Nature Communications. 2016; 7:11853.
Fantin et al., "Tissue macrophages act as cellular chaperones for vascular anastomosis downstream of VEGF-mediated endothelial tip cell induction" Blood. 2010; 116:829-840.
Ferri et al., "Effect of S(-) perillic acid on protein prenylation and arterial smooth muscle cell proliferation" Biochemical Pharmacology. 2001; 62(12):1637-1645.
Friis et al., "Comparison of mesenchymal stromal cells from young healthy donors and patients with severe chronic coronary artery disease" Scandinavian Journal of Clinical and Laboratory Investigation. 2011; 71:193-202.
Gang et al., "In vitro endothelial potential of human UC blood-derived mesenchymal stem cells" Cytotherapy. 2006; 8:215-227.
Gao et al., "4D Bioprinting for Biomedical Applications" Trends in Biotechnology. 2016; 34:746-756.
Gauvin et al., "Microscale Technologies and Modular Approaches for Tissue Engineering: Moving toward the Fabrication of Complex Functional Structures" ACS Nano 2011; 5:4258-4264.
Ghabrial et al., "Social interactions among epithelial cells during tracheal branching morphogenesis" Nature. 2006; 441:746-749.
Glenny et al., "Emergence of matched airway and vascular trees from fractal rules" Journal of applied physiology. 2010; 110:1119-1129.
Gokcinar-Yagci et al., "Pericytes: Properties, Functions and Applications in Tissue Engineering". Stem cell reviews and reports, 2015 11(4), 549-559.
Grant et al., "The Role of Basement Membranes in Vascular Development" Annals of the New York Academy of Sciences. 1990; 588:61-72.
Grant et al., "Regulation of Capillary Formation by Laminin and other Components of the Extracellular Matrix" Regulation of Angiogenesis. 1997; 79:317-333.
Grassl et al., Fibrin as an alternative biopolymer to type-I collagen for the fabrication of a media equivalent. *Journal of biomedical materials research*, 2002, 60(4), 607-612.
Grikscheit et al., "Formins at the Junction" Trends in Biochemical Sciences. 2016; 41:148-159.
Hendrix et al., "Tumor cell vascular mimicry: Novel targeting opportunity in melanoma" Pharmacology & Therapeutics. 2016; 159:83-92.
Herbert et al., "Molecular control of endothelial cell behaviour during blood vessel morphogenesis" Nat Rev Mol Cell Biol 2011; 12:551-564.
Herwig et al., "Distinct Cellular Mechanisms of Blood Vessel Fusion in the Zebrafish Embryo" Current Biology. 2011; 21:1942-1948.
Heydarkhan-Hagvall et al., "Human Adipose Stem Cells: A Potential Cell Source for Cardiovascular Tissue Engineering" Cells Tissues Organs. 2008; 187(4):263-274.
Ho et al., "Increased Survival and Function of Mesenchymal Stem Cell Spheroids Entrapped in Instructive Alginate Hydrogels" Stem Cells Translational Medicine. 2016; 5(6):773-781.
Hofer et al., "Secreted trophic factors of mesenchymal stem cells support neurovascular and musculoskeletal therapies" Stem Cell Research & Therapy. 2016; 7:131.
Horowitz et al., "Branching morphogenesis." Circ Res 2008; 103:784-795.
International Search Report and Written Opinion PCT/US2017/064646, dated May 28, 2018, 21 pages.
Jackson et al., "Hematopoietic potential of stem cells isolated from murine skeletal muscle" PNAS. 1999; 96(25):14482-14486.
Jockenhoevel et al., "Fibrin gel—advantages of a new scaffold in cardiovascular tissue engineering" European Journal of Cardio-Thoracic Surgery. 2001; 19(4):424-430.
Kolesky et al., "Three-dimensional bioprinting of thick vascularized tissues" PNAS. 2016; 113:3179-3184.
Koo et al., "Rasip1 is essential to blood vessel stability and angiogenic blood vessel growth" Angiogenesis. 2016; 19:173-190.
Lampugnani et al., "CCM1 regulates vascular-lumen organization by inducing endothelial polarity" Journal of Cell Science. 2010; 123:1073-1080.
Laschke et al., "Prevascularization in tissue engineering: Current concepts and future directions." Biotechnology advances 2016; 34(2):112-121.
Lee et al., "Spherical Bullet Formation via E-cadherin Promotes Therapeutic Potency of Mesenchymal Stem Cells Derived From Human Umbilical Cord Blood for Myocardial Infarction" Molecular Therapy. 2012; 20(7):1424-1433.
Lee et al., "Creating perfused functional vascular channels using 3D bio-printing technology" Biomaterials. 2014; 35:8092-8102.
Lenard et al., "In vivo analysis reveals a highly stereotypic morphogenetic pathway of vascular anastomosis". Developmental cell, 2013 25(5), 492-506.
Li et al., "4D bioprinting: the next-generation technology for biofabrication enabled by stimuli-responsive materials" Biofabrication. 2016; 9:012001.
Lu et al., "Snail mediates PDGF-BB-induced invasion of rat bone marrow mesenchymal stem cells in 3D collagen and chick chorioallantoic membrane" J. Cell. Physiology. 2013; 228:1827-1833.
Maniotis et al., "Vascular Channel Formation by Human Melanoma Cells in Vivo and in Vitro: Vasculogenic Mimicry" The American Journal of Pathology. 1999; 155(3):739-752.
Masters, ed., "Animal Cell Culture" Oxford University Press. 2000.
Mazzone et al., "Heterozygous Deficiency of PHD2 Restores Tumor Oxygenation and Inhibits Metastasis via Endothelial Normalization" Cell. 2009; 136:839-851.
Melchiorri et al., "Mesenchymal Stem Cells: Roles and Relationships in Vascularization" Tissue Engineering Part B Reviews. 2014; 20:218-228.
Miao et al., "Escargot controls the sequential specification of two tracheal tip cell types by suppressing FGF signaling in *Drosophila*" Development. 2016; 143:4261-4271.
Miguelino et al., "Abstract 134: Adipose Derived Stem Cells Express von Willebrand Factor and Factor VIII" Plastic and Reconstructive Surgery. 2014; 133:150.
Miller, J. S. et al. "Rapid casting of patterned vascular networks for perfusable engineered three-dimensional tissues." Nature materials 2012; 11:768-774.
Monahan-Earley et al., "Evolutionary origins of the blood vascular system and endothelium." Journal of thrombosis and haemostasis 2013; 11(1):46-66.
Nehls et al., "Pericyte involvement in capillary sprouting during angiogenesis in situ" Cell and Tissue Research. 1992; 270(3):469-474.
Norotte et al., "Scaffold-free vascular tissue engineering using bioprinting" Biomaterials. 2009; 30:5910-5917.
Ozerdem et al., "Early Contribution of Pericytes to Angiogenic Sprouting and Tube Formation" Angiogenesis. 2003; 6(3):241-249.
Phng et al., "Formin-Mediated Actin Polymerization at Endothelial Junctions Is Required for Vessel Lumen Formation and Stabilization" Developmental Cell. 2015; 32(1):123-132.
Pittenger et al., "Multilineage Potential of Adult Human Mesenchymal Stem Cells" Science. 1999; 284:143-147.
Prockop et al., "Marrow stromal cells as stem cells for nonhematopoietic tissues" Science. 1997 276(5309), 71-74.
Ridley et al., "Rho GTPase signalling in cell migration" Current Opinion in Cell Biology. 2015; 36:103-112.
Rizvi et al., "Identification and Characterization of a Small Molecule Inhibitor of Formin-Mediated Actin Assembly" Chemistry & Biology. 2009; 16:1158-1168.

(56) References Cited

OTHER PUBLICATIONS

Rouwkema et al., "Vascularization and Angiogenesis in Tissue Engineering: Beyond Creating Static Networks" Trends in Biotechnology. 2016; 34:733-745.
Shi et al., "Perivascular Niche of Postnatal Mesenchymal Stem Cells in Human Bone Marrow and Dental Pulp" Journal of Bone and Mineral Research. 2003; 18(4):696-704.
Siemerink et al., "CD34 marks angiogenic tip cells in human vascular endothelial cell cultures" Angiogenesis. 2012; 15(1):151-163.
Simons et al., "Molecular Controls of Arterial Morphogenesis" Circulation research, 2015; 116:1712-1724.
Skoog et al., "Stereolithography in tissue engineering" Journal of Materials Science: Materials in Medicine. 2014; 25(3):845-856.
Theise et al., "Derivation of hepatocytes from bone marrow cells in mice after radiation-induced myeloablation" Hepatology. 2000; 31:235-240.
Tung et al., "Tips, Stalks, Tubes: Notch-Mediated Cell Fate Determination and Mechanisms of Tubulogenesis during Angiogenesis" Cold Spring Harbor perspectives in medicine. 2012; 2: a006601.
Turksen ed., "Embryonic Stem Cells: Methods and Protocols" Humana Press. 2002.
Wagenblast et al., "A model of breast cancer heterogeneity reveals vascular mimicry as a driver of metastasis" Nature. 2015; 520:358-362.
Wang et al., "Mesenchymal Stem/Stromal Cells from Discarded Neonatal Sternal Tissue: In Vitro Characterization and Angiogenic Properties" Stem Cells International. 2016; 5098747, 10 page.
Weissman et al., "Stem and Progenitor Cells: Origins, Phenotypes, Lineage Commitments, and Transdifferentiations", Annual Review of Cell and Developmental Biology. 2001; 17:387-403.
Wang. et al. "Characterization and angiogenic potential of human neonatal and infant thymus mesenchymal stromal cells" Stem cells translational medicine, 2015; 4, 339-350.
Welch-Reardon et al., "Angiogenic sprouting is regulated by endothelial cell expression of Slug" Journal of Cell Science. 2014; 127:2017-2028.
Yang et al., "Slug, mammalian homologue gene of *Drosophila escargot*, promotes neuronal-differentiation through suppression of HEB/daughterless" Cell Cycle. 2010; 9:2789-2802.
Ye et al., "Fibrin gel as a three dimensional matrix in cardiovascular tissue engineering" European Journal of Cardio-Thoracic Surgery. 2000; 17(5):587-591.
Zotin et al., "Thermodynamic aspects of developmental biology." Journal of theoretical biology. 1967; 17:57-75.
Zuk et al., "Multilineage Cells from Human Adipose Tissue: Implications for Cell-Based Therapies" Tissue Engineering 2001; 7:211-228.
Trkov et al. Micropatterned three-dimensional hydrogel system to study human endothelial-mesenchymal stem cell interactions. J Tissue Eng and Reg Med. 2010; 4, 205-215.

* cited by examiner

FIG. 11A
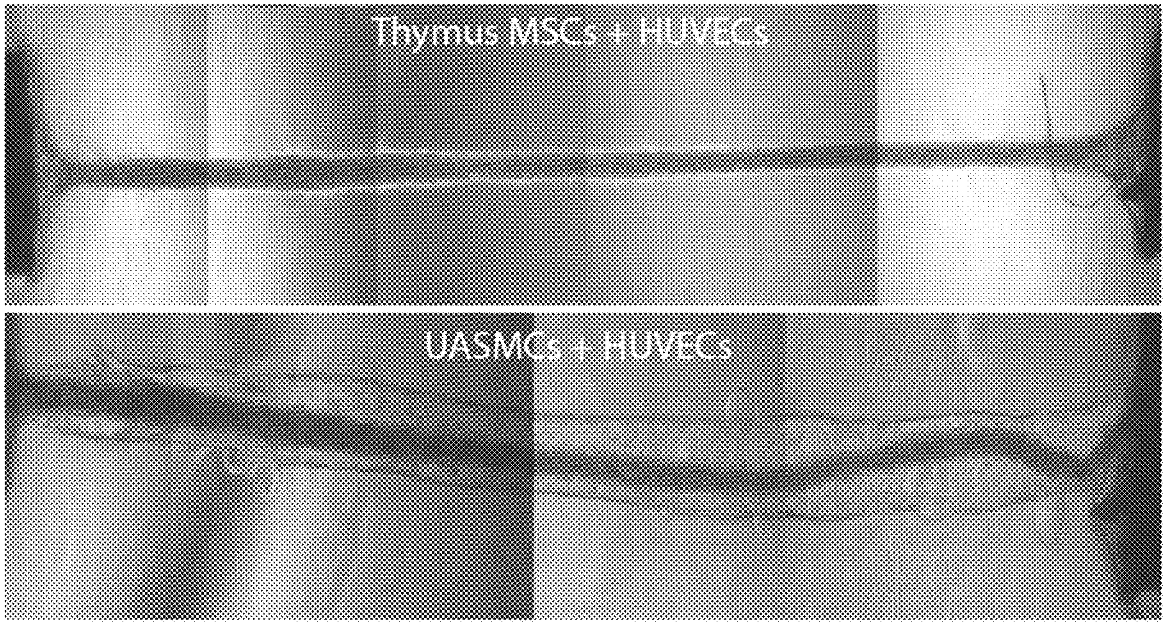
FIG. 11B
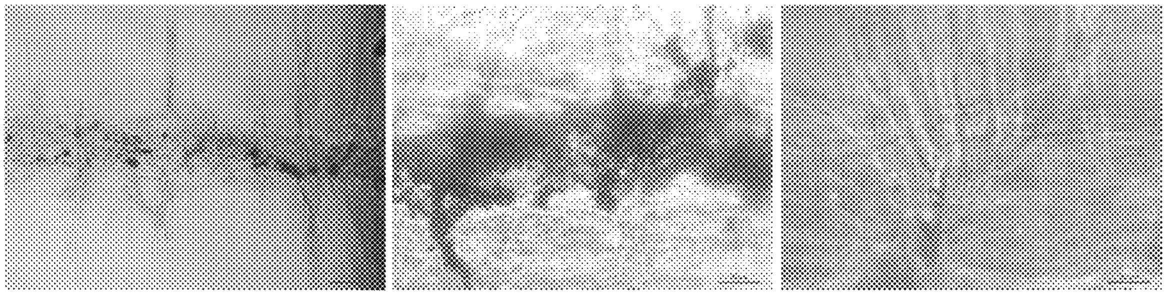
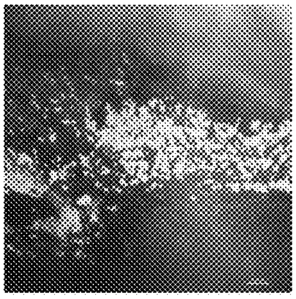
FIG. 11C

FIG. 13A
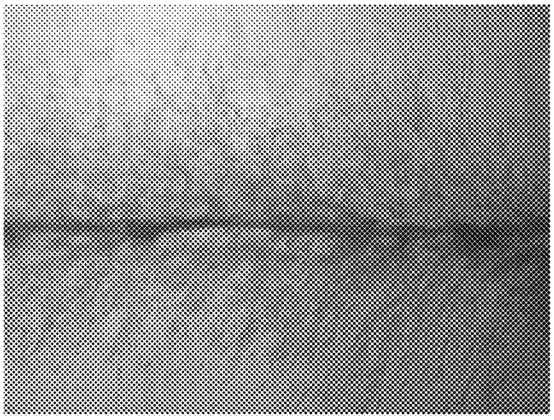
FIG. 13B
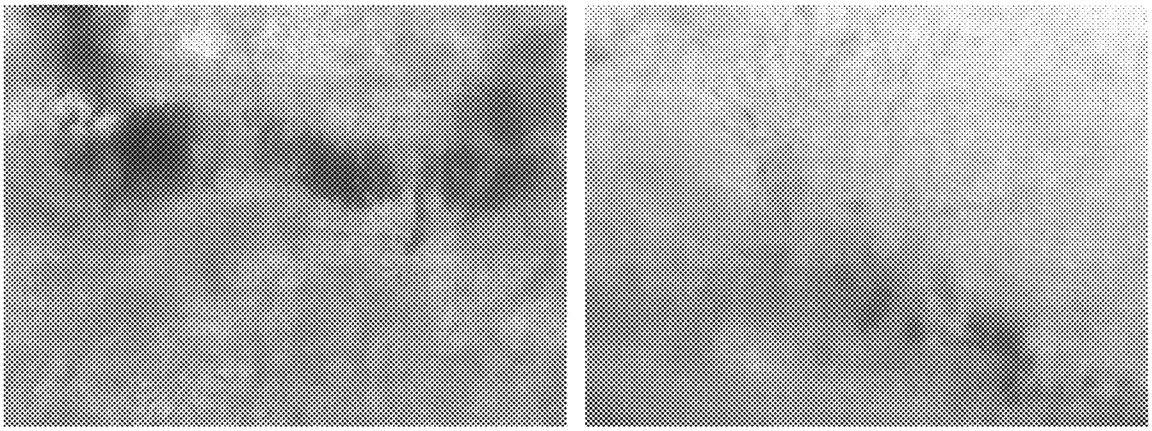
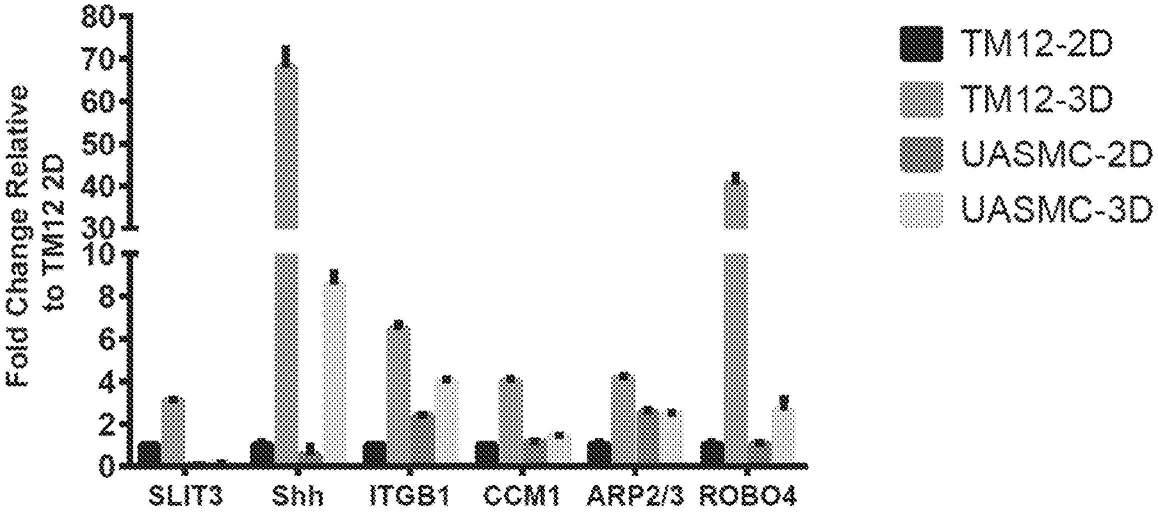
FIG. 13C

Top view

Oblique view

BIOENGINEERED VASCULAR NETWORK

This application is a continuation of U.S. patent application Ser. No. 16/466,735, filed Jun. 5, 2019, now U.S. Pat. No. 11,577,002, issued Feb. 14, 2023, which is a national phase application under 35 U.S.C. § 371 of PCT International Application No.: PCT/US2017/064646, filed on Dec. 5, 2017, which claims the benefit of U.S. provisional patent application Ser. No. 62/430,635, filed Dec. 6, 2016, each of which is incorporated herein by reference in its entirety.

STATEMENT REGARDING FEDERALLY SPONSORED RESEARCH OR DEVELOPMENT

Field

Provided herein is technology relating to engineered tissues and particularly, but not exclusively, to methods, compositions, and systems for engineering a biosynthetic vascular network.

Background

Engineered tissues have the potential to replace their deficient or diseased native counterparts, thus conceivably curing end-stage disease of multiple organs. The effectiveness of many treatments using engineered tissue is related to providing an engineered tissue having a sufficient thickness to provide a meaningful clinical effect. Providing a tissue having the appropriate dimensions (e.g., thickness) for clinical use depends on providing sufficient vascularization and perfusion to the engineered tissue prior to implantation, which is a critical technical problem that impedes the engineering of several types of thick organ and/or tissue replacement parts (see, e.g., 1,2). Current vascularization strategies are insufficient for thick tissues because they are based on a classical paradigm of angiogenesis: establishing angiogenic sprouting using endothelial cells (ECs); and promoting and stabilizing vascular networks using adjacently placed mural cells, such as mesenchymal stem cells (MSCs), pericytes, and smooth muscle cells (SMCs) (see, e.g., 5-7). Using such extant technologies, previous attempts to engineer a vasculature having sufficient scale and function to support thick engineered tissues have been inadequate. Without sufficient vasculature, engineered tissues are limited to thin scales such as those found in organisms that survive without a circulatory system or with a simple, open circulatory system (e.g., jellyfish and arthropods). Improved bioengineered vascularization technologies are needed to advance bioengineered tissue therapies for humans and other organisms.

SUMMARY

Accordingly, provided herein are technologies related to an engineered (e.g., in vitro) vasculature sufficient to provide a functional vascular network to thick engineered tissues. In some embodiments, the technology described herein is based on the development of an in vitro vasculogenic phenomena that is a clear departure from extant technologies based on tip EC-led sprouting that underpins the basis of the classical angiogenesis paradigm. In particular, experiments conducted during the development of embodiments of the technology provided herein indicated that mural cells are present in spherical organoids comprising mesenchymal stem cells (MSCs) with and without ECs. Data collected from these experiments guided the development of the technology to generate a perfuseable, complete, and functional vascular network emanating from a macroscopic cylindrical organoid.

In some embodiments, the technology provides an engineered vasculature for engineered tissues that is multiscalar (e.g., macroscale to microscale) and multiphenotype (e.g., comprises arterial, microvascular, and/or venous components). Such a multiscale, multiphenotype engineered vasculature technology finds use, e.g., to distribute energy and mass flow to parenchymal cells.

In some embodiments, the engineered vasculature technology has dimensions and functions similar to the dimensions and functions of a native vasculature (e.g., in the terminal vascular bed), e.g., to provide a mass transport function for the engineered tissue supported by the vasculature. For example, in some embodiments the engineered vascular network provides one or more of, e.g., a perfused artery (e.g., having a dimension of at least 1 mm), one or more arterioles (e.g., having a dimension of at least 10-200 μm), one or more capillaries (e.g., having a dimension of at least 4-10 μm), one or more venules (e.g., having a dimension of at least 10-200 μm), and/or a draining vein (e.g., having a dimension of at least 1 mm). In some embodiments, the artery and vein have a diameter on the millimeter scale (e.g., at least approximately 1 to 10 mm), e.g., to provide surgical anastomosis to a patient vascular network and to accommodate a perfusate flow rate that adequately supports thick engineered tissues. In some embodiments, the intervening capillary network is complex, dense, and responds to the dynamic needs of the parenchyma.

Accordingly, provided herein is technology related to a method for producing an engineered vasculature, the method comprising forming an organoid comprising endothelial cells (ECs) and mesenchymal stem cells (MSCs) embedded in a hydrogel. In some embodiments, the ratio of ECs to MSCs is approximately 1 to 1. In some embodiments, embodiments the ratio of ECs to MSCs ranges from 0.5 to 1 to 1 to 0.5. Some embodiments comprise forming an organoid of ECs, MSCs, and smooth muscle cells (SMCs). As discussed herein, the technology comprises use of a hydrogel for the culture (e.g., three-dimensional culture) of cells. In some embodiments, the hydrogel comprises fibrin. In some embodiments, the ECs are vein endothelial cells; in some embodiments, the ECs are artery endothelial cells. In some embodiments, the MSCs are derived from stem cells (e.g., pluripotent stem cells, induced pluripotent stem cells, etc.). In some embodiments, the ECs are derived from stem cells (e.g., pluripotent stem cells, induced pluripotent stem cells, etc.). In some embodiments, the MSCs are derived from the thymus, bone, or adipose tissue. In some embodiments, forming the organoid comprises providing a mixture of ECs and MSCs into a hydrogel channel. In some embodiments, the methods comprise incubating the organoid at physiological conditions, e.g., at 37° C. and/or 5% $CO_2$. The technology produces angiogenic sprouting when the ECs and MSCs are mixed and present in a hydrogel at a high density. For example, in some embodiments the ECs and MSCs are present at a density of at least approximately 40 million cells per cubic centimeter. In some embodiments, the cells are provided at a density of, e.g., 10 to 100 million cells per cubic centimeter (e.g., 10, 15, 20, 25, 30, 35, 40, 45, 50, 55, 60, 65, 70, 75, 80, 85, 90, 95, or 100 or more cells per cubic centimeter).

Further embodiments provide a method for producing an engineered vasculature (e.g., comprising an artery and a vein), the method comprising forming a first organoid comprising artery endothelial cells (ECs) and mesenchymal stem cells (MSCs) embedded in a hydrogel; and forming a second organoid comprising vein endothelial cells (ECs) and mesenchymal stem cells (MSCs) embedded in a hydrogel. Embodiments provide that sprouts from the first and second organoids meet and anastomose. Accordingly, some embodiments provide that the first and second organoids are placed in appropriate proximity with each other to provide for the anastomosis of sprouts from the first and second organoids. For example, in some embodiments the methods comprise placing the first organoid approximately 1 mm from the second organoid. In some embodiments the methods comprise placing the first organoid approximately 0.1 to 5 mm (e.g., 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mm) from the second organoid. Thus, in some embodiments arterioles sprouting from the first organoid anastomose with venules sprouting from the second organoid. That is, in some embodiments the methods comprise locating the first organoid relative to the second organoid and providing conditions appropriate for the formation of a capillary bed between the first organoid and the second organoid.

Related embodiments provide a perfusable engineered vasculature comprising patent macroscale vessels and patent microscale vessels. In some embodiments, the perfusable engineered vasculature comprises an engineered artery and an engineered arteriole. In some embodiments, the perfusable engineered vasculature comprises an engineered vein and an engineered venule. In some embodiments, the perfusable engineered vasculature comprises an engineered artery, an engineered arteriole, an engineered capillary bed, an engineered venule, and engineered vessels having a diameter of approximately 4 mm or greater and comprises vessels having a diameter of approximately 10 to 200 μm in diameter. In some embodiments, the perfusable engineered vasculature comprises vessels having a diameter of approximately 4 to 10 μm. In some embodiments, the perfusable engineered vasculature comprises endothelial cells (ECs) and mesenchymal stem cells (MSCs) embedded in a hydrogel. In some embodiments, the perfusable engineered vasculature comprises fibrin. In some embodiments, the ECs are vein endothelial cells. In some embodiments, the ECs are human artery endothelial cells. In some embodiments, the MSCs are derived from thymus, bone, adipose, or other cells or tissues. In some embodiments, the ECs and/or MSCs are derived from stem cells (e.g., pluripotent stem cells, induced pluripotent stem cells, etc.)

Some embodiments provide a device for producing a perfusable engineered vasculature, the device comprising a tissue chamber comprising a channel for producing an organoid comprising endothelial cells (ECs) and mesenchymal stem cells (MSCs) embedded in a hydrogel. In some embodiments, the device comprises a channel that is approximately greater than 1, 2, 3, 4, or 5 mm in diameter. In some embodiments, the device comprises an inlet port for perfusion of the perfusable engineered vasculature and an outlet port for draining of the perfusable engineered vasculature. Various embodiments of the device are made from a polymer, e.g., a biocompatible polymer as described herein. In some embodiments, the device is made of polydimethylysiloxane. In some embodiments, the channel of the device comprises a fibrin hydrogel. And, in some embodiments the channel comprises an organoid comprising endothelial cells (ECs) and mesenchymal stem cells (MSCs) embedded in a hydrogel.

In related embodiments, the technology provides a device for producing a perfusable engineered vasculature, the device comprising a tissue chamber comprising a first channel for producing an organoid comprising artery endothelial cells (ECs) and mesenchymal stem cells (MSCs) embedded in a hydrogel and a second channel for producing an organoid comprising vein endothelial cells (ECs) and mesenchymal stem cells (MSCs). In some embodiments, the device further comprises a medium between the first channel and the second channel wherein arterioles sprouting from the first organoid anastomose with venules sprouting from the second organoid to form a capillary bed.

The technology finds use in the preparation of engineered tissues, organs, and biological systems (e.g., comprising multiple tissues and/or organs). For example, embodiments of the technology provide an engineered vascularized organ tissue comprising organ parenchymal cells and a perfusable engineered vasculature comprising patent macroscale vessels and patent microscale vessels. In some embodiments, the engineered organ tissue is a thick tissue, e.g., a tissue that is thicker than what oxygen diffusion can support. In some embodiments, the engineered organ tissue is more than approximately 0.4 mm thick and in some embodiments the engineered organ tissue is more than approximately 0.8 mm thick. In some embodiments, the engineered organ tissue is more than 0.4, 0.45, 0.5, 0.55, 0.6, 0.65, 0.7, 0.75, or 0.8 mm thick. In some embodiments, the engineered organ tissue comprises a perfusable engineered vasculature comprising an engineered artery and an engineered arteriole. In some embodiments, the engineered organ tissue comprises a perfusable engineered vasculature comprising an engineered vein and an engineered venule. In some embodiments, the engineered organ tissue comprises a perfusable engineered vasculature comprising an engineered artery, an engineered arteriole, an engineered capillary bed, an engineered venule, and an engineered vein. In some embodiments, the engineered organ tissue comprises a perfusable engineered vasculature comprising vessels having a diameter of approximately 4 mm or greater and comprising vessels having a diameter of approximately 10 to 200 μm in diameter. In some embodiments, the engineered organ tissue comprises a perfusable engineered vasculature comprising vessels having a diameter of approximately 4 to 10 μm.

The technology further comprises embodiments of systems. For example, in some embodiments the technology provides a system for producing a perfusable engineered vasculature, the system comprising, e.g., a tissue chamber comprising a channel for producing an organoid; a hydrogel; and a mixture of endothelial cells (ECs) and mesenchymal stem cells (MSCs). In some embodiments, the cells used in the system (e.g., the ECs) are artery ECs and/or vein ECs. In some embodiments, the MSCs are derived from thymus, bone, or adipose or other tissue or cells. In some embodiments, the cells are stem cells (e.g., pluripotent stem cells, induced pluripotent stem cells). In some embodiments, the system comprises an incubator to promote production of sprouts from an organoid comprising a mixture of ECs and MSCs embedded in a hydrogel. In some embodiments, the system comprises components for producing a hydrogel, e.g., fibrinogen and thrombin for producing a fibrin hydrogel. Embodiments of the system comprise a tissue chamber made from a polymer, e.g., a biocompatible polymer, e.g., polydimethylsiloxane.

Embodiments provide kits, e.g., kits for producing a perfusable engineered vasculature. In some embodiments, a kit comprises a tissue chamber comprising a channel for producing an organoid; and components for producing a hydrogel. Some kit embodiments comprise fibrinogen and thrombin for producing a fibrin hydrogel. In some embodiments, the tissue chamber of the kit is made from polydimethylsiloxane.

Embodiments of the technology find use in medical therapy, clinical use, research use, and in commercial use. In some embodiments, the technology relates to use of a perfusable engineered vasculature to produce an engineered vascularized organ tissue. In some embodiments, the technology relates to drug development and testing. In some embodiments, the technology relates to use of a perfusable engineered vasculature for in vivo therapeutic angiogenesis, e.g., use of a perfusable engineered vasculature to treat ischemia.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 41) shows flow cytometry data from experiments indicating that MSCs do not comprise a subpopulation of ECs. The MSCs were tested for the presence of the classical EC markers CD31 and vonWillebrand’s factor (vWF). The data indicated that the MSC preparations lacked CD31 expression (and thus did not comprise ECs) while vWF expression was more significant at 10%, which is consistent with previous reports indicating that vWF expression is found at baseline or upon stimulation with VEGFA in MSCs from various tissues.

FIG. 5A shows that control spherical organoids comprising MSCs transfected with scramble siRNA and ECs transfected with scramble siRNA manifested brisk sprouting at 24 hours. FIG. 5B shows that spherical organoids comprising MSCs transfected with scramble siRNA and ECs transfected with Rac siRNA had decreased sprouting. FIG. 5C shows that spherical organoids comprising MSCs transfected with Rac siRNA and ECs transfected with scramble siRNA demonstrated essentially no sprouting. Collectively, these results indicate that MSCs lead and promote sprouting from MSC+EC spherical organoids.

FIG. 1013 shows dye tracking studies indicating that vascular networks produced by SMC+EC cylindrical organoids were led by and comprised SMCs.

FIG. 11A shows microscope images indicating that the main channels of the cylindrical organoids comprising a combination of MSCs and ECs are patent. Patency of the channels was indicated by observing the passage of saline through the outlet port after injecting saline into the inlet ports at day 3, 7, and 14. The data indicated that MSC containing cylindrical organoids were patent: however, constructs comprising SMCs were not. In particular, cylindrical organoids comprising a combination of umbilical artery (UA) SMCs and ECs were uniformly not patent and forced perfusion of these constructs resulted in fluid flowing around the solid cord of cells (FIG. 11A).

FIG. 11B shows microscope images indicating that the main channel (engineered vessel) and the emanating vascular network comprise patent vessels. In particular, cylindrical organoids were perfused with microspheres and observed. The observations indicated the patency of the main vessel and its branches.

FIG. 11C shows a fluorescence photomicrograph indicating that the main channel (engineered vessel) and the emanating vascular network comprise patent vessels.

FIG. 13A is a microscope image indicating that formin activity is not central to the sprouting response in MSC+EC cylindrical organoids.

FIG. 13B is a series of microscope images indicating that lumen formation in engineered vascular networks was not dependent on formin activity. In particular, microbeads passed through SMIFH2-treated MSC+EC engineered vascular networks, indicating patency of the vessels in the presence of SMIFH2, which inhibits formin activity.

FIG. 13C is a bar plot showing that MSCs (e.g., UASMCs and thymus MSCs) in 2D and spherical organoid form possessed higher expression of genes associated with lumen formation when cultured in three dimensions relative to two dimensions.

FIG. 26 is a schematic drawing showing an embodiment of the technology provided herein related to 4D bioprinting.

Figure 1:
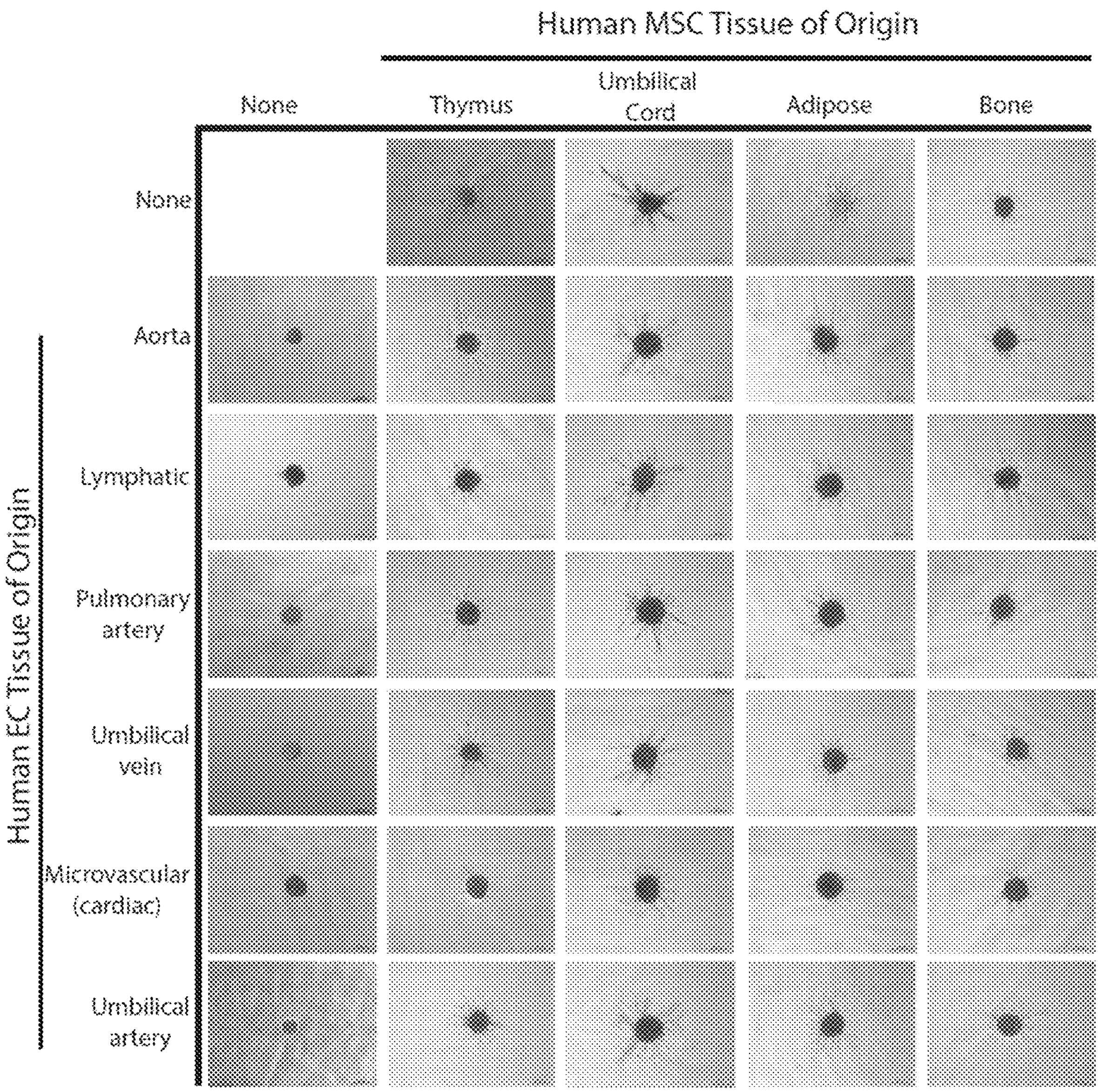
FIG. 1 is a series of photographs showing sprouting and tubulogenesis of endothelial cells (first column) and mesenchymal stem cells (first row). ECs from aorta, lymphatic, pulmonary artery, umbilical vein, cardiac microvasculature, and umbilical artery were cultured as spherical organoids and embedded in fibrin gel. MSCs from thymus, umbilical cord, adipose, and bone were cultured as spherical organoids and embedded in fibrin gel. When cultured in spherical organoids and embedded in fibrin gel, human MSCs from various tissue sources consistently manifested tubulogenic behavior. Spherical organoids made of human ECs from various tissue sources also generated tubules, but at much lesser degree and rate as compared to those comprised of MSCs. Addition of ECs to MSCs produced greater sprouting and tubulogenesis than MSCs alone (columns 2-5).

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology relating to engineered tissues and particularly, but not exclusively, to methods, compositions, and systems for engineering a biosynthetic vascular network.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

The present technology can be implemented and utilized in numerous ways, including without limitation as a process, an apparatus, a system, a device, a kit (e.g., a kit comprising one of the platforms described herein and, in some embodiments, instructions for use), a method for applications now known and later developed or a computer readable medium. These and other unique features of the technology disclosed herein will become more readily apparent from the following description and the accompanying drawings.

DEFINITIONS

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "approximately" or "about", when referring to a value or to an amount of mass, weight, time, volume, concentration, or percentage is meant to encompass variations of, in some embodiments, ±20%; in some embodiments, ±10%; in some embodiments, ±5%; in some embodiments, ±1%; in some embodiments, ±0.5%; and, in some embodiments; ±0.1% from the specified amount, as such variations are appropriate to perform the disclosed method. As used herein, ranges can be expressed as from "approximately" or "about" one particular value, and/or to "approximately" or "about" another particular value. It is also understood that there are a number of values disclosed herein, and that each value is also herein disclosed as "approximately" or "about" that particular value in addition to the value itself. For example, if the value "10" is disclosed, then "approximately 10" is also disclosed. It is also understood that each unit between two particular units are also disclosed. For example, if 10 and 15 are disclosed, then 11, 12, 13, and 14 are also disclosed.

As used herein, "EC" is an abbreviation for "endothelial cell"; "MSCs" is an abbreviation for "mesenchymal stem cells"; "SMCs" is an abbreviation for "smooth muscle cells"; "HUAEC" is an abbreviation for "human umbilical arterial endothelial cell"; "HMVEC" is an abbreviation for "human microvascular endothelial cell"; "HUVEC" is an abbreviation for "human umbilical vein endothelial cell"; "HUASMC" is an abbreviation for "human umbilical artery smooth muscle cells"; "ECM" is an abbreviation for "extracellular matrix"; "VMC" is an abbreviation for "vascular mural cell"; and "MMPs" is an abbreviation for "matrix metalloproteinases".

The term "endothelial cells" (EC) refers to a cell of endothelial origin including mature or semi-mature or partially-mature population of endothelial cells isolated from different tissues and organs, endothelial progenitor cells (EPC), endothelial colony forming cells (ECFC), circulating and fixed endothelial cells, endothelial cells isolated from cord blood, peripheral blood, adult blood, blood vessels, clonally propagated endothelial and endothelial progenitor cells, low and high proliferating potential ECFC and those that are differentiated from a progenitor cell such as a from a stem cell.

Mural cells (e.g., vascular mural cells) include vascular smooth muscle cells and pericytes, both of which are involved in the formation of normal vasculature. These cells are responsive to vascular endothelial growth factor (VEGF). According to a model of angiogenesis, neovascularization is a multicellular process comprising the participation of ECs and VMCs, such as pericytes, mesenchymal stem cells (MSCs), and vascular smooth muscle cells (SMCs). During angiogenesis, tip ECs lead sprouting with stalk ECs in tow and phalanx ECs remaining quiescent. Vascular mural cells are then recruited to the abluminal surface of nascent sprouts to stabilize them by promoting the deposition of basement membrane.

Endothelial cells (ECs) are those cells that cover the interior or luminal surface of blood vessels. ECs that find use in the present technology include, without limitation, arterial and venous ECs such as human coronary artery endothelial cells (HCAEC), human aortic endothelial cells (HAAEC), human pulmonary artery endothelial cells (HPAEC), dermal microvascular endothelial cells (DMEC), human umbilical vein endothelial cells (HUVEC), human umbilical artery endothelial cells (HUAEC), human saphenous vein endothelial cells (HSVEC), human jugular vein endothelial cells (HJVEC), human radial artery endothelial cells (HRAEC), and human internal mammary artery endothelial cells (HIMAEC). Useful ECs can also be obtained from circulating endothelial cells and endothelial cell precursors such as bone marrow progenitor cells, peripheral blood stem cells and embryonic stem cells.

Smooth muscle cells encircle the endothelial cells in a vessel and regulate the vessel's diameter by expanding and contracting. Smooth muscle cells that find use in the technology provided herein include, without limitation, human aortic smooth muscle cells (HAMC), human umbilical artery smooth muscle cells (HUASMC), human pulmonary artery smooth muscle cells (HPASMC), human coronary artery smooth muscle cells (HCASMC), human bronchial smooth muscle cells (HBSMC), human radial artery smooth muscle cells (HRASMC), and human saphenous or jugular vein smooth muscle cells.

With respect to stem cells that are utilized in accordance with embodiments of methods provided herein, as used herein, the term "stem cells" refers broadly to traditional stem cells, progenitor cells, preprogenitor cells, precursor cells, reserve cells, and the like. Exemplary stem cells include, but are not limited to, embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including methods for isolating and culturing them, may be found in, among other places, Embryonic Stem Cells, Methods and Protocols, Turksen, ed., Humana Press, 2002; Weisman et al., Annu Rev. Cell. Dev. Biol. 17:387-403; Pittinger et al., Science, 284:143-47, 1999; Animal Cell Culture, Masters, ed., Oxford University Press, 2000; Jackson et al., PNAS 96(25): 14482-86, 1999; Zuk et al., Tissue Engineering, 7:211-228, 2001; and U.S. Pat. Nos. 5,559,022, 5,672,346 and 5,827,735. Descriptions of stromal cells, including methods for isolating them, may be found in, among other places, Prockop, Science, 276:71-74, 1997; Theise et al., Hepatology, 31:235-40, 2000; Current Protocols in Cell Biology, Bonifacino et al., eds., John Wiley & Sons, 2000; and U.S. Pat. No. 4,963,489. One of ordinary skill in the art will understand that the stem cells and/or stromal cells that are selected for inclusion in a tissue construct are typically selected when such cells are appropriate for the intended use of a particular construct.

As used herein, a "thick tissue" refers to any tissue that is thicker than what oxygen diffusion can support. In most cases oxygen can typically diffuse into a tissue to a depth of approximately 0.2 to 0.4 mm. So, for a planar construct of tissue that can obtain oxygen from all surfaces, the maximum thickness for a tissue that is not thick (a "thin tissue") is 0.4 to 0.8 mm. Accordingly, in some embodiments a "thick tissue" is more than approximately 0.4 mm thick and in some embodiments more than approximately 0.8 mm thick (e.g., more than 0.4, 0.45, 0.5, 0.55, 0.6, 0.65, 0.7, 0.75, or 0.8 mm thick).

As used herein, a "high cell density" is approximately 40 million cells per cubic centimeter, e.g., in some embodiments, 10 million to 100 million cells per cubic centimeter (e.g., in some embodiments 10, 20, 30, 40, 50, 60, 70, 80, 90, or 100 million cells per cubic centimeter).

As used herein, the term "scale" refers to the relative and/or absolute size. The term "microscale" refers to a size that is microscopic, e.g., a "microscale" object or thing is not typically able to be visualized by an unaided human eye. A "microscale" object or thing may have features or components that are not distinguishable by an unaided human eye. Accordingly, "microscale" objects or things are detectable and have features distinguishable when viewed under a microscope, e.g., at 2× to 100× (e.g., 2×, 2.5×, 5×, 10×, 20×, 25×, 50×, 100×, etc.) or more magnification. The term "macroscale" refers to a size that is not microscopic (e.g., a size that is "macroscopic"), e.g., a "macroscale" object or thing is typically able to be visualized by an unaided human eye. A "macroscale" object or thing may have features or components that are distinguishable by an unaided human eye. Accordingly, "macroscale" objects or things are detectable and have features distinguishable when viewed by an unaided human eye. The range of sizes that are "microscale" and "macroscale" may overlap and no firm cutoff value is provided that distinguishes "microscale" and "macroscale". An approximate, typical size cutoff for the "microscale" and "macroscale" range is 1 mm. That is, objects, things, features that are approximately 1 mm or smaller are generally considered to be "microscale" and objects, things, features that are approximately 1 mm or larger are generally considered to be "macroscale".

The replication of physiological design principles in vascular networks is referred to herein by the phrase "engineered vascular networks".

The subject technology described herein includes the theory, concepts, design, manufacturing, testing and applications of engineered vascular networks. In some embodiments, these vascular networks find use in producing tissue engineered structures such as an organ or other tissue. There are additional applications of this technology, for example, as a tool, e.g., a platform for drug discovery, development, and/or evaluation (e.g., toxicity, safety and/or efficacy); and as a platform for in vitro or in vivo research and testing.

As used herein, the term "biomaterial" refers to any material suitable for use in a biological application. Examples of suitable biomaterials may include, but are not limited to, polydimethylsiloxane (PDMS), polyamides, poly (siloxanes), poly(silicones), poly(ethylene), poly(vinyl pyrrolidone), poly(-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol) (PEG) hydrogels, poly(methacrylic acid), poly(lactic acid) (PLA), poly(glycolic acid) (PGA), poly(lactide-co-glycolides) (PLGA), polyanhydrides, and polyorthoesters poly(carbonate), poly(acrylo nitrile), poly(ethylene oxide), polyaniline, polyvinyl carbazole, polystyrene and poly(vinyl phenol), polyhydroxyacids, poly(caprolactone), polyanhydrides, polyhydroxyalkanoates, polyurethanes, polysaccharides and poly-biologics such as collagen, albumin, alginate, chitosan, starch, and hyaluronic acid, gelatin, agarose, fibrin, MATRIGEL, glycerol, glycol, and sugar-alcohols, such as mannitol, inositol, xylitol, and adonitol, amino acids such as glycine and arginine, biological polymeric molecules and particularly proteins such as albumin, peptide amphiphiles, and monomers, dimers, and/or oligomers of said materials. As will be recognized by one of ordinary skill in the art, the biomaterial selected will depend on, inter alia, the given application and specifications required. In some embodiments, biomaterials suitable for use in the present disclosure may be crosslinked.

Additionally, the biomaterial or biomaterials can optionally contain pharmaceuticals, proteins, DNA, nanoparticles, or other moieties used for drug delivery applications and/or sensing or combinations of these to enhance or stimulate biological behaviors such as proliferation, differentiation, migration, matrix deposition, or support the formation of more physiologic tissue.

The term "monolayer" as used herein can refer to cells that are attached to a solid support while proliferating in suitable culture conditions. A small portion of cells proliferating in a monolayer under suitable growth conditions may be attached to cells in the monolayer but not to the solid support. Preferably less than 15% of these cells are not attached to the solid support, more preferably less than 10% of these cells are not attached to the solid support, and most preferably less than 5% of these cells are not attached to the solid support.

The term "plated" or "plating" or "seeding" as used herein in reference to cells can refer to establishing cell cultures in vitro. For example, cells can be diluted in cell culture media and then added to a cell culture plate, dish, flask, or device as described herein (tissue chamber). Cell culture plates are commonly known to a person of ordinary skill in the art. Cells may be plated at a variety of concentrations and/or cell densities.

As used herein, the term "vasculogenesis" refers to the de novo formation of new blood vessels. The term "vasculogenic potential" refers to the ability of cells to form blood vessels or blood vessel-like vascular network in vitro.

As used herein, the term "angiogenesis" refers to the process by which new blood vessels are generated from existing vasculature and tissue. The phrase "repair or remodeling" refers to the reformation of existing vasculature. As used herein, the term "angiogenic factor" or "angiogenic protein" refers to any known protein capable of promoting growth of new blood vessels from existing vasculature ("angiogenesis").

As used herein, the term "arteriogenesis" refers to the process of enhancing growth of collateral arteries and/or other arteries from pre-existing arteriolar connections.

The term "suspension" is used herein to refer to a composition comprising biologically-relevant materials, including magnetic particles, cells, tissues, proteins, and the like that are dispersed within a biocompatible medium. A suitable biocompatible medium for use in accordance with the presently-disclosed subject matter can typically be formed from any biocompatible material that is a gel, a semi-solid, or a liquid, such as a low-viscosity liquid, at room temperature (e.g., 25° C.) and can be used as a three-dimensional substrate for cells, tissues, proteins, and other biological materials of interest. Exemplary materials that can be used to form a biocompatible medium in accordance with the presently-disclosed subject matter include, but are not limited to, polymers and hydrogels comprising collagen, fibrin, chitosan, MATRIGEL (BD Biosciences, San Jose, Calif.), polyethylene glycol, dextrans including chemically crosslinkable or photo-crosslinkable dextrans, and the like, as well as electrospun biological, synthetic, or biological-synthetic blends. In some embodiments, the biocompatible medium is comprised of a hydrogel.

The term "hydrogel" is used herein to refer to two- or multi-component gels comprising a three-dimensional network of polymer chains, where water acts as the dispersion medium and fills the space between the polymer chains. Hydrogels used in accordance with the presently-disclosed subject matter are generally chosen for a particular application (e.g., a particular spheroid and/or organoid (e.g., a cylindrical organoid)) based on the intended use of the structure, taking into account the parameters that are to be used as well as the effect the selected hydrogel will have on the behavior and activity of the biological materials (e.g., cells) incorporated into the biological suspensions that are to be placed in the structure. Exemplary hydrogels of the presently-disclosed subject matter can be comprised of polymeric materials including, but not limited to: alginate, collagen (including collagen types I and VI), elastin, keratin, fibronectin, proteoglycans, glycoproteins, polylactide, polyethylene glycol, polycaprolactone, polycolide, polydioxanone, polyacrylates, polyurethanes, polysulfones, peptide sequences, proteins and derivatives, oligopeptides, gelatin, elastin, fibrin, laminin, polymethacrylates, polyacetates, polyesters, polyamides, polycarbonates, polyanhydrides, polyamino acids carbohydrates, polysaccharides and modified polysaccharides, and derivatives and copolymers thereof as well as inorganic materials such as glass such as bioactive glass, ceramic, silica, alumina, calcite, hydroxyapatite, calcium phosphate, bone, and combinations of all of the foregoing.

In some embodiments, fibrin gels provide a three-dimensional culture medium for the development of tissue-engineered vascular vessels and networks. Fibrin gels support the attachment of cells to biological surfaces, enhance the migration capacity of transplanted cells, and allow diffusion of growth and nutrient factors. In some embodiments, cells are seeded directly into the gel, e.g., to maximize seeding efficiencies. Fibrin gels possess other favorable qualities that make them effective in tissue-engineered vasculature constructs (Ye et al., European Journal of Cardio-Thoracic Surgery 17(5):587-91 (2000); Jockenhoevel et al., European Journal of Cardio-Thoracic Surgery 19(4):424-30 (2001); Grassl et al., J Biomed Mater Res 60(4):607-12 (2002), each of which is incorporated by reference in its entirety).

In some embodiments, a fibrin gel is derived from a fibrin mixture comprising, e.g., fibrinogen, thrombin, and cells suitable for forming a tissue-engineered vascular vessel. Fibrinogen is a high molecular weight macromolecule (340 kdalton), rodlike in shape, about 50 nm in length and 3 to 6 nm thick. The central domain contains two pairs of bonding sites, A and B, which are hidden by two pairs of short peptides (fibrinopeptides A and B; FPA and FPB). The polymerization sites a and b are at the ends of the outer domains, where other sites susceptible of enzymatic crosslinking are located. Fibrinogen undergoes polymerization in the presence of thrombin to produce monomeric fibrin. This process involves the production of an intermediate alpha-prothrombin which is lacking one of two fibrinopeptide A molecules, which is then followed rapidly (four times faster), by the formation of alpha-thrombin monomer, lacking both fibrinopeptide A molecules (Ferri et al., Biochemical Pharmacology 62(12):1637-45 (2001), which is incorporated herein by reference in its entirety). Sites A and B bind to their complimentary sites on other molecules a and b respectively. The aA interaction is responsible for linear aggregation, while the bB interaction is responsible for lateral growth of the fiber. Thrombin cleavage occurs in a particular manner, first cleaving the FPAs to form linear two-stranded, half staggered chains called profibrils. Subsequently, the FPBs are cleaved allowing the fibrils to aggregate side-by-side increasing in diameter.

DESCRIPTION

The technology described herein relates to vascularization of engineered tissues. Engineered tissues provide potential replacement of their deficient or diseased, native counterparts, thus conceivably curing end-stage disease of multiple organs. Furthermore, promoting the formation of blood vessels in vivo provides cures for many ischemic diseases. Accordingly, the technology described herein finds use, e.g., in embodiments related to medical devices and in various clinical scenarios.

In some embodiments, the technology provides an engineered vascular network that finds use as an in vivo vascular graft, e.g., for an animal, e.g., for a human.

Figure 17:
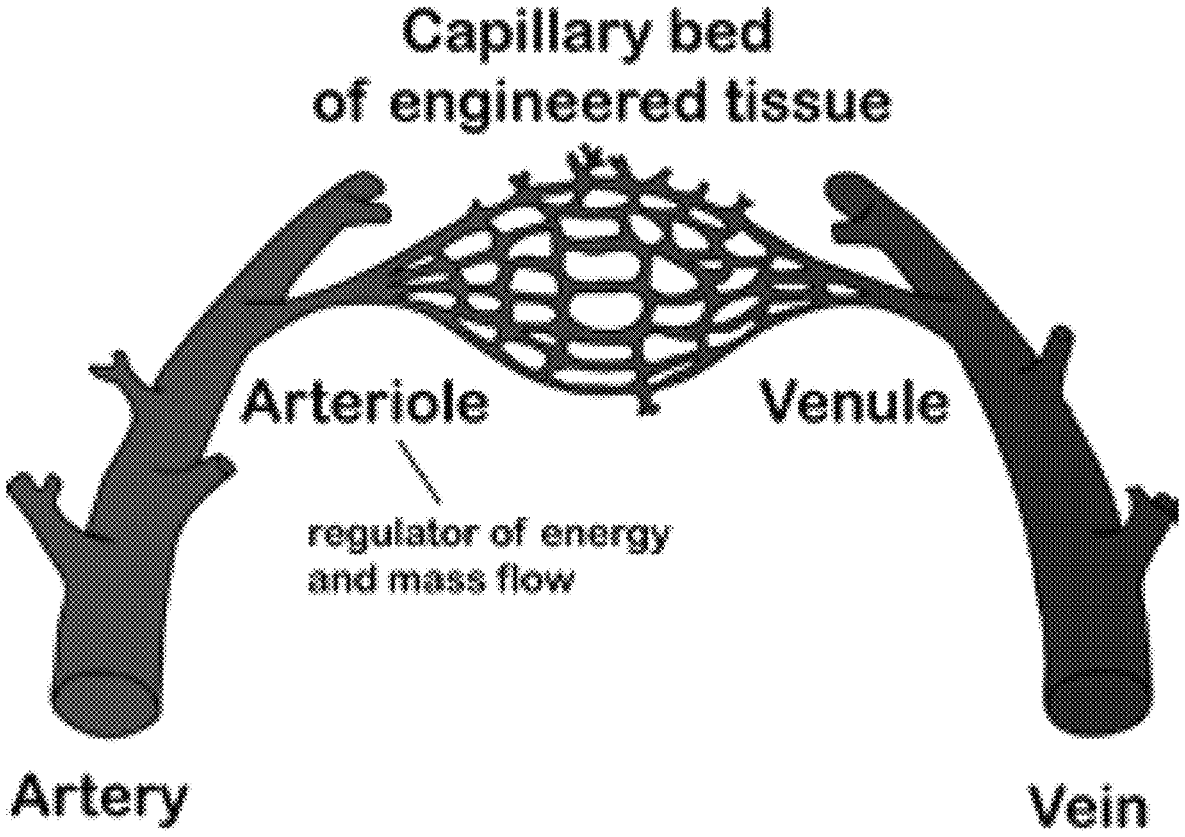
FIG. 17 is a drawing showing an embodiment of the technology provided herein, e.g., a multiscalar and multiphenotype vascular network, e.g., to support thick engineered tissues. Embodiments provide vascular networks comprising arteries, arterioles, capillaries, venules, and veins. Arterioles are critical regulators of energy and mass flow into the engineered tissue.

In some embodiments, the technology described herein provides a multiscalar and multiphenotype vascularization for bioengineered tissues. In some embodiments, the technology provides for the distribution of energy and mass flow (e.g., to parenchymal cells) to engineered tissues, e.g., "thick" engineered tissues, by providing a multiscalar (4 μm to ≥4 mm) and multiphenotype (arterial, microvascular (e.g., capillary), and venous) vasculature to the engineered tissue. Embodiments provide an engineered vascular network that has an architecture that is similar to that of the native terminal vascular bed. For example, embodiments of the engineered vascular network described herein comprise a perfused artery (e.g., approximately ≥4 mm diameter), arterioles (e.g., approximately 10-200 μm in diameter), capillaries (e.g., approximately 4-10 μm in diameter), venules (e.g., approximately 10-200 μm in diameter), and a draining vein (e.g., approximately ≥4 mm in diameter) to provide an adequate vascular supply (FIG. 17). In some embodiments, the artery and vein are at least 4 mm in diameter, e.g., to provide embodiments of a technology appropriate for surgical anastomosis to a patient vascular network. Thus, embodiments of the technology provide a method for de novo creation of a multiscalar and multiphenotype vascularization for bioengineered tissues.

Arterioles play an important role in the vasculature. Arterioles are intermediate-sized vessels that connect larger feeding arteries to the capillaries. Arterioles are the primary resistance vessels, thus making them central regulators of blood flow into the terminal vascular bed. Wound healing and tissue regeneration and/or creation can be viewed as an energy and mass consuming process (see, e.g., 47). Arterial blood flow controls the inflow of substrates for cellular energy production and macromolecule synthesis; thus, arterioles are important regulators of the regenerative and tissue building process. Arteriolar size and amount consequently impact the rate of tissue creation and growth.

Accordingly, promotion of arteriolar genesis is a fundamental step for the tissue building process in tissue engineering in vitro. Without being limited to any particular theory, it is contemplated that arteriolar formation includes processes related to one or both of: (1) an increase in the size of an existing collateral arterial network; or (2) "de novo" formation of new arterial vessels by capillary arterialization (see, e.g., 48). Both mechanisms are promoted by the existence of flow through a small caliber vessel and time for remodeling; thus, technologies based on these processes for in vitro arteriolar genesis in engineered tissues are especially time consuming. Further, an in vitro model of arteriolar genesis is lacking, which further contributes to the lack of insight into this important fundamental process. Accordingly, the technology described herein provides, in some embodiments, a novel method for arteriolar genesis in vitro.

Figure 18:
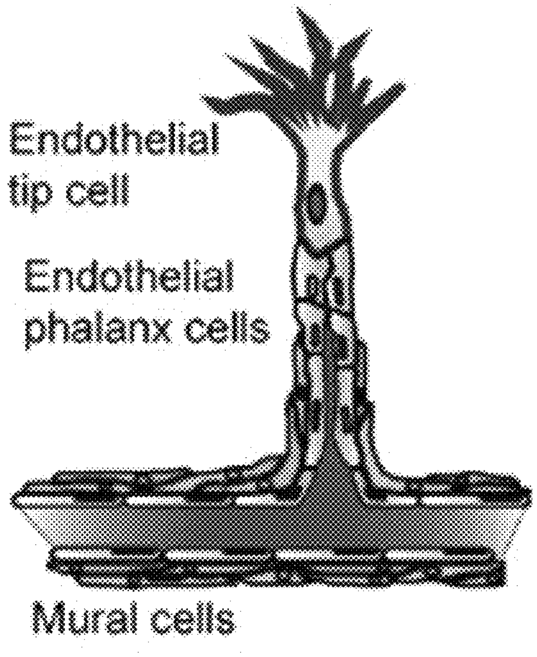
FIG. 18 is a drawing showing the conventional model for angiogenesis driven by ECs and mural cells in which ECs lead the angiogenic sprout, with EC phalanx and mural cells in tow.

In some embodiments, mural cell-led angiogenesis provides a technology for in vitro vessel formation. The traditional, dominant model of angiogenesis is EC-centric. In particular, previous models of angiogenesis provide that EC tip cells lead angiogenic sprouts and orchestrate initiation, direction, rapidity, and recruitment of mural cells (see, e.g., 7) (FIG. 18). Mural cells, also referred to as supportive cells, are recruited to surround nascent microscopic vessels to provide stability and promote maturation. Mural cells include pericytes, MSCs, and vascular SMCs, and there is evidence that these cells may represent slight variations of the same population of mural cells (see, e.g., 49, 50). Current methods to vascularize engineered tissues utilize this angiogenesis paradigm by placing mural cells in proximity to ECS to allow for recruitment and stabilization, but do not necessarily place mural cells in direct contact with ECs (see, e.g., 51).

Figure 19:
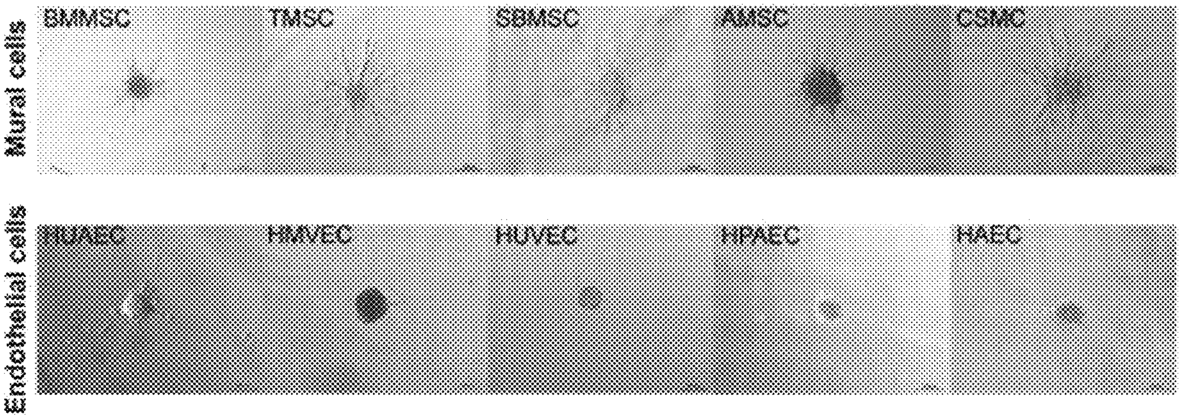
FIG. 19 shows images collected during experiments conducted during the development of embodiments of the technology provided herein; these images and other data indicate that spheroids comprising various types of mural cells demonstrated complex sprouting at 24 hours after embedding in fibrin gel, whereas ECs of various types manifest minimal sprouting (see, e.g., FIG. 1). This angiogenic basis for in vitro sprouting and production of engineered vasculatures was surprising with respect to conventional models, e.g., as discussed in FIG. 18.
Figure 20A:
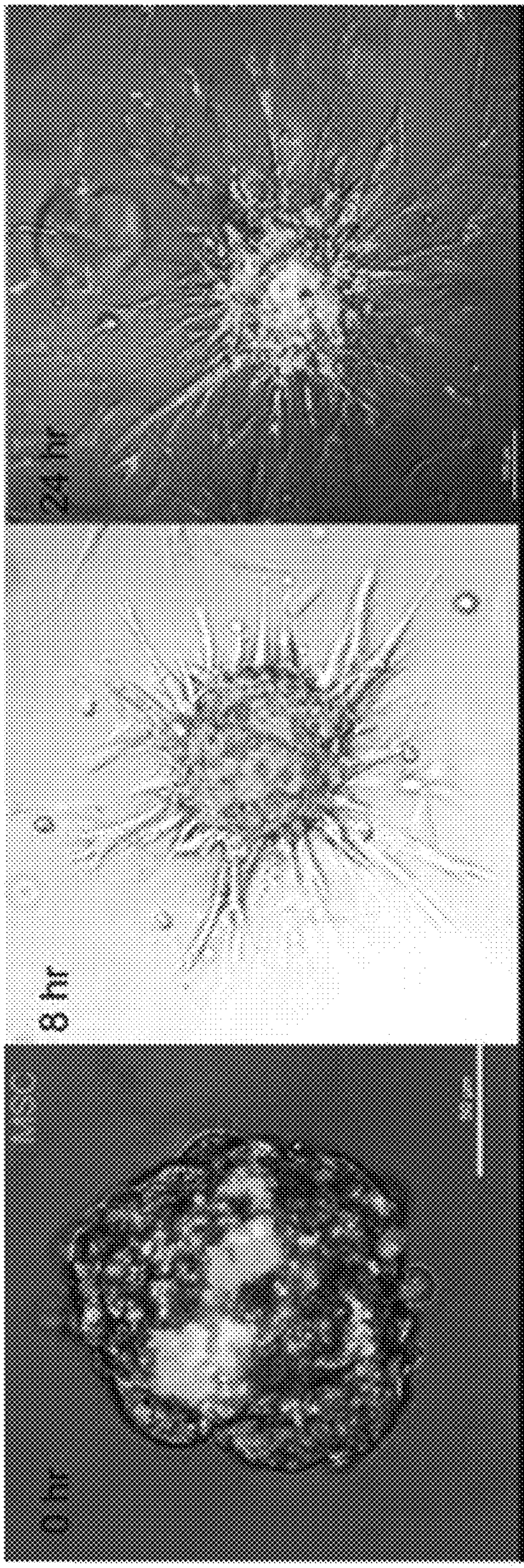
FIG. 20A shows mural cell led angiogenesis in fibrin gel. The images are a time series of spheroids comprising MSCs and HUVECs stained with vital dyes. Most sprouts evident at 8 and 24 hours were derived from MSCs with HUVECs trailing at 24 hours.
Figure 20B:
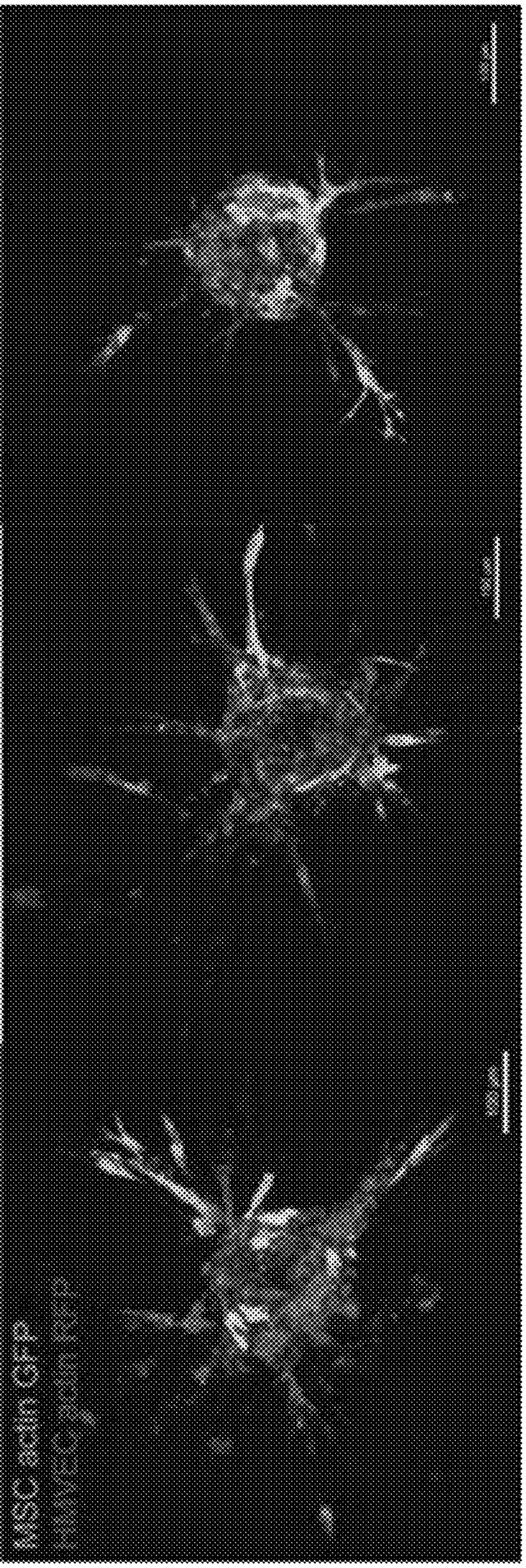
FIG. 20B is a series of images showing sprouting spheroids comprising MSCs and HMVECs transfected with actin GFP and actin RFP, respectively. Sprouts were mostly led by MSCs with HMVECs trailing. In all experiments, total number of cells/spheroid=400 and MSC:HUVEC ratio=1. Results are representative of 3 independent experiments.

In contrast, data collected during the development of embodiments of the technology described herein indicated that angiogenesis and vasculogenesis proceeded according to a different paradigm, which thus provides the basis for embodiments of the technology provided herein. In particular, it was observed that mural cells, including vascular SMCs and MSCs of diverse tissue origins, readily demonstrate sprouting when cultured as spheroids embedded in fibrin gels. Extensive sprouting of mural cell spheroids was observed at 24 hours (FIG. 19). Spheroids made of ECs also manifested simple, less extensive sprouting (FIG. 19).

Some embodiments comprise the use of three-dimensional culture technologies. Three-dimensional environments for cell culture provide a more physiological relevant system for in vitro modeling of cell behavior and for the creation of constructs (e.g., cells, tissues, etc.) for subsequent implantation. In the body, tissues comprise multiple cell types and cells are organized in specific spatial arrangements providing orientation of cells into geometries specific to organ functions. Thus, in some embodiments, cells are grown on tissue culture surfaces; in some embodiments, the technology comprises use of three-dimensional cultures of cells that are often embedded in gel materials (e.g., hydrogel, collagen, fibrin). In some embodiments, two-dimensional and three-dimensional cell cultures produce spheroids during culture. Epithelial and endothelial organoid cultures have been established in this way, e.g., in some embodiments embryonic stem cells are cultured as hanging drops that produce spheroids. In some embodiments, spheroid culture strategies comprise use of several types of cells, e.g., cells of the vasculature and/or parenchymal cells.

In some embodiments, formation of three-dimensional cell and tissue constructs comprises use of bioprinting technologies. Bioprinting, the biologic equivalent of Computer Assisted Design (CAD) and subsequent Computer Assisted Manufacturing (CAM) technologies, includes several different fabrication systems including direct-write bioprinting and ink jet bioprinting. These systems provide CAD-CAM based methods for the controlled deposition of biological materials toward the fabrication of complex biological structures.

In contrast to extant technologies based on a model in which mural cells provide a supporting role to EC tip cells, experiments conducted during the development of embodiments of the technology provided herein indicated that mural cells manifest a more rapid sprouting behavior than ECs when cultured under similar conditions. In particular, mural cells have a more active role in angiogenic sprouting in fibrin gel.

As described in the Examples, MSCs cultured at high density in 3D and in direct contact with ECs promote rapid angiogenic sprouting and lumen formation in fibrin gels. These conditions eliminate or minimize the mural cell recruitment step required in the traditional paradigm and activate mural cell motility, ECM remodeling, and lumen formation. Based on these collective results, provided herein is a technology based on culturing MSCs to produce engineered patent microscopic and macroscopic blood vessels in vitro. This technology comprises use of mural cell (MSC) led angiogenesis to generate a perfuseable, multiscalar, and multiphenotypic blood vessel network in vitro that provides a basis for vascularizing engineered tissues.

Mural cell motility promotes this alternative angiogenic mechanism. As discussed in the Examples, spheroids comprising HUAECs and MSCs inhibited by Rac siRNA manifested sparse and short sprouts. Spheroids with MSCs and HUAEC inhibited by Rac siRNA demonstrated increased sprouting. Control spheroids (scramble siRNA for both cell types) demonstrated the greatest sprouting. Mural cell led angiogenesis occurs when both mural cells and ECs are cultured together in 3D and in high cell density. HUVEC spheroids alone manifest minimal sprouting in fibrin gel at 24 hours. Placing MSCs on top of (or within) the fibrin gel promotes sprouting from HUVEC spheroids. Placing MSC spheroids within (or on top of) fibrin gel also promotes sprouting from HUVEC spheroids. However, culturing MSCs and HUVECs together in spheroids promotes the greatest sprouting.

In some embodiments, the technology provides a method to create a multiscale and multiphenotype vascular network using mural cell-led angiogenesis. In some embodiments, the technology comprises methods to produce one or more components, e.g., (1) an artery (e.g., a macroscopic artery); (2) a microvascular network; and/or (3) a vein (e.g., a macroscopic vein). In particular embodiments, the macroscopic artery and/or macroscopic vein generate arterioles and venules, respectively, that interface with the microvasculature. In some embodiments, the vascular network does not comprise a microvascular network; in some embodiments, the macroscopic vessels produce the capillary network.

In some embodiments, the technology comprises production of solid, macroscopic cords of MSCs and ECs within a hydrogel. In some embodiments, the ECs have an arterial phenotype and, in some embodiments, the arterial ECs yield an artery; in some embodiments the ECs have a venous phenotype and, in some embodiments, the venous ECs produce a vein. In some embodiments, the macroscopic cords of cells form lumens to produce a patent vessel. In some embodiments, the vessels comprise sprouts that form intermediate sized vessels and, in some embodiments, the vessels comprise sprouts that form a capillary network. In some embodiments, the capillary network from the engineered artery and the capillary network from the engineered vein anastomose with each other to produce a perfusable vascular network.

In some embodiments, the technology provides embodiments of a tissue chamber, which is an engineering platform for producing an engineered vascular network according to embodiments of the methods provided herein. In some embodiments, the technology provides in vitro blood vessel network formation in a hydrogel (e.g., a fibrin gels, e.g., a linear channeled fibrin gel). In some embodiments, the engineering platform comprises linear mm-scale channels that are formed by a mechanically removable substrate. In some embodiments, the channeled hydrogel platform comprises channels of 1 to 10 mm (e.g., 1, 2, 3, 4, 5, 6, 7, 8, 9, or 10 mm) in diameter. In some embodiments, the channeled hydrogel platform comprises channels of at least 4 mm diameter. In some embodiments, the channels provide templates to guide the engineered macrovessels. In some embodiments, the platform comprises inlet and outlet ports to provide perfusion. In some embodiments, the engineered microvascular network is generated in the hydrogel.

Some embodiments provide a single channeled hydrogel platform comprising inlet and outlet ports connected to a liquid perfusion circuit. In some embodiments, the channel is approximately 1 to 10 mm (e.g., 1, 2, 3, 4, 5, 6, 7, 8, 9, or 10 mm) in diameter. In some embodiments, the hydrogel platform is housed in a hypoxic incubator. In some embodiments, the hydrogel platform comprises closable side ports. In some embodiments for the production of an engineered vascular network in the hydrogel platform, fibrin and/or thrombin are injected through closeable side ports. In some embodiments, the tissue chamber is a closed system constructed from PDMS and comprises a glass coverslip top and/or a glass bottom to transmit light for imaging. In some embodiments, the single channeled platform finds use to generate an engineered vasculature, e.g., under normoxic conditions, e.g., as described herein.

Embodiments of the technology comprise use of an engineered vasculature as described herein. In some embodiments, the engineered vasculature technology finds use in producing complex channeled hydrogels. In some embodiments, producing complex channeled hydrogels comprises use of liquefiable removable substrates (2, incorporated herein by reference) or 3D printing (52, incorporated herein by reference). In some embodiments, the tissue chamber housing the channeled gel is a closed system, e.g., to minimize contamination. In some embodiments, the tissue chamber is placed in a conventional or hypoxic incubator, e.g., to permit perfusion and live imaging. In some embodiments, the dimensions of the tissue chamber are approximately 1-10 mm (e.g., 1, 2, 3, 4, 5, 6, 7, 8, 9, or 10 mm)×1-10 mm (e.g., 1, 2, 3, 4, 5, 6, 7, 8, 9, or 10 mm)×1-10 mm (e.g., 1, 2, 3, 4, 5, 6, 7, 8, 9, or 10 mm).

In some embodiments, the technology comprises use of primary human mural cells (UASMCs and thymus MSCs) and ECs; in some embodiments, the technology comprises use of pluripotent stem cells, e.g., derived MSCs and ECs.

In some embodiments, macroscopic arteries and macroscopic veins are produced by seeding channels in hydrogel with both ECs and MSCs at high density. In some embodiments, the MSCs are at a high density in three dimensions and are in direct contact with ECs, e.g., to promote mural cell led angiogenesis, e.g., in which vessels sprout from the engineered vessels. In some embodiments, providing MSCs at a high density in three dimensions and in direct contact with ECs promotes the formation of a lumen in the vessels. Extant methods comprise seeding the surface of a hollow channel to yield a patent vascular structure; however these extant methods produce no or minimal angiogenic sprouting. In contrast, the technology provided herein comprises producing a solid core of MSCs and ECs within a hydrogel. In some embodiments, the lumenogenic properties of MSCs produce a patent vessel (e.g., additionally comprising patent, complex branches).

In some embodiments, single channel constructs are generated with MSCs and HUAECs and HUVECs. In some embodiments, engineered vessels form branches within one week of static culture.

In some embodiments, the technology relates to constructs comprising both an engineered artery (thymus MSCs+HUAECs) and an engineered vein (thymus MSCs+HUVECs). In some embodiments, these engineered vessels were separated by 0.1-10 mm (e.g., 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5, 6, 7, 8, 9, or 10 mm). In some embodiments, the engineered vessels sprout 4 days after static incubation. In some embodiments, after one week of incubation, sprouting yields arterioles, venules, and capillaries. In some embodiments, the sprouted arterioles, venules, and capillaries are extremely dense throughout the entire construct, especially between the two engineered vessels. In some embodiments, the vascular network comprising the arterioles, venules, and capillaries can be infused with fluorescent microspheres, e.g., the arterioles, venules, and capillaries are patent such that the microspheres are able to enter the arterioles, capillaries, and venules. Perfusion of the vascular network from the arterial side causes the microspheres to reside within the engineered vein after travel through the vascular network. Accordingly, the technology provides, in some embodiments, a complete and perfuseable vascular network formed in vitro. In some embodiments, the perfusable vascular network comprises a macroscopic engineered artery and, in some embodiments, the perfusable vascular network comprises a macroscopic engineered vein. In some embodiments, the macroscopic engineered artery and the macroscopic engineered vein are separated by considerable distance; and, in some embodiments, the macroscopic engineered artery and the macroscopic engineered vein are separated by an intervening complex capillary network. In some embodiments, the vascular network further comprises parenchymal cells (e.g., cardiomyocytes, skeletal myocytes, hepatocytes, and/or insulin producing 6 cells). In some embodiments, methods comprise providing parenchymal cells (e.g., cardiomyocytes, skeletal myocytes, hepatocytes, and/or insulin producing 6 cells) and/or maintaining in vitro perfusion to produce a dense, thick tissue as well as to support a large number and high density of cells. Accordingly, the technology provides advantages for tissue engineering that were not previously capable with routine 2D and 3D culture techniques.

Figure 16:
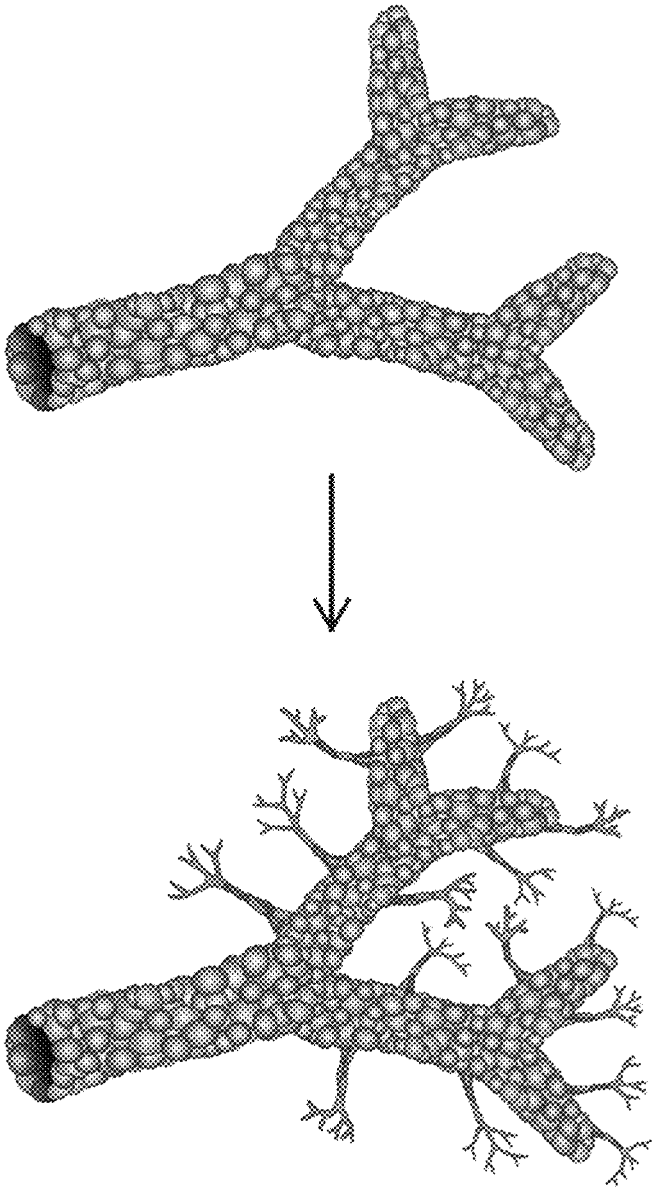
FIG. 16 is a drawing showing an embodiment of the technology related to a 3D bioprinted MSC based complex organoid.

Provided herein is a novel approach for producing complex and expansive engineered vascular networks. In some embodiments, the technology provides a flow-through, cylindrical organoid. In some embodiments, the engineered vascular network finds use in producing complex macrovascular architectures, e.g., that are provided by 3D bioprinting technology (see, e.g., FIG. 16).

Embodiments of the technology provide an engineered vasculature network in which the engineered new blood vessels form from the outside toward the inside. Accordingly, in some embodiments the luminal surface has an increased endothelialization by perfusing the network with ECs or endothelial progenitor cells that attach to the MSC-formed basement membrane.

Some embodiments of the technology comprise methods to increase the connections between engineered arteries and veins. For example, in some embodiments microvascular endothelial cells are encapsulated in the fibrin gel prior to cylindrical organoid formation and sprouting. This approach accelerates the generation of microvascular connections between the engineered artery and vein and/or increases the number of microvascular connections between the engineered artery and vein.

In some embodiments, the cylindrical organoids and emanating vascular networks are engineered to withstand in vivo pulsatile pressure and flow. For example, in some embodiments the robustness of the engineered vascular networks is improved by modifying the cell composition of the cylindrical organoids, e.g., by increasing the amount of SMCs relative to ECs and/or MSCs. In some embodiments, robustness of the engineered vascular networks is improved by adding ascorbic acid during construct formation to promote collagen formation. In some embodiments, robustness of the engineered vascular networks is improved by hemodynamic conditioning.

In some embodiments, the engineered vascular networks described herein are incorporated into a bioreactor, which provides an important advantage relative to extant technologies.

Embodiments of the technology provide systems for producing an engineered vascular network. For example, embodiments of systems comprise one or more of, e.g., a tissue chamber as described herein, a hydrogel (e.g., fibrin and/or components for producing fibrin (e.g., fibrinogen and thrombin)), cells (e.g., ECs, MSCs), an incubator, syringes, tubes, etc.

Embodiments of the technology provide kits for producing an engineered vascular network. For example, embodiments of kits comprise one or more of, e.g., a tissue chamber as described herein, components for producing fibrin (e.g., fibrinogen and thrombin), syringes, tubes, instructions for use of the kit, etc.

In some embodiments, the technology finds use in producing engineered vascularized tissue. For example, in some embodiments the technology finds use in producing vascularized, perfuseable engineered tissue using MSC driven angiogenesis.

In some embodiments, a comprehensive engineered vascular network is generated (FIG. 14) and perfused. Then, in some embodiments, parenchymal cells (e.g., cardiomyocytes, skeletal myocytes, or adipocytes) are added to the vascularized construct (e.g., in serial fashion), which promotes remodeling of the vasculature to become incorporated into the added parenchymal cells.

In some embodiments, an alternative approach comprises adding parenchymal cells along with the fibrin gel in the tissue chamber prior to engineered vasculature formation.

In some embodiments, the technology finds use in producing improved decellularized organs and vasculature. A problem of extant organ and/or tissue decellularization and recellularization technologies is the destruction and inefficient seeding of native microvascular networks. Accordingly, the technology described herein solves this problem for revascularizing decellularized organs and tissues, e.g., by infusing MSCs (with or without ECs and/or followed by ECs) into the decellullarized vasculature in high densities to promote expression of ECM remodeling genes and the partial digestion of native basement membrane. Subsequently, MSCs lead new angiogenic sprouts into the parenchyma, thereby establishing a new, complex microvascular network.

In some embodiments, the technology finds use in vivo to promote therapeutic angiogenesis. For example, in some embodiments MSC driven angiogenesis is used to deliver MSC organoids in vivo, e.g., to provide therapeutic angiogenesis. Although MSC spheroids have been proposed for therapeutic use, the technology described herein produces cylindrical organoids that produce larger arterioles in vivo, thus providing greater clinical efficacy. In some embodiments, the technology comprises use of a fibrin gel construct containing cylindrical organoids and emanating microvascular networks that is placed adjacent to a perfused artery, e.g., that borders an ischemic region of tissue. The engineered vasculature inosculates with the recipient vasculature and becomes perfused. In embodiments providing cylindrical organoids and emanating microvascular networks having a macroscopic scale, longer distances of ischemic regions are bridged with the presently described vascularized construct relative to, for example, extant technologies providing proangiogenic stem cell injections.

In some embodiments, the technology finds use in, e.g., grafts for treatment of vascular diseases, providing an engineered vasculature for engineered tissues and/or organs, and/or for preclinical drug testing and biological assays.

Although the disclosure herein refers to certain illustrated embodiments, it is to be understood that these embodiments are presented by way of example and not by way of limitation.

EXAMPLES

Materials and Methods

3D Printed Plastic Mold (e.g., for PDMS Tissue Chamber)

Figure 21:
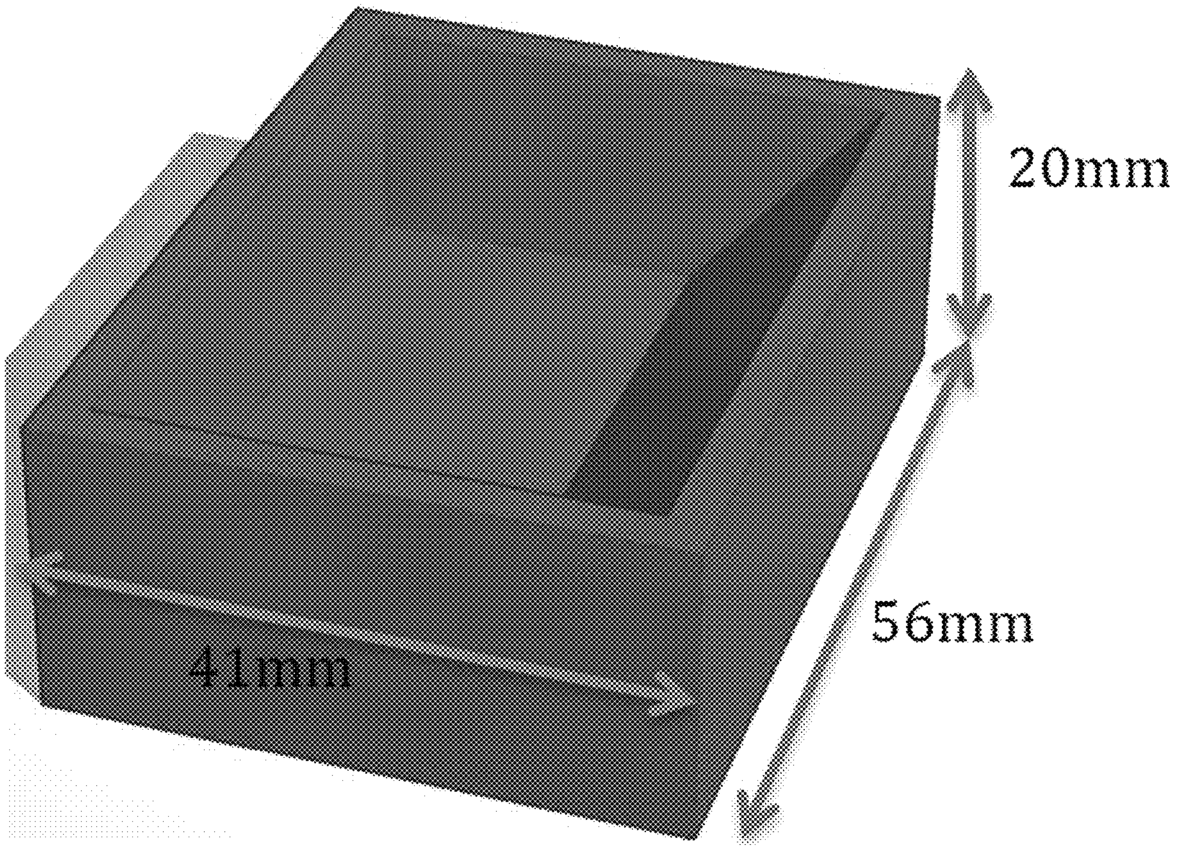
FIG. 21 shows a drawing of a base to support a cubical mold for producing a tissue chamber as described herein.
Figure 22:
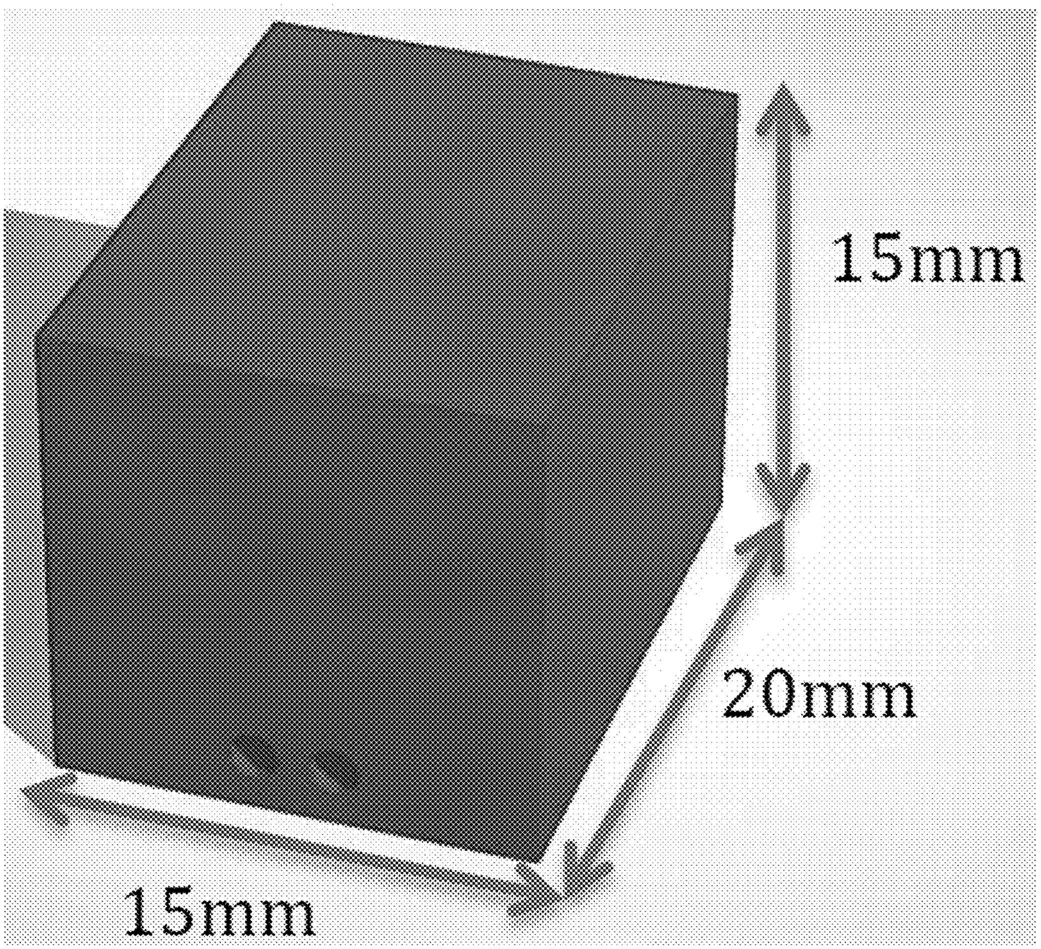
FIG. 22 shows a drawing of a cubical mold with two hollow cylindrical spacers approximately 1 mm from the base for producing a tissue chamber as described herein.

Design software (e.g., Tinker CAD, www.tinkercad.com) was used to design a base (FIG. 21) and a cubical mold with a hollow cylindrical spacer (FIG. 22) about 1 mm from its base. All cubical mold designs follow the same cube shape with either one or two channels 1 mm from the bottom. Channel diameter varies to accommodate the tubing gauge (e.g., 15 or 18). For example, 15-gauge tubes are used with a cubical mold comprising 2.1-mm diameter channels, and 18 gauge tubes are used with a cubical mold comprising 1.5-mm diameter channels. The designs were saved as a ".stl" file and printed at the University of Michigan 3D Lab. The 3D printed plastic mold was prepared for use in forming the PDMS tissue chamber by inserting the appropriate gauged hypodermic tubing (e.g., either 15 or 18 gauge) into the cubical mold, and then placing the cubical mold with tubing into the base.

Making the PDMS Tissue Chamber

PDMS mixture was prepared using a 10:1 ratio of Base: Curing Agent (Slygard Eslastomer) and mixed thoroughly using a vortex. The amount of PDMS depends on the size of base being used; typically 30-40 mL are enough to fill most base sizes. The PDMS mixture is poured into the 3D-printed plastic mold base. While filling the base, the polymer mixture is poured evenly around the cubical mold and the cubical mold is centered and pressed against the bottom of the base. The PDMS is poured into the base to fill the base to the top of the cubical mold or so that it minimally covers the top of the cubical mold. Extra PDMS is saved so that it can be used to attach the cover plate to the mold after it cures. The 3D-printed plastic mold filled with PDMS (tissue chamber) is placed in an oven to cure for 90 minutes at 90° C. Next, the cured PDMS tissue chamber is cut and shaped.

Figure 23:
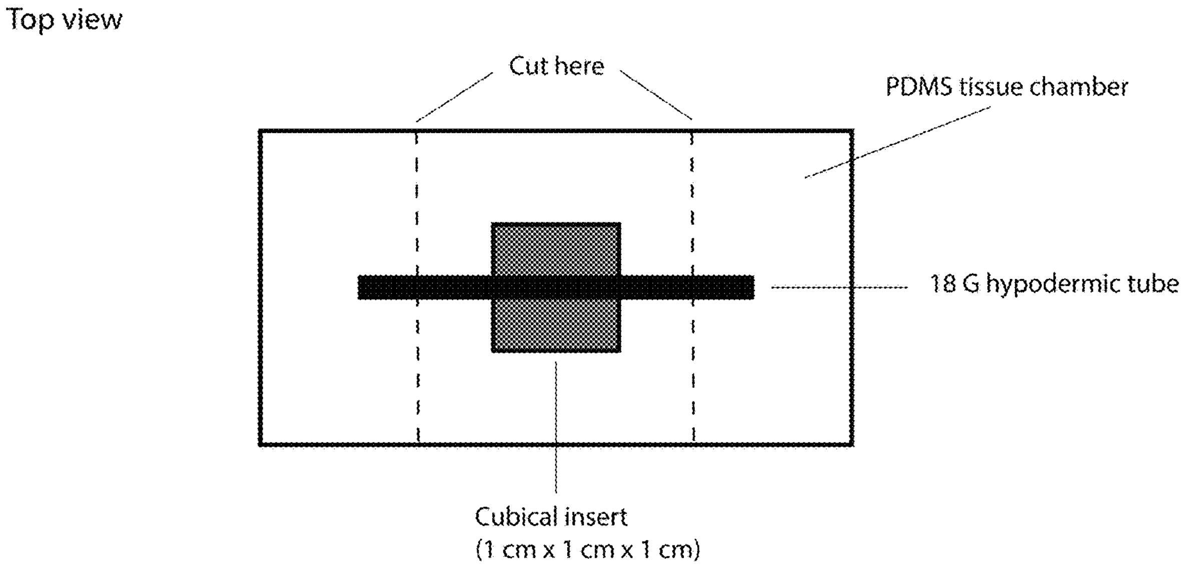
FIG. 23 is a drawing showing the shaping, cutting, and components of an embodiment of a PDMS tissue chamber as described herein.
Figure 24:
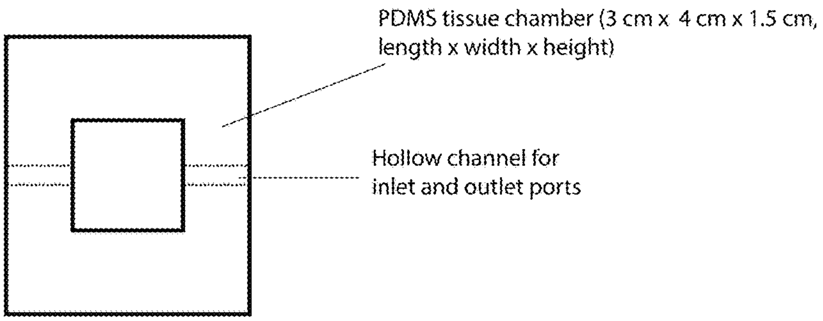
FIG. 24 shows top view and oblique view drawings of an embodiment of the PDMS tissue chamber as described herein.
Figure 24:
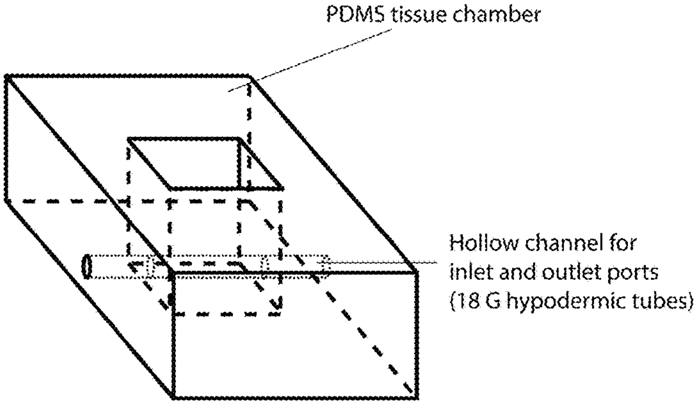
Figure 25:
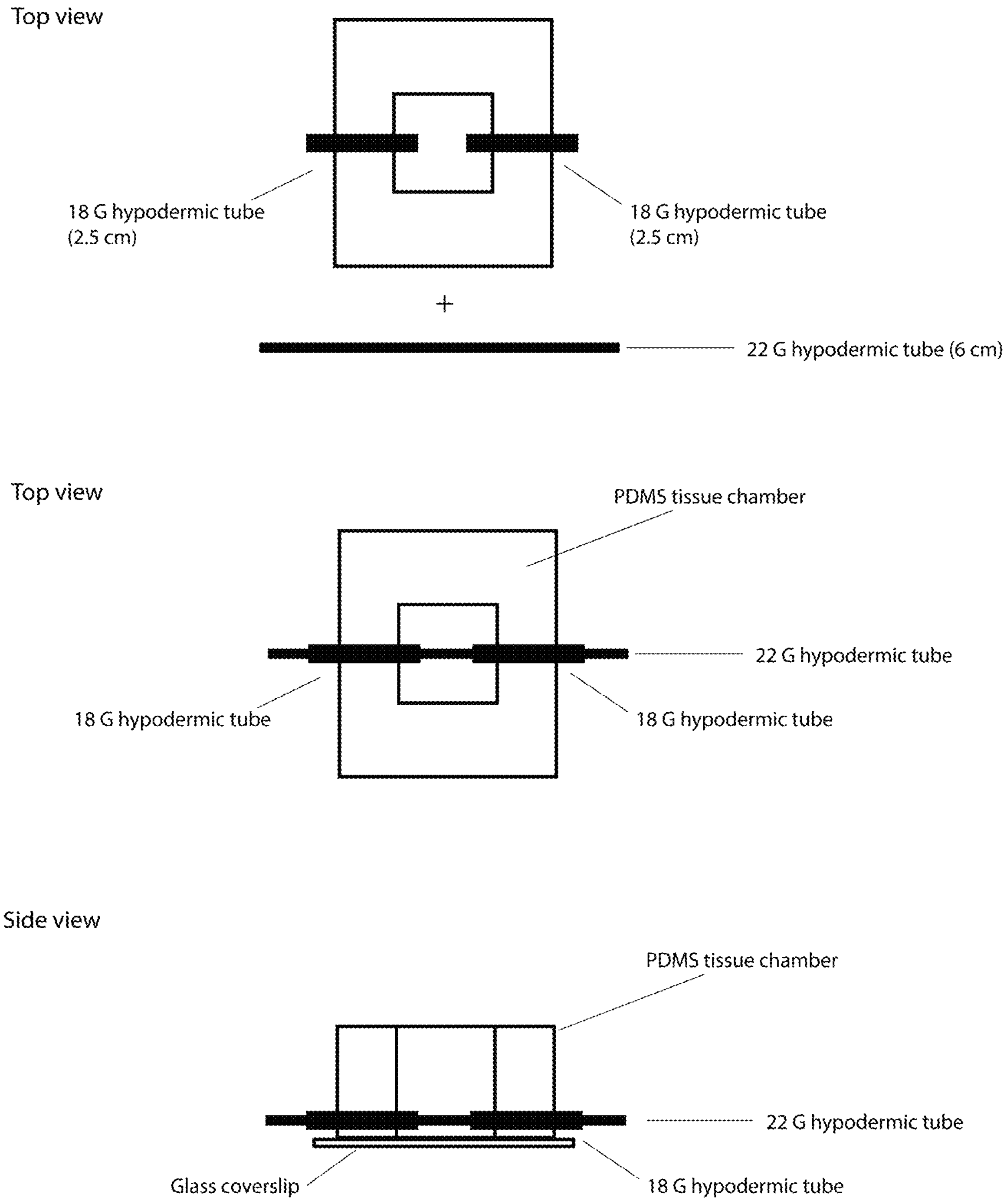
FIG. 25 is a set of top and side view drawings of an embodiment of a PDMS tissue chamber as described herein.

The PDMS tissue chamber is gently separated from the 3D printed plastic mold using a scalpel and spatula, e.g., by gently working around the edge of the base to liberate the tissue chamber from the base. The PDMS tissue chamber is shaped, e.g., according to FIG. 23. Then, the hypodermic tube is removed to provide a hollow channel (FIG. 24). The PDMS covering the top and bottom of the 3D printed plastic cubical mold is cut and then gently remove from the PDMS tissue chamber. Next, 2.5-mm hypodermic tubes of the appropriate gauge are inserted into the newly formed channels in the PDMS tissue chamber so that one end is present in the gap created from the removal of the cubical mold (FIG. 25). Then another, longer hypodermic tube is inserted into the 2.5-mm hypodermic tubes so that it stretches across the entire gap created by the removal of the 3D-printed plastic cubical mold to act as a spacer (see, e.g., FIG. 25). In some exemplary embodiments, 22-gauge tubing fits inside of the 18-gauge tubing, and the 18-gauge tubing fits inside of the 15-gauge tubing (see, e.g., FIG. 25).

Next, a cover glass (microscope) is fixed to the bottom of the cured PDMS tissue chamber using the extra PDMS saved from above (FIG. 25). The tissue chamber is incubated at 90° C. for 20 minutes in the oven to cure the PDMS. The proper orientation is shown in FIG. 25. The tissue chamber is checked to assure that the PDMS is applied to create a total seal around the hole in the cured PDMS tissue chamber to minimize and/or prevent leaking when media and fibrin gel are added. The PDMS tissue chamber is autoclaved, e.g., at G30 Cycle for 67 minutes. In addition, tools used for seeding of cells are autoclaved. These include pipet tips used to seed and pliers that will be used to have been sterilized.

In a sterile fume hood, the PDMS tissue chamber is removed from the autoclave bag and placed in a petri dish. A fibrin gel is produced in the PDMS tissue chamber by mixing fibrinogen and thrombin: Fibrinogen diluted to 20 mg/mL; Thrombin 10:1 dilution.

1000 μl of thrombin is added to the construct followed by 660 μl of fibrinogen (e.g., to provide approximately a 3:2 ratio of thrombin:fibrinogen). The tissue chamber is then incubated at 37° C. in 5% $CO_2$ for 45 minutes. After incubation, the spacer tubing is carefully removed to produce a hollow channel within the fibrin gel. Then, using a pliers, the hypodermic tubes are gently pushed at either end of the channel approximately 1 mm into the gel. During the development of embodiments of the technology, it was discovered that this step improved the device. In particular, a funnel-shaped connection is created between the channel and the hypodermic tubes because when the spacer is removed. This funnel-shaped connection is problematic because cells seeded into the channel bypass the tube and enter the gel instead of going into the channel. Pushing the hypodermic tube into the gel eliminates the funnel-shaped connection and creates a tight seal between the channel and the tube. Next, 1000 μl of ECM are added on top of the fibrin gel; this media is replaced with fresh media every two days. After seeding with cells (see below), the construct and petri dish are incubated at 37° C. at 5% $CO_2$, and vessel viability and growth are monitored daily.

Seeding Channel with Cells

Starting from a monolayer cell culture, cells are dissociated by rinsing with PBS followed by incubating with dissociation solution (trypsin/EDTA). For example, for a 75-$cm^2$ flask, 5 mL of PBS and 2 mL of trypsin are used. As a further example, mesenchymal stromal cells (MSCs) are trypsinized for 3 minutes and endothelial cells (ECs) are trypsinized for 2 minutes. After dissociation, the dissociation is deactivated using cell media comprising FBS. For example, for a 75-$cm^2$ flask with 2 mL of trypsin, 4 mL of cell media are used to deactivate trypsin. As a further example, MSCs use DMEM cell media and ECs use ECM.

Next, cells suspended in cell media and trypsin are aspirated and dispensed into a conical tube to hold them until they are needed. In some embodiments, the above steps are repeated for each cell type to seed a mixture of cell types. For each cell type, cell count is measured (e.g., using a hemocytometer) to determine the volume (e.g., mL) of cells+media+trypsin mixture to provide the desired cell number. For example, for PDMS tissue chambers using 22-gauge channels, 200,000 cells are seeded per channel; for example, for PDMS tissue chambers using smaller 18-gauge channels, 400,000 cells are seeded per channel. For PDMS tissue chambers produced for use with multiple cell types, the cell types are evenly divided; (e.g., when using two cell types in a 22-gauge channel, 100,000 cells of each cell type are used).

(cells/mL)×(mL of cells+media+trypsin mixture)=(total cell number)

(cells needed/total cell number)×(mL cells+media+trypsin mixture)=(mL of mixture needed to provide desired cell number).

Then, the desired mL of cells to provide the necessary cell number are separated and placed in new conical tube. In the case of mixed cell-type tissue engineered constructs, all cell types are placed together in the same conical tube. Next, cells are pelleted, e.g., by centrifuging at 1000 RPM for 5 minutes. Media is removed from the cell pellet, e.g., by gently aspirating off the media from cell pellet (making sure not to disturb the pellet itself) and re-suspending the cells in ECM. For example, cells being prepared for seeding in 22-gauge channels are re-suspended in 40 μl per channel (40 μl× # of channels); cells being prepared for seeding in 18-gauge channels are re-suspended in 100 μl per channel (100 μl× # of channels). An autoclaved pipet tip is used to aspirate gently re-suspended cells and dispense them into the PDMS tissue chamber by carefully inserting the pipet tip into the hypodermic tube and slowly emptying the tip. i. Dispense slowly and smoothly in order to prevent air bubbles from forming and entering the channel and to prevent the channel from bursting. The tissue engineered constructs may be observed by microscope to assess visually that the channel was properly seeded, e.g., cells should be present throughout the channel in a consistent density filling the channel. After seeding, the tissue engineered construct and petri dish are incubated at 37° C. in 5% $CO_2$ and the vessel viability and growth are monitored daily.

Imaging Tissue Engineered Constructs

All images are saved to an external hard drive. ZEN imaging software application is used for image capture and processing. Turn on microscope power, e.g., a Zeiss Primo Vert Microscope with Microscopy Camera AxioCam MRc5. Tissue constructs are imaged using a 4× lens at an aperture setting of Ph1/0.4. After removing the tissue engineered construct from the incubator, it is placed on the microscope stage and imaged.

For example, using the ZEN imaging software, click the "LIVE" button to provide a real-time image of the construct. Focus is adjusted so that the cells in the channel, and branches they have formed, are as clear as possible (for some software, the focus observed through the microscope eyepiece does not match the focus seen on the screen, so it is best to focus the image when looking at the screen and not when looking through the microscope). Brightness and contrast are adjusted, e.g., by adjusting the background lighting by either changing the intensity of the microscope light using the dial on the right side of the microscope or by clicking the "Set Exposure" button in the upper left part of the screen. For some software, the proper objective for the image is set to add an accurate scale bar to the image, e.g., for the ZEN imaging software, using a drop down menu on the left side of the screen, change the objective to match the lens, 4×. Activate scaling before capturing an image; after establishing a clear image, click the "Snap" button in the upper left part of the screen to capture the image. Add a scale bar to the image by clicking the ruler icon at the top of the screen. With a 4× lens, the scale bar corresponds to 200 μm. Save the image to media, e.g., a hard drive. The image is saved with information regarding the cell types in the tissue-engineered construct, the passage number of those cell types, the age of the construct, and the size and number of channels. Repeat steps until images have been taken over the entirety of the channel/channels.

Example 1—MSC-Based Spherical Organoids Manifest Sprouting Tubulogenic Behavior In Vitro Thymus-derived and bone-derived MSCs cultured in spherical organoids (also known as spheroids) and implanted in fibrin gel are known to produce a rapid and complex sprouting and tubulogenic response (see, e.g., 8, 9, incorporated herein by reference).

Accordingly, during the development of embodiments of the technology provided herein, experiments were conducted to test the tubulogenic response using MSCs from a wider variety of tissues. Data collected during the experiments indicated that the previously observed tubulogenic behavior was not specific for MSCs from bone and thymus tissue. In particular, human MSCs from various tissue sources consistently manifested tubulogenic behavior when cultured in spherical organoids and embedded in fibrin gel (FIG. 1).

Spherical organoids comprising human ECs from various tissue sources also generated tubules, but at a lesser degree and rate relative to those comprising MSCs.

The addition of ECs to MSCs or in spherical organoids produced an even greater sprouting response after embedding in fibrin gel (FIG. 1).

Figure 2A:
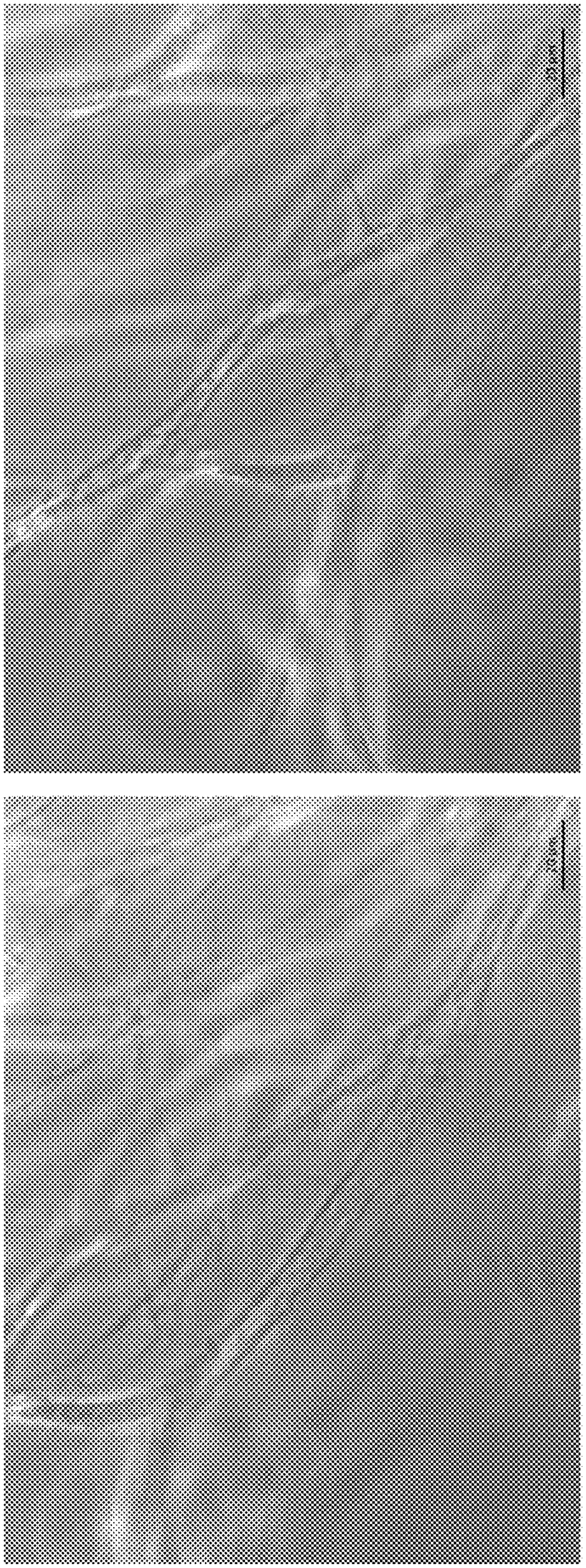
FIG. 2A shows brightfield microscope images of tubules sprouting from MSC+EC spherical organoids. Spherical organoids comprising thymus MSCs+HUVECs were imaged five days after embedding in fibrin gel.

In additional experiments conducted during the development of the technology provided herein, bright field microscopy confirmed the presence of bona fide tubules from MSC+EC spherical organoids. In particular, bright field microscopy was used to observe sprouting spherical organoids comprising thymus MSCs+HUVECs five days after embedding in fibrin gel. Data collected from the bright field microscopy indicated the presence of bona fide and complex branching tubule formation originating from the spherical organoids. (FIG. 2A).

Figure 2B:
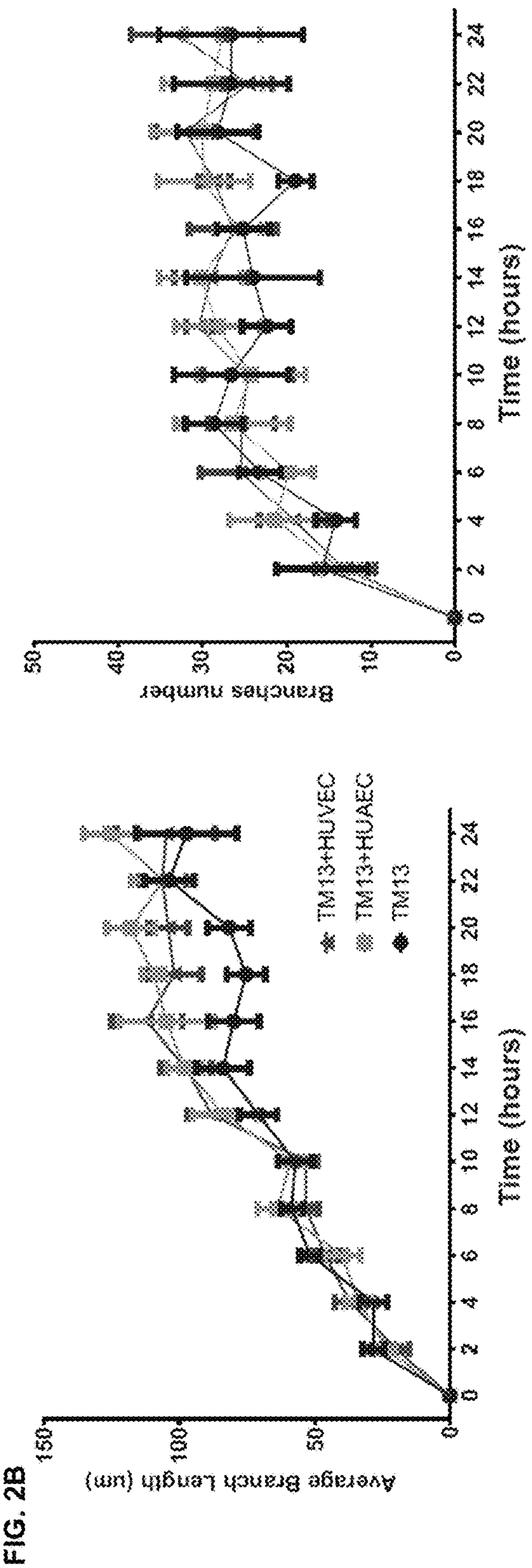
FIG. 2B shows plots of average branch length and branch number as a function of time in hours for MSC-based spherical organoid sprouting. Spherical organoids comprising MSCs, MSCs+HUVECs, or MSCs+HUAECs were embedding in fibrin gel and branch length and branch number were monitored. “TM13” is a thymus MSC line.

During the development of embodiments of the technology described herein, experiments were conducted to measure the kinetics of MSC-based spherical organoid sprouting. Data collected during the experiments indicated that sprouting began as early as 2 hours in spherical organoids comprising embedded MSCs and MSCs+ECs (FIG. 2B). The lengths of sprouts increased at approximately 5 mm/hour over the 24-hour observation period (FIG. 2B, left panel). The number of branches per spherical organoid reached a plateau by approximately 8 hours (FIG. 2B, right panel).

Example 2—Impact of MSC Location and Density on Sprouting of Spherical Organoids MSCs are known to influence the behavior of ECs by paracrine processes (e.g., signaling) (see, e.g., 10). Further, high density and three-dimensional culture are known to promote the production of proangiogenic growth factors by MSCs (see, e.g., 9, 11, 12). Accordingly, it was contemplated that spherical organoids comprising MSCs and ECs produce sprouts predominantly comprising ECs led by tip ECs and that the MSCs promoted sprouting by paracrine processes.

During the development of embodiments of the technology described herein, experiments were conducted to evaluate this proposed mechanism. In particular, experiments were conducted to determine if MSCs acted by paracrine processes to promote sprouting from spherical organoids comprising ECs. In the experiments, data were collected by varying the location and density of MSCs relative to fibrin gel-encapsulated spherical organoids comprising ECs. The following different conditions were tested: (A) MSCs cultured as a monolayer on top of fibrin gel comprising EC organoids; (B) individual MSCs encapsulated in fibrin gel comprising EC organoids; (C) MSC spherical organoids cultured on top of fibrin gel comprising EC organoids; and (D) MSC spherical organoids encapsulated in fibrin gel comprising EC organoids (FIGS. 3A-3D, respectively). In parallel experiments, ECs present in the fibrin gel as MSC+EC spherical organoids were tested at both 1× and 0.5× amounts of cells (FIGS. 3E and 3F, respectively). Fibrin gel-encapsulated spherical organoids comprising ECs were used as a control (FIG. 3G).

In the experiments, the ratio of MSCs:ECs was 1:1 and the total number of MSCs and ECs were the same. To control for total cell number/spherical organoid, a control was performed using a second group of spherical organoids that contained half the number of MSCs and ECs (FIG. 3E). The negative control comprised EC spherical organoids encapsulated in fibrin gel with no MSCs (FIG. 3G). MSCs and ECs were respectively labelled with green and red vital dyes for these experiments.

Figure 3:
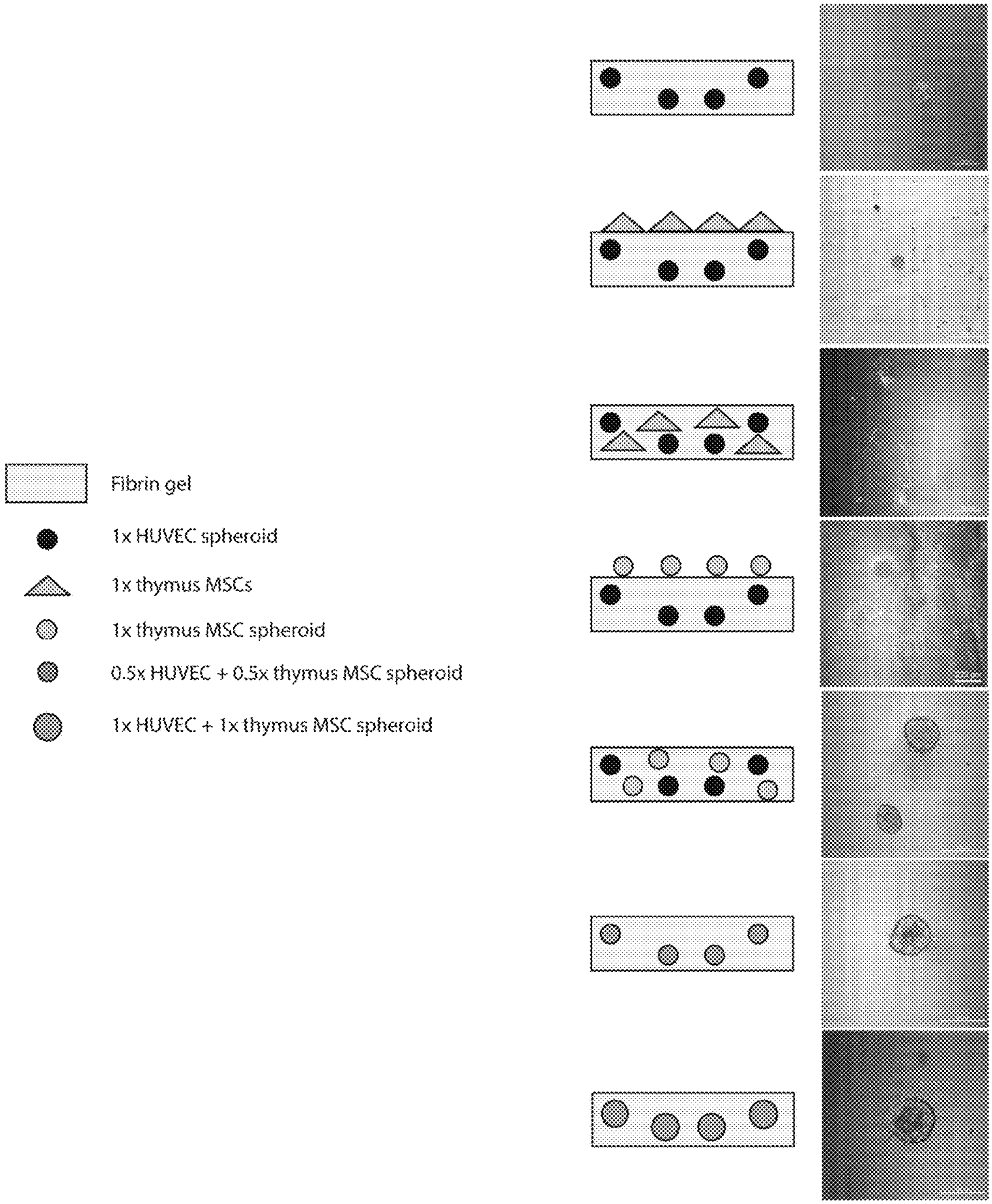
FIG. 3 is a series of schematic drawings and microscope images showing that the most robust sprouting is observed in organoids that comprise a mixture of both MSCs and ECs.

In these experiments in which the location and density of MSCs within the fibrin gel were varied, the data collected indicated that the increased sprouting response was observed in the experiments in which the MSCs were included within the spherical organoid with the ECs (FIG. 3, especially FIGS. 3E and 3F). Encapsulating MSCs within the fibrin gel along with EC-only spheroids (FIG. 3B) or as a monolayer on top of fibrin gels containing EC-only spheroids (FIG. 3A) did not result in the same increased sprouting response observed when both types of cells were present together in the spheroid configuration. These results indicated that MSC paracrine action does not contribute significantly (e.g., dominantly) to promote spherical organoid sprouting. In contrast to previous studies in the field indicating a major role for paracrine signaling, the data collected during the development of the technology described herein indicated a surprising result. In particular, the determination that spherical organoids comprising only MSCs demonstrated a brisk sprouting response was unexpected.

Example 3—MSCs Lead Spherical Organoid Sprouting in Fibrin Gel

During the development of embodiments of the technology provided herein, experiments were conducted to collect additional data relating to this observation. In particular, it was contemplated that MSCs were responsible for leading or creating the sprouts seen in MSC+EC spherical organoids. This basis for the technology described herein is clearly contrary to the teachings of the art concerning the traditional paradigm of angiogenesis, from which one would predict that sprouts are led by tip ECs.

Accordingly, experiments were conducted during the development of the technology provided herein to evaluate MSC-led sprouting. In particular, data were collected in tracking experiments in which MSCs and ECs were first labelled with green and red vital dyes prior to constructing spherical organoids and embedding the organoids in fibrin gel.

Figure 4A:
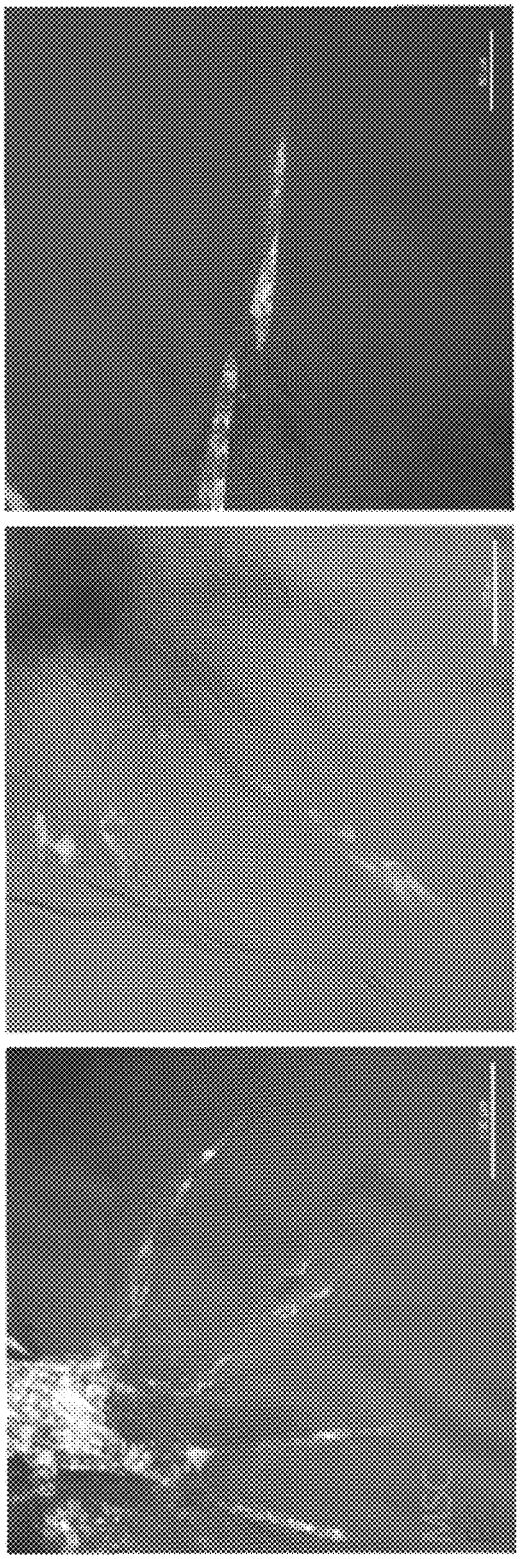
FIG. 4A shows microscope dye tracking images in which MSCs and ECs were respectively labelled first with green and red vital dyes prior to spherical organoid creation and embedding in fibrin gel. Most sprouts comprised MSCs, with a small subset also containing ECs after 24 hours. Sprouts mostly comprised MSCs and all were led by MSCs. Furthermore, no ECs were detectable at the tip of the sprouts, indicating that MSCs had initiated and led sprouting from these spherical organoids.

Data collected indicated that most of the sprouts comprised MSCs; a small subset of organoids also comprised ECs after 24 hours (FIG. 4A).

Sprouts mostly comprised MSCs and all sprouts were led by MSCs. Furthermore, no ECs were detectable at the tip of the sprouts, indicating that MSCs had indeed initiated and led sprouting from these spherical organoids.

Figure 4B:
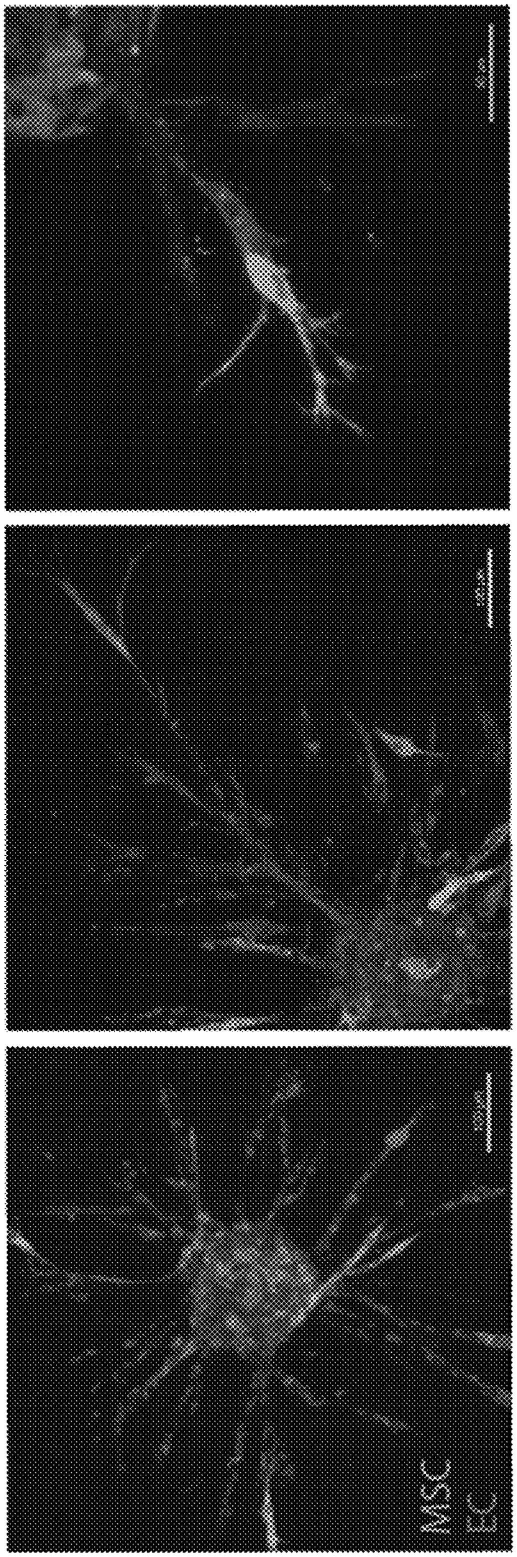
FIG. 4B shows microscope images showing that most of the sprouting emanating from the spherical organoids was due to MSCs. MSCs were transiently transfected with GFP-actin and ECs were transiently transfected with RFF-actin prior to making spherical organoids and embedding in fibrin gel. Sprouts were consistently stained green from the MSC actin fibers that produced the filopodia creation and extension and sprout formation.

Experiments were also conducted to test if dye transfer between these two cell populations in the spherical organoids could have produced the observed MSC-led sprouting. Data were collected in experiments designed specifically to visualize the actin fibers in the sprouts because it is known that actin is responsible for producing and extending filopodia, which contributes to sprout formation in tip ECs that lead angiogenic sprouting (see, e.g., 13,14). In these experiments, actin was visualized by transiently transfecting MSCs with GFP-actin and by transiently transfecting ECs with RFP-actin prior to making spherical organoids and embedding the organoids in fibrin gel. The data collected from these experiments confirmed that most of the sprouting emanating from the spherical organoids was due to MSCs and was not produced by the ECs (FIG. 4B).

Figure 4C:
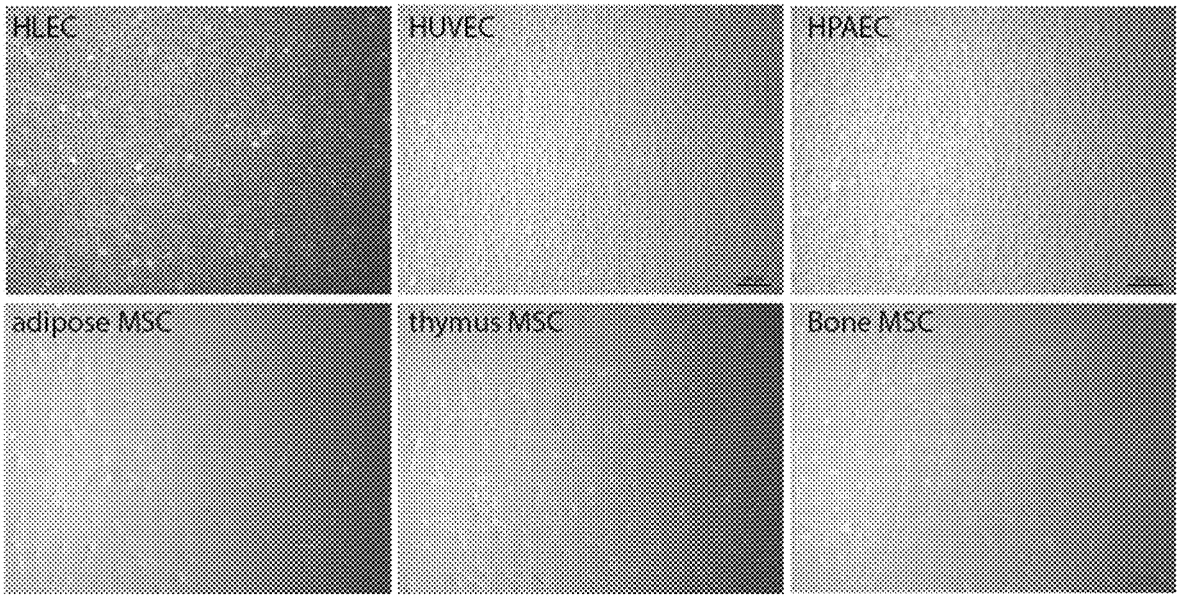
FIG. 4C shows microscope images of the cultures of MSCs and ECs used for the experiments. The images show that the ECs and MSCs appeared morphologically distinct from each other. Further, the images indicate that the ECs did not comprise a subpopulation of MSCs and the MSCs did not comprise a subpopulation of ECs.
Figure 4D:
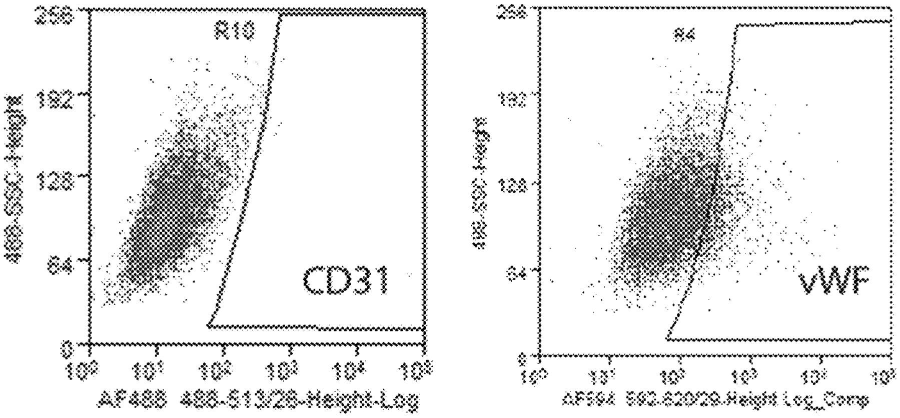

Experiments were next conducted to test if the MSCs that were collected for the experiments also contained a contaminating population of ECs. The likelihood of contamination was extremely low because the MSCs were passaged at least 5 times in standard growth medium without EC growth factors and ECs and MSCs appeared morphologically distinct from each other (FIG. 4C). In addition, the MSCs were tested for the presence of the classical EC markers CD31 and vonWillebrand's factor (vWF). The MSCs lacked detectable CD31 expression and vWF expression was approximately 10% (FIG. 4D). These data are consistent with previous reports indicating that vWF expression is found at a very low baseline level in MSCs or is slightly higher upon stimulation with VEGFA in MSCs from various tissues (see, e.g., 15-19). Thus, these data indicated that the MSCs collected did not comprise a subpopulation of contaminating ECs.

Figure 5C:
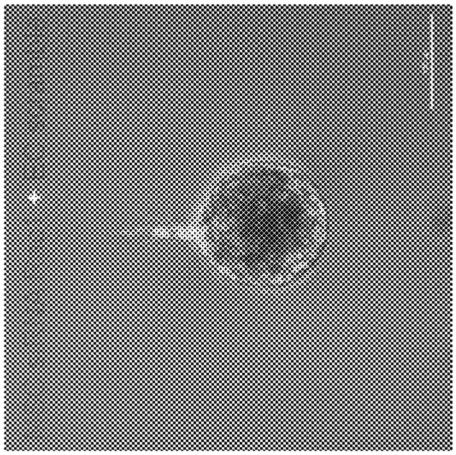
FIGS. 5A-5C show microscope images from experiments testing the importance of MSC motility in MSC led sprouting. Rac1, a key regulator of filopodia formation and cellular motility, was inhibited by transfection of siRNA in either MSCs or ECs prior to creating spherical organoids from the transfected cells. Scrambled siRNA was used as a control.
Figure 5B:
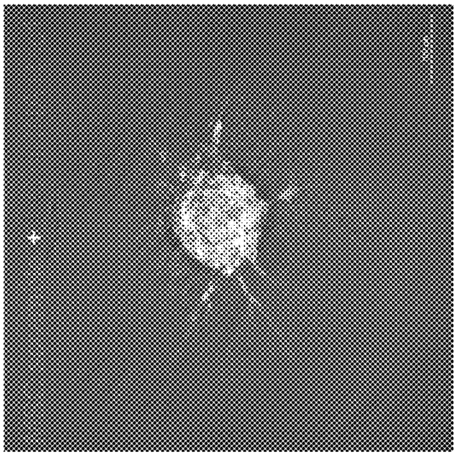
Figure 5A:
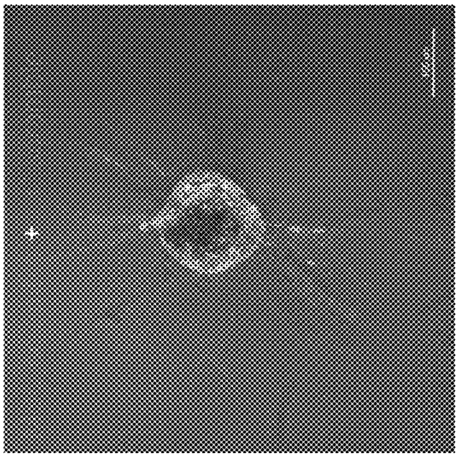

Example 4—Inhibiting MSC Motility Abrogates MSC+EC Spherical Organoid Sprouting During the development of embodiments of the technology provided herein, additional experiments were conducted to evaluate the role of MSC motility in MSC-led sprouting. Rac is a key regulator of filopodia formation and cellular motility (20). Accordingly, Rac1 was inhibited by siRNA prior to creating spherical organoids. Control spherical organoids made with MSCs and ECs transfected with scramble siRNA manifested brisk sprouting at 24 hours (FIG. 5A). Spherical organoids comprising MSCs and ECs transfected with scramble and Rac siRNA, respectively, had decreased sprouting (FIG. 5B). Spherical organoids comprised of MSCs and ECs transfected with Rac siRNA and scramble siRNA, respectively, demonstrated essentially no sprouting (FIG. 5C). Collectively, these results reinforce the concept that MSCs are indispensable in leading and contributing to sprouting from MSC+EC spherical organoids.

These data indicate that MSCs form long, branching sprouts when cultured in a spherical organoid and embedded in fibrin gel, which are contrary to the traditional paradigm of tip EC-led angiogenic sprouting.

Example 5—Lumen Formation in MSC Spherical Organoids

Figure 6A:
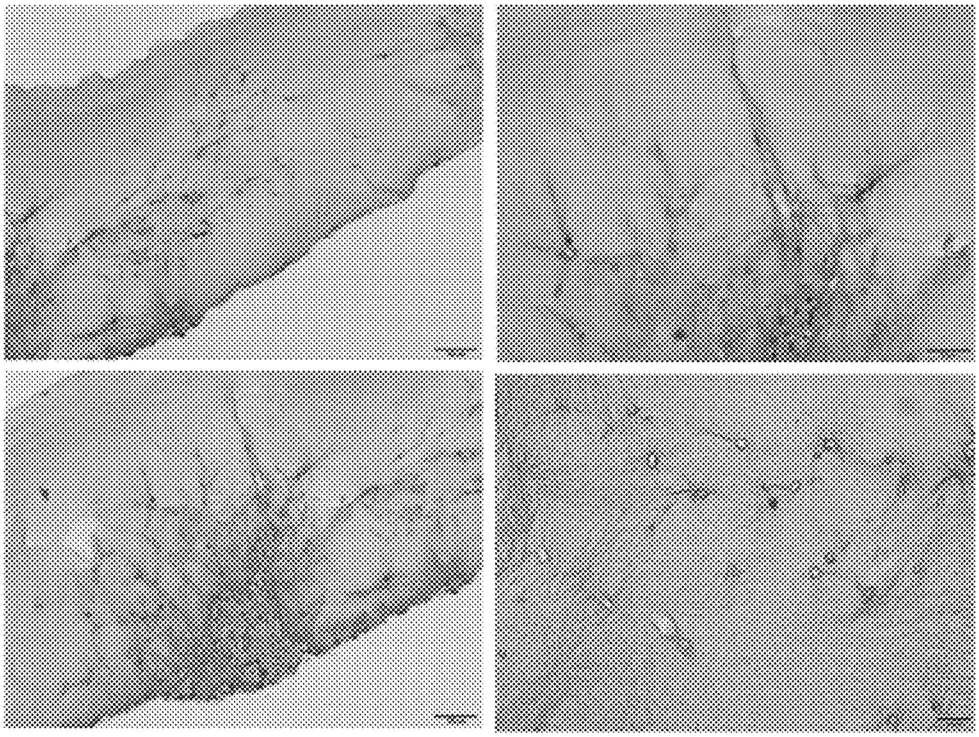
FIG. 6A is a series of microscope images that show the patency of sprouts branching from MSCs in a spherical organoid comprising MSCs and ECs embedded in fibrin gel. Histology was performed on sprouting MSC+EC spherical organoids two days after embedding them in fibrin gel. Serial sections through the sprouting MSC+EC spherical organoids revealed cross sections of patent tubules emanating from the central cell mass.
Figure 6B:
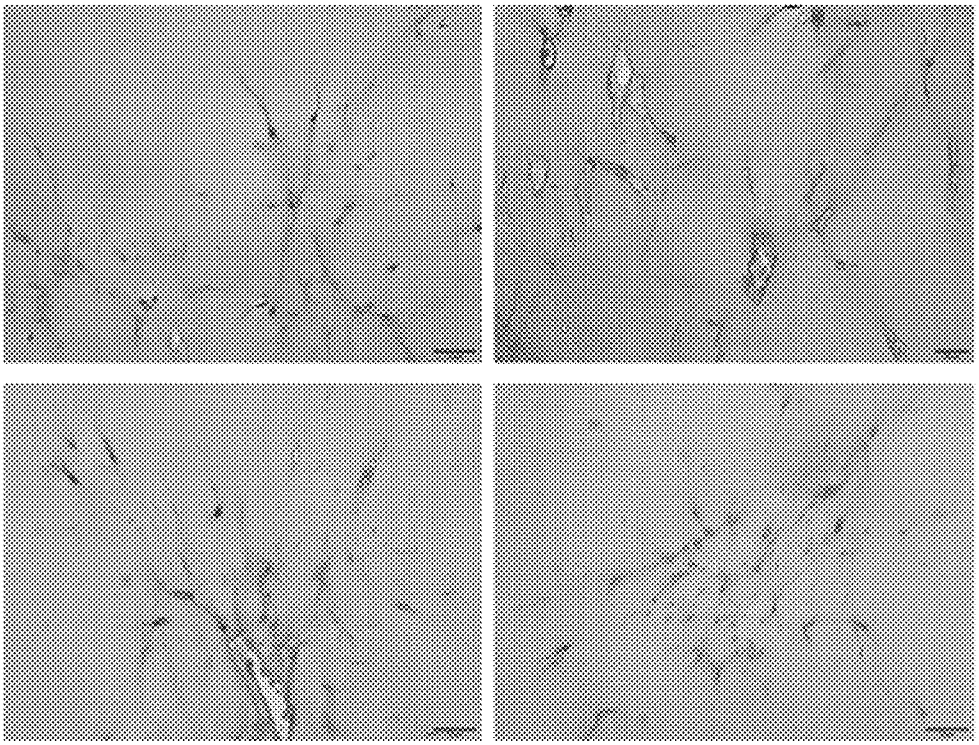
FIG. 6B is a series of microscope images that show the patency of sprouts branching from MSCs in a spherical organoid comprising MSCs (but no ECs) embedded in fibrin gel. Histology was performed on sprouting MSC spherical organoids two days after embedding them in fibrin gel. Serial sections through the sprouting MSC spherical organoids revealed cross sections of patent tubules emanating from the central cell mass.

While MSCs form long, branching sprouts, it was unclear if the sprouts are "patent" (hollow) and thus provide a vascular conduit. Accordingly, experiments were conducted to evaluate lumen formation in the sprouts. In particular, histology was performed on sprouting MSC+EC and MSC spherical organoids two days after embedding them in fibrin gel. Serial sections through sprouting MSC+EC spherical organoids revealed cross sections of patent tubules emanating from the central cell mass (FIG. 6A). Patent tubules were also seen in serial sections through sprouting MSC spherical organoids (FIG. 6B), further indicating that MSCs produce functioning vasculature.

Further, experiments were conducted to measure the expression of genes known to be involved in vascular lumen formation in ECs and in two different types of MSCs cultured in monolayer (2D) and as spherical organoids (3D)

Figure 6C:
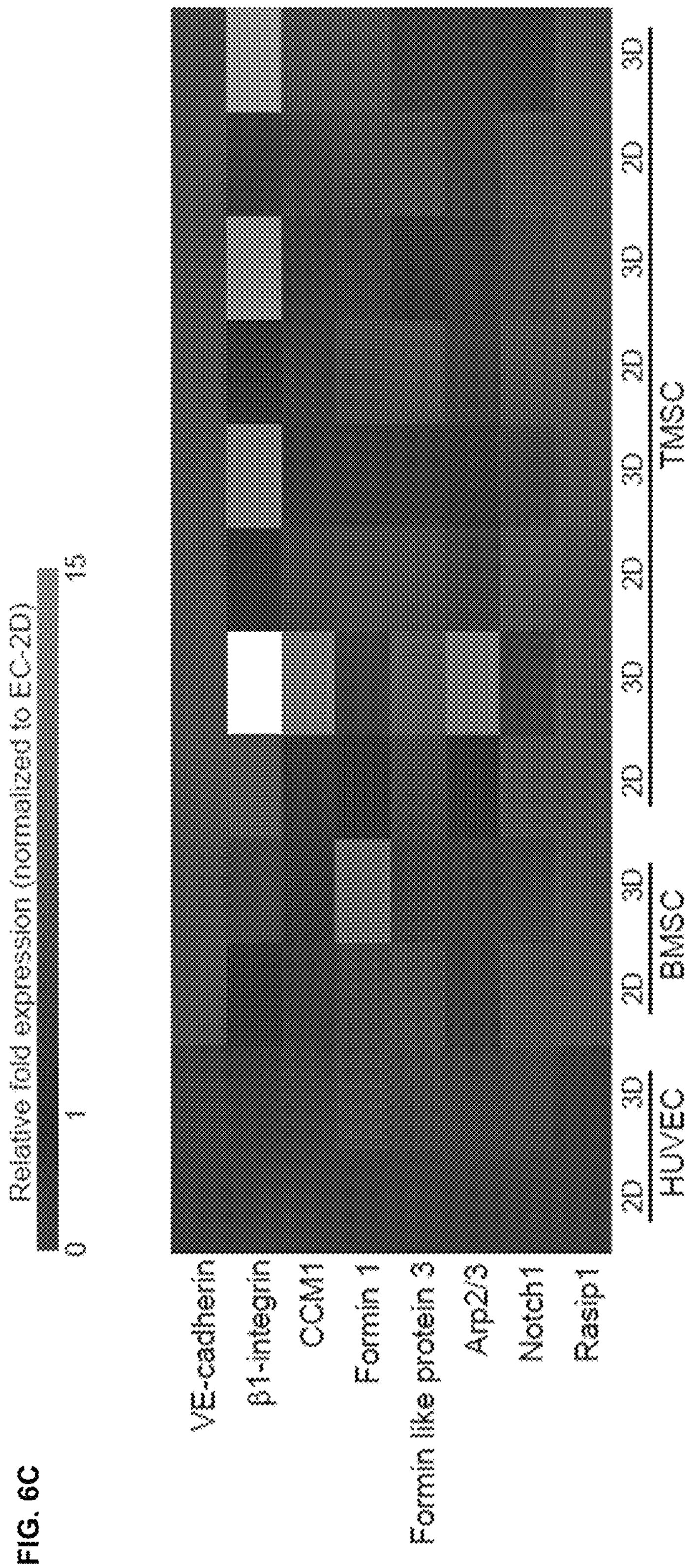
FIG. 6C is a heat map showing the expression of genes known to be involved in vascular lumen formation in ECs and two different types of MSCs cultured in monolayer (2D) or as spherical organoids (3D). MSCs cultured in three-dimensional spherical organoid form had an increased expression of lumen forming genes relative to the expression of the same genes in MSCs cultured in two-dimensional culture, with the exception of VE-cadherin and Rasip1.

(see, e.g., 21-28). Data collected from these experiments were consistent with the presence of patent tubules emanating from MSC spherical organoids. In general, MSCs cultured in spherical organoid form demonstrated increased expression of lumen forming genes, with the exception of VE-cadherin and Rasip1 (FIG. 6C).

Example 6—MSCs in Spherical Organoids Demonstrate Broad Activation of Angiogenic and ECM Gene Networks MSCs from multiple tissue types, when cultured in high cell density and in spherical organoid form, produce hollow vessels in fibrin gel (see, e.g., Example 5, supra). As discussed above, these observations were unexpected because one would have predicted ECs to have been responsible for sprouting and vessel production based on the knowledge in the field.

Figure 7:
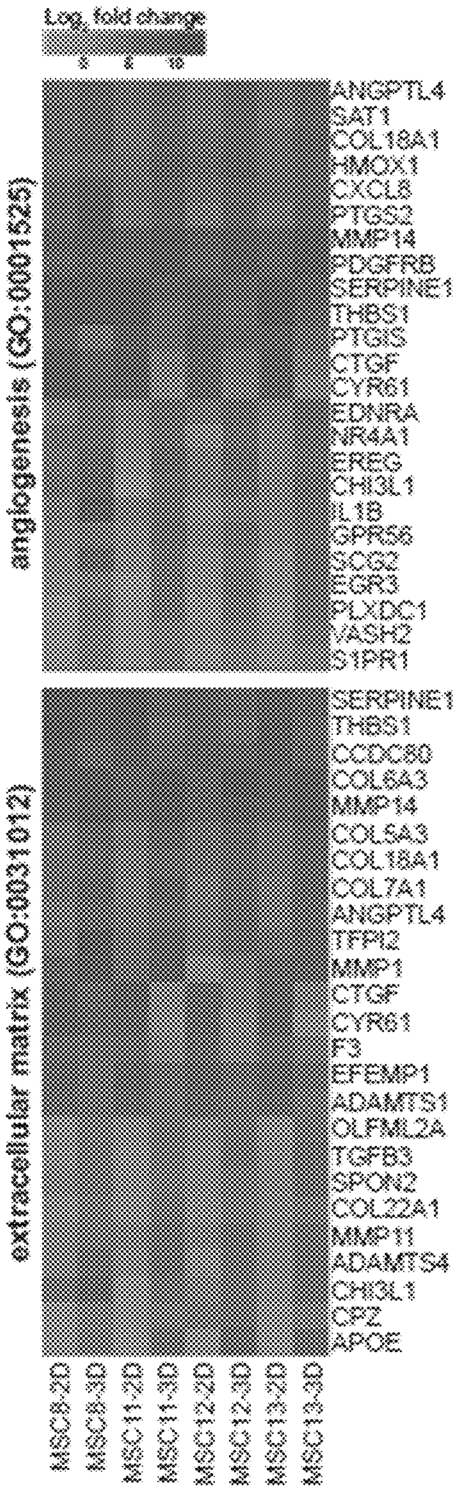
FIG. 7 is a heat map showing the results of global transcriptome profiling by RNA sequencing analysis of 4 different thymus MSC lines cultured in either monolayer (2D culture) or as spherical organoids (3D culture, but not embedded in fibrin gel). Whole genome profiling revealed the activation of gene networks involved in angiogenesis and extracellular matrix remodeling when the MSCs were cultured in three-dimensions relative to the activation of the same genes in MSCs cultured in two-dimensional monolayers.

Thus, experiments were conducted during the development of embodiments of the technology provided herein to evaluate the factors contributing to the sprouting and tubulogenesis of MSCs in spherical organoids. In particular, data were collected from global transcriptome profiling experiments and RNA sequencing of four different thymus MSC lines cultured in either monolayers or as spherical organoids, but not embedded in fibrin gel. The whole genome profiling data indicated the activation of gene networks involved in angiogenesis and extracellular matrix remodeling (FIG. 7). Furthermore, the expression of a number of genes associated with murine tip ECs were also found to be increased (Table 1) (see, e.g., 29).

TABLE 1

Genes upregulated in both tip ECs and MSC spherical organoids

| Gene Name | Protein | Fold Change in Human MSCs Spherical Organoids |
|---|---|---|
| PLAUR | uPAR | 5.21 |
| APLN | Apelin | 4.87 |
| ESM1 | Endothelial-specific molecule 1 | 8.06 |
| GMFG | Glia maturation factor g | 12.18 |
| TGFB1 | TGFb1 | 2.58 |
| SOX7 | Sox7 | 3.71 |
| SOX17 | Sox17 | 4.54 |
| EDG1 | S1PR1 | 7.31 |
| RASGRP3 | Ras guanyl releasing protein 3 | 2.92 |

Native tissue studies and in vivo observations by others have detected mural cell-led angiogenesis in the: (1) rat mesentery after intraperitoneal injection of mast cell degranulating substance or tumor conditioned media; (2) developing retina; and (3) tumors (30, 31), the latter two being in vivo scenarios of rapid tissue growth. Formation of vasculature lacking ECs in tumors has been referred to as vascular mimicry. Gene expression changes previously observed in human melanoma vascular mimicry (see, e.g., 32,33) are similar to gene expression changes observed in MSC spherical organoids during the experiments described herein (Table 2).

TABLE 2

Genes upregulated in both vascular mimicry and MSC spherical organoids

| Gene Name | Desciption | Fold Change in Human MSCs Spherical Organoids |
|---|---|---|
| | angiopoietin-like 4 | 6.67 |
| COL18A1 | collagen, type XVIII, alpha 1 | 5.66 |
| CXCL5 | chemokine (C-X-C motif) ligand 5 | 9.89 |
| CXCL6 | chemokine (C-X-C motif) ligand 6 | 2.71 |
| CXCL10 | chemokine (C-X-C motif) ligand 10 | 17.07 |
| EDG1 | S1PR1 | 7.31 |
| EFNA1 | ephrin-A1 | 5.38 |
| HGF | hepatocyte growth factor (hepapoietin A; scatter factor) | 15.51 |
| ID3 | inhibitor of DNA binding 3, dominant negative helix-loop-helix protein | 0.287 |
| IL18 | interleukin 18 (interferon-gamma-inducing factor) | 0.232 |
| MMP9 | matrix metallopeptidase 9 (gelatinase B, 92 kDa gelatinase, 92 kDa type IV collagenase) | 712.50 |
| NRP1 | neuropilin 1 | 1.91 |
| PGF | placental growth factor | 3.97 |
| PLXDC1 | plexin domain containing 1 | 31.31 |
| THBS1 | thrombosopondin 1 | 0.174 |
| VEGFA | VEGFA | 1.706 |
| VEGFC | VEGFC | 0.651 |

Figure 8B:
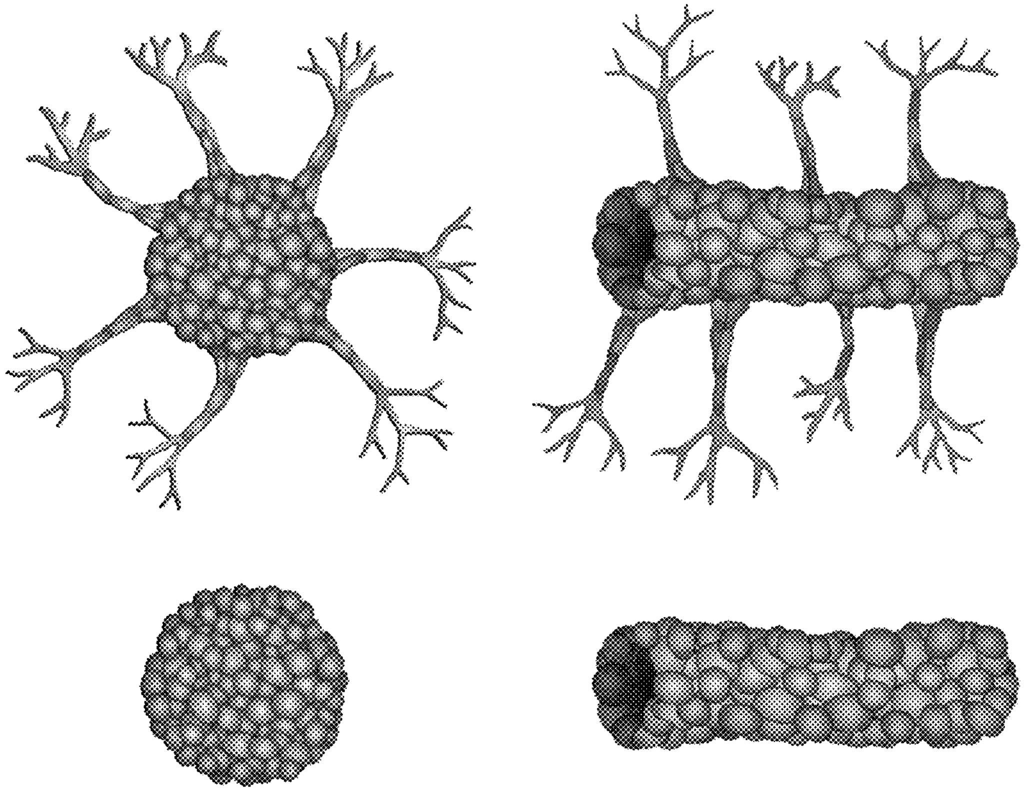
FIG. 8B is a schematic drawing showing the patent vessel branching from MSC-based spherical organoids provided herein and a model for tubular, macroscale engineered vessels comprising patent branches.
Figure 8A:
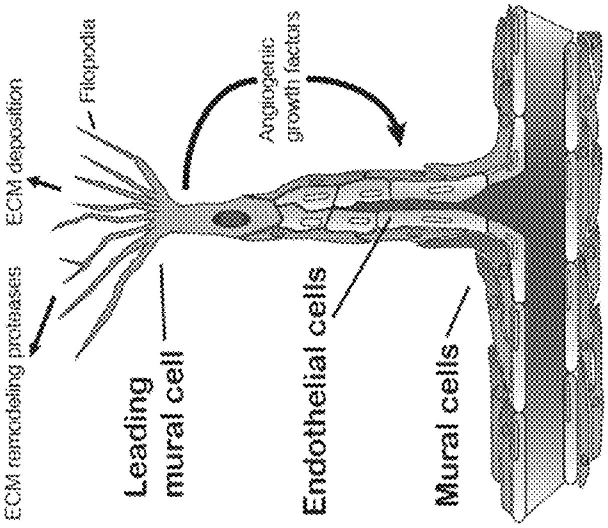
FIG. 8A is a schematic drawing showing a novel model for blood vessel formation in which MSCs lead and promote blood vessel formation in vitro

Example 7—Using MSCs to Generate a Complex Hierarchical Vascular Network from an Engineered Vessel As discussed above, data collected during the experiments described herein indicated that MSCs promote, lead, and accelerate blood vessel formation in vitro, which is a novel angiogenesis and/or vasculogenesis paradigm (FIG. 8A). Accordingly, further experiments were conducted during the development of embodiments of the technology provided herein to develop a technology for the rapid production of a perfuseable and multiscalar blood vessel network in vitro, e.g., to provide a technology for vascularizing thick engineered tissues. Furthermore, data indicated that MSC-based spherical organoids produced patent, sprouting branches; thus, experiments were conducted to generate macroscale engineered vessels comprising sprouting, patent branches. In particular, experiments were conducted to produce MSC-based cylindrical organoids (FIG. 8B).

Figure 8C:
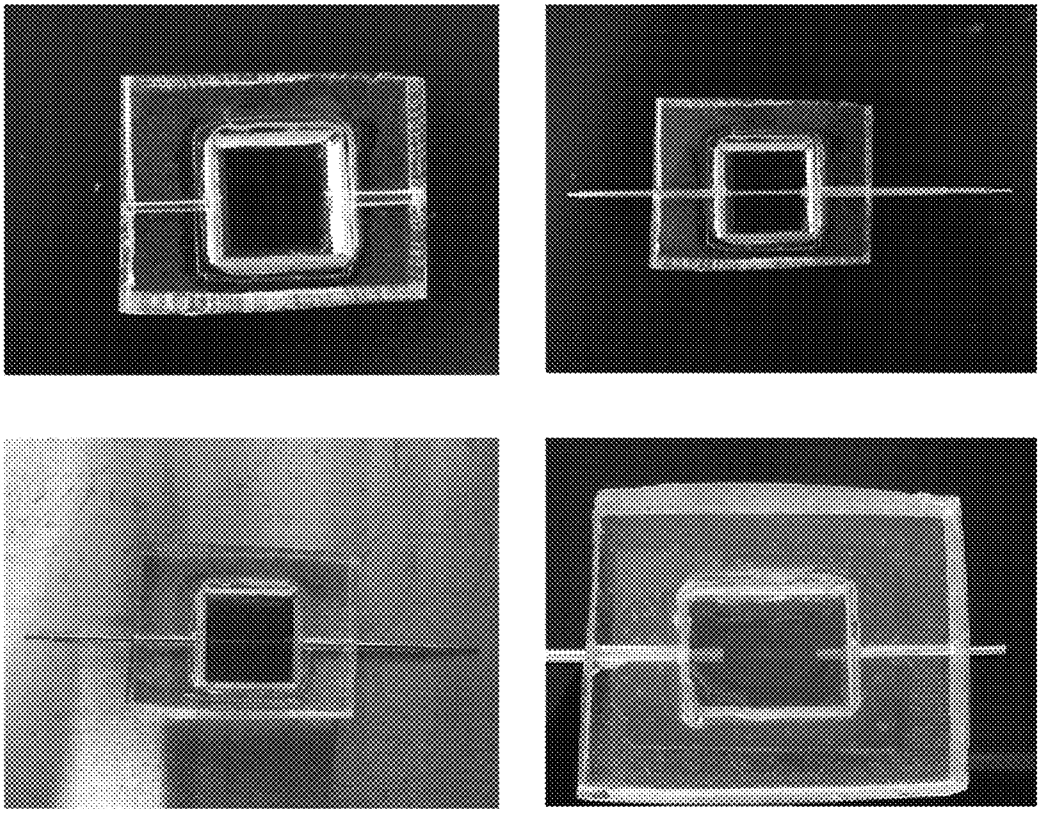
FIG. 8C shows embodiments of a tissue chamber (e.g., made from PDMS and a glass coverslip to provide for imaging) for use in the production of tubular, macroscale engineered vessels comprising patent branches. In various embodiments, different sized tissue chambers yielded different lengths of cylindrical organoids and/or engineered vessels and resulting engineered vascular networks. In various embodiments, inlet and outlet ports at opposite sides of the tissue chamber were made from hypodermic tubing of various gauges and provided access for seeding cells within the channel and for perfusion. In some embodiments, a removable, narrower gauge tube was placed through the inlet and outlet ports, and then fibrinogen and thrombin were then poured into the tissue chamber. After allowing for the formation of fibrin gel, the narrow gauge tube was removed to produce a channel within the fibrin gel.

In these experiments, tissue chambers were constructed from polydimethylsiloxane (PDMS). The tissue chambers comprised a glass coverslip as the bottom to allow for imaging (FIG. 8C). Differently sized tissue chambers yielded different lengths of engineered vessels, cylindrical organoids, and resulting engineered vascular networks.

Inlet and outlet ports at opposite sides of the tissue chamber were made from hypodermic tubing of various gauges and provided for seeding cells within the chamber and for perfusion in later experiments. A removable, narrower gauge tube was then placed through the inlet and outlet ports. Components of the tissue chamber were sterilized by autoclave. Fibrinogen and thrombin were then poured into the tissue chamber. After allowing for the formation of fibrin gel, the narrow gauge tube was removed, thereby creating a channel within the fibrin gel from the inlet port to the outlet port.

Cylindrical organoids were then generated by placing ECs, MSCs, or MSCs+ECs into this channel. Cells were seeded at an appropriate density that was low enough to prevent clogging of the inlet and outlet ports, but high enough to span the entire length of the channel sufficiently (e.g., 100,000 to 400,000 cells per centimeter of channel). After producing the solid cylindrical organoids, data were collected that indicated the presence of the angiogenic and/or vasculogenic phenomena that had been previously observed in the spherical organoids: (1) branch formation, (2) lumen formation, (3) increase in angiogenic gene expression, and (4) increase in lumen forming gene expression.

Figure 9A:
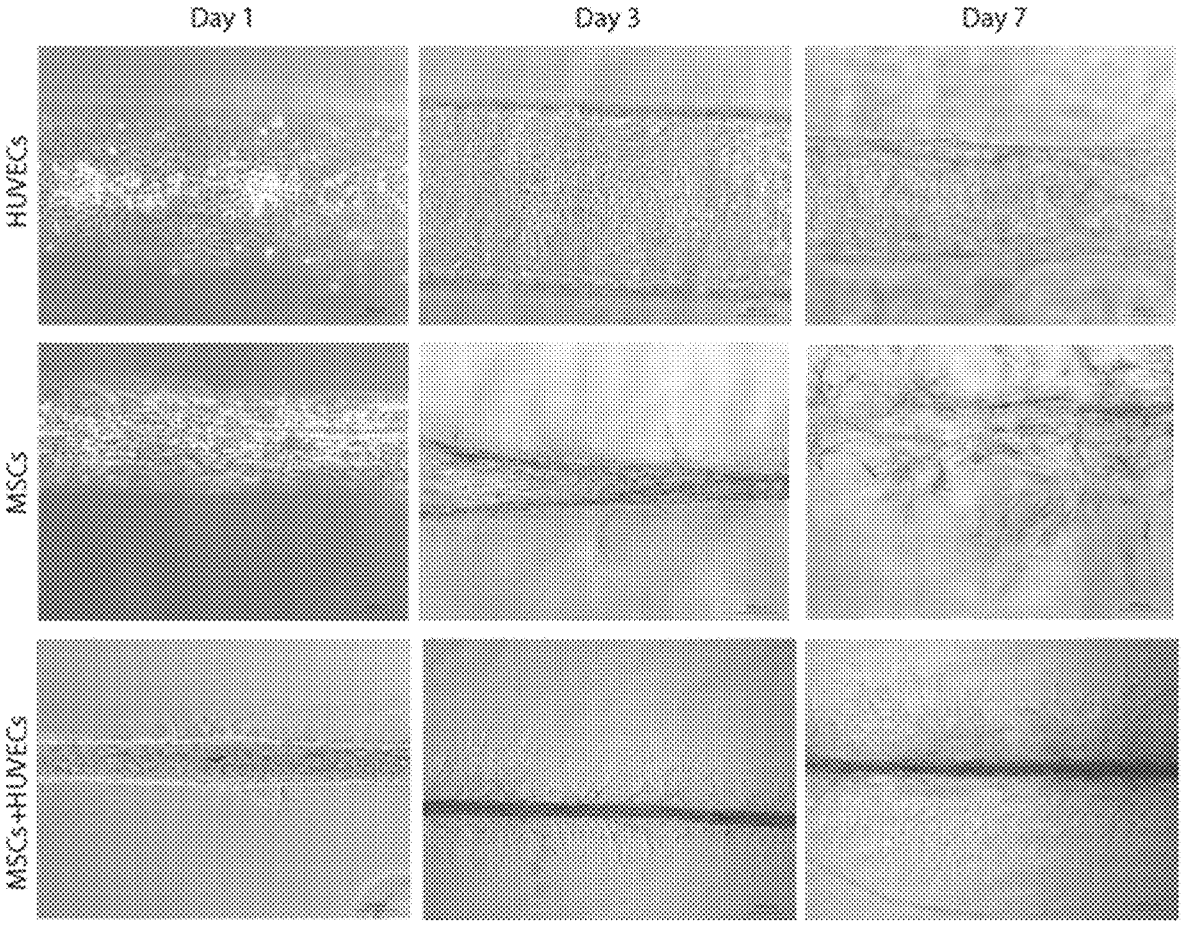
FIG. 9A shows a series of cylindrical organoids produced by placing ECs, MSCs, or a combination of MSCs+ECs into the tissue channel described in FIG. 8C. The EC cylindrical organoids manifested initial filopodia-like projections but no significant tubules had formed by the end of one week. The MSC cylindrical organoids manifested branching formation behavior much different from EC cylindrical organoids. The MSC cylindrical organoids manifested rapid and complex branching that were evident as early as day 3. These branches progressively lengthened and branched into a hierarchical network that resembled native vascular networks. By day 7, the sprouts had increased in length but the density of the cells in the central channel had decreased, suggesting that collective cell migration had occurred. Cylindrical organoids comprising a combination of MSCs and ECs manifested sprouting as early as day 1. By day 4, sprouts had increased in length extending nearly 400 micrometers from the surface of the cylindrical organoid. By day 7, sprouts had become more dense and complex and extended over 600 micrometers from the cylindrical organoid.

Over the following week of static (non-perfused) culture, EC-only cylindrical organoids that were initially solid developed thin, single cell-lined walls coating the channel. The ECs in these engineered vessels appeared to have a cobblestone pattern as seen in quiescent native vessels (see, e.g., 34). These EC-based cylindrical organoids manifested initial filopodia-like projections but no significant tubules had formed by the end of a one-week incubation (FIG. 9A). This mirrored the behavior of spherical organoids containing ECs only.

Cylindrical organoids comprising MSCs manifested branch forming behavior different that the branches formed from EC-based cylindrical organoids. In particular, the MSC cylindrical organoids rapid formed complex branching that was evident as early as day 3. These branches progressively lengthened and branched into a hierarchical network that was resembled closely native vascular networks. By day 7, the sprouts had increased in length but the density of the cells in the central channel had decreased, suggesting that collective cell migration had occurred (FIG. 9A).

Cylindrical organoids that contained both MSCs and ECs manifested sprouting as early as day 1. By day 4, sprouts increased in length and extended nearly 400 micrometers from the surface of the cylindrical organoid. By day 7, sprouts had become more dense and complex and extended over 600 micrometers from the cylindrical organoid (FIG. 9A).

Figure 9B:
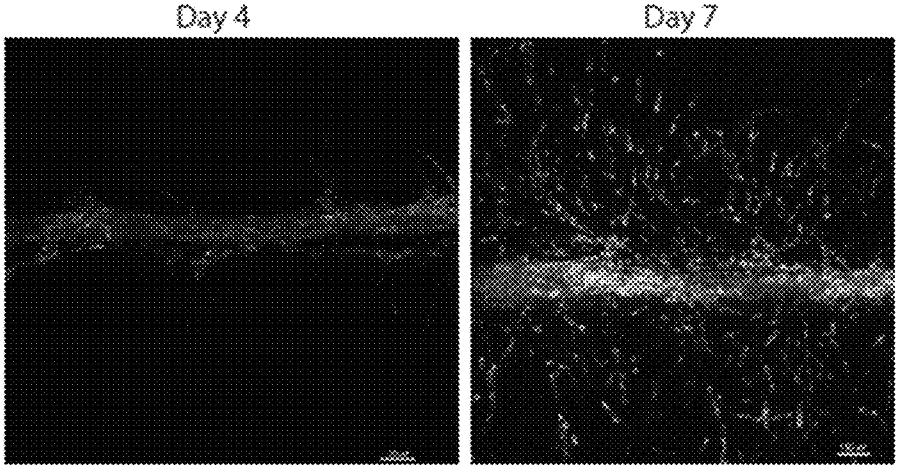
FIG. 9B shows dye tracking studies of ECs and MSCs labeled with vital dyes. The images indicated that MSCs led the sprouts from the cylindrical organoids with ECs trailing in the base of the stalk portion of the sprout.

During the development of embodiments of the technology provided herein, further experiments were conducted to determine the cellular composition of the sprouts. In particular, ECs and MSCs were labeled with vital dye. These tracking studies yielded data that indicated the same phenomena were occurring as in the sprouting spherical organoids: MSCs led the sprouts from the cylindrical organoids with ECs trailing in the base of the stalk portion of the sprout (FIG. 9B).

Example 8—Cylindrical Organoids with Smooth Muscle Cells

Figure 10A:
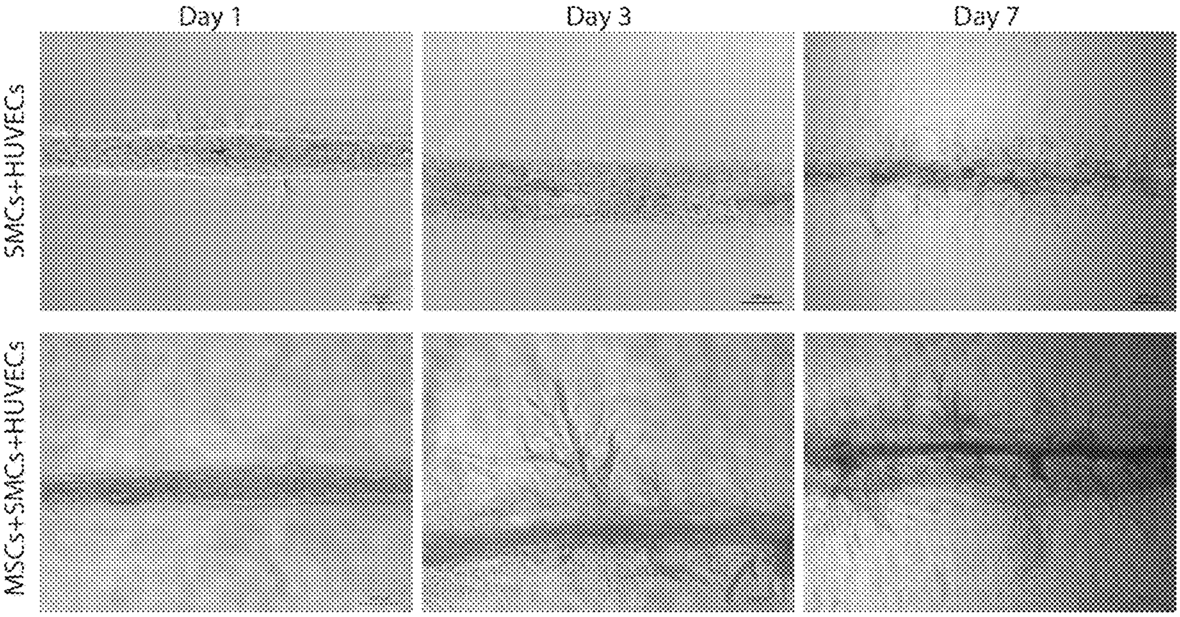
FIG. 10A shows microscope images indicating that cylindrical organoids comprising a combination of ECs and smooth muscle cells (SMCs) yielded sprouts that were of larger caliber and less dense than sprouts produced from organoids comprising a combination of MSCs and ECs.
Figure 10B:
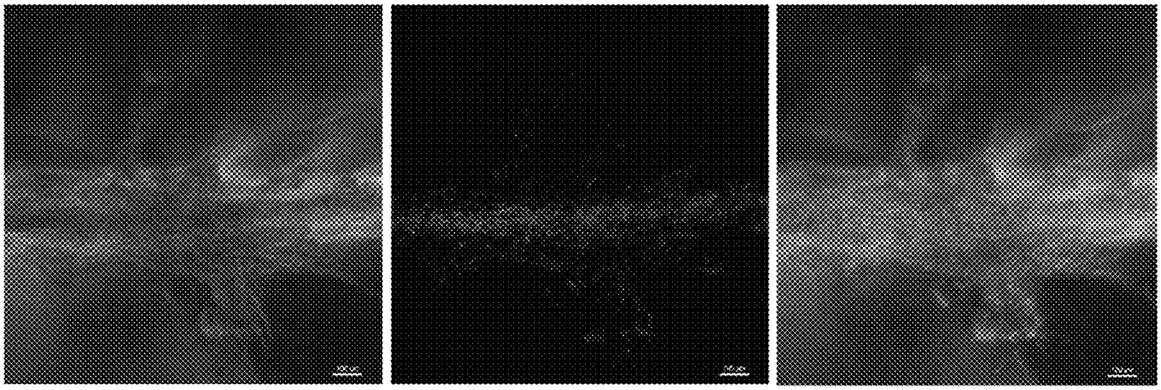
FIG. 10C shows microscope images of cylindrical organoids comprising a combination of SMCs, MSCs, and ECs (e.g., in a 1:1:1 ratio). This triple-cell combination construct produced a vascular network that comprised both large and small caliber sprouts and that was less dense and not as expansive as vascular networks emanating from MSC+EC cylindrical organoids (see FIG. 10A). Tracking experiments demonstrated that both SMCs and MSCs were present in the sprouts emanating from triple-cell cylindrical organoids and that MSCs were present at the tips of most sprouts.

Native vessels of larger caliber contain vascular smooth muscle cells (SMCs). Thus, further experiments were conducted during the development of embodiments of the technology provided herein to assess the effect of adding SMCs to cylindrical organoids that contained ECs and MSCs. In the experiments, cylindrical organoids comprising ECs+SMCs yielded sprouts. The sprouts had a larger diameter and were less dense than sprouts produced by organoids containing MSCs+ECs (FIG. 10A). Vascular networks produced by SMC+EC cylindrical organoids were also shorter than those created by MSCs+ECs. Experiments were conducted to determine the cellular composition of the sprouts by tracking the cells of the sprouts with vital dyes. Data from these experiments indicated that sprouts comprised SMCs and were led by the SMCs (FIG. 10B).

Figure 10C:
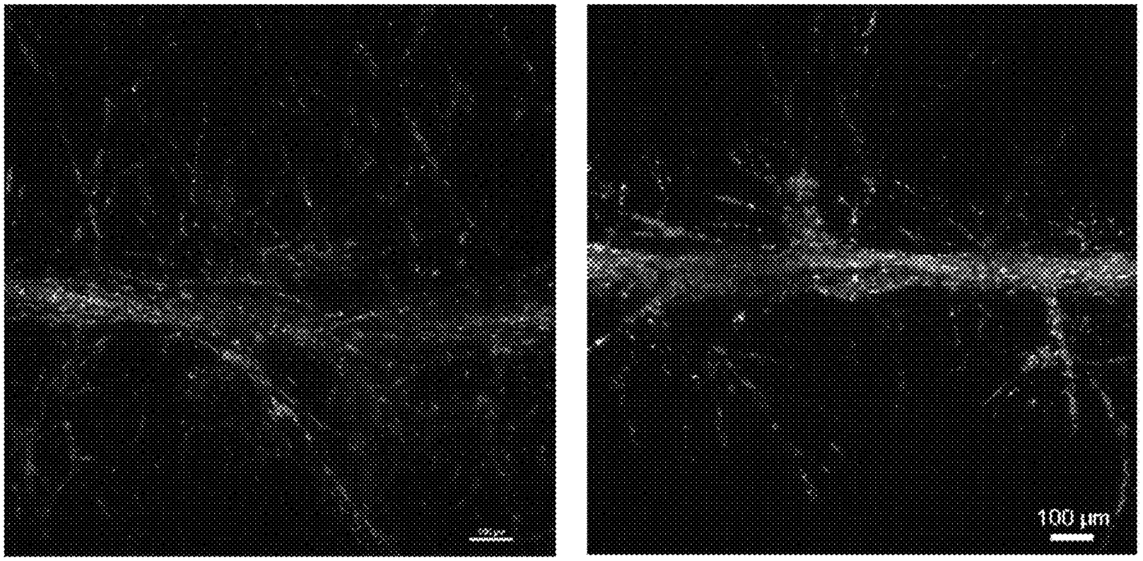

In additional experiments, cylindrical organoids were produced with SMCs, MSCs, and ECs (in a 1:1:1 ratio). This triple cell combination construct produced a vascular network that contained both large and small diameter sprouts and that was less dense and less expansive than the vascular networks emanating from MSC+EC cylindrical organoids (FIG. 10A). Tracking experiments indicated that both SMCs and MSCs were present in the sprouts emanating from triple cell cylindrical organoids and that MSCs were present at the tips of most sprouts (FIG. 10C). These data indicate that the technology provides for engineering complex and expansive vascular networks from cylindrical organoids that contain MSCs (or SMCs) and ECs.

Figure 11D:
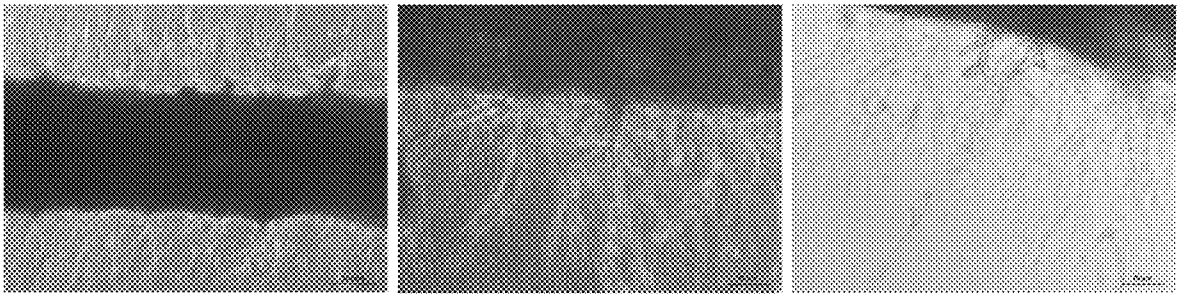
FIG. 11D shows microscope images indicating that engineered vessel and the emanating vascular network can be perfused with human red blood cells and appear like perfused native vascular networks. These experiments demonstrated the patency of the engineered vessels and their emanating branches.

Example 9—Lumen Formation in MSC-Based and SMC-Based Cylindrical Organoids—Patent Engineered Vascular Networks Accordingly, further experiments were conducted during the development of embodiments of the present technology to evaluate the patency of the components of the vascular networks and thus the ability of the networks to transport fluid. In particular, patency of the main channels of the cylindrical organoids containing MSCs+ECs was assessed by injecting saline into the inlet ports at day 3, 7, and 14 and observing the passage of saline through the outlet port (FIG. 11A). Cylindrical organoids comprising MSCs were generally patent; constructs comprising SMCs generally were not patent. Cylindrical organoids comprising umbilical artery (UA) SMCs+ECs were uniformly not patent and forced perfusion of these constructs resulted in fluid flowing around the solid cord of cells (FIG. 11A). On the other hand, cylindrical organoids comprising coronary vascular SMCs+ECs were patent.

Experiments were then conducted to confirm the patency of the main channel (engineered vessel) and the emanating vascular network. In particular, cylindrical organoids were perfused with microspheres or human red blood cells and evaluated by visual inspection (FIG. 11). Inspection of the engineered vessels unequivocally indicated the patency of the engineered vessels and their emanating branches. Engineered vascular networks were also subjected to perfusion with human red blood cells (RBCs), which yielded identical results to the microsphere perfusion experiments (FIG. 11C).

Example 10—Angiogenic Gene Expression in Engineered Vascular Networks

Figure 12:
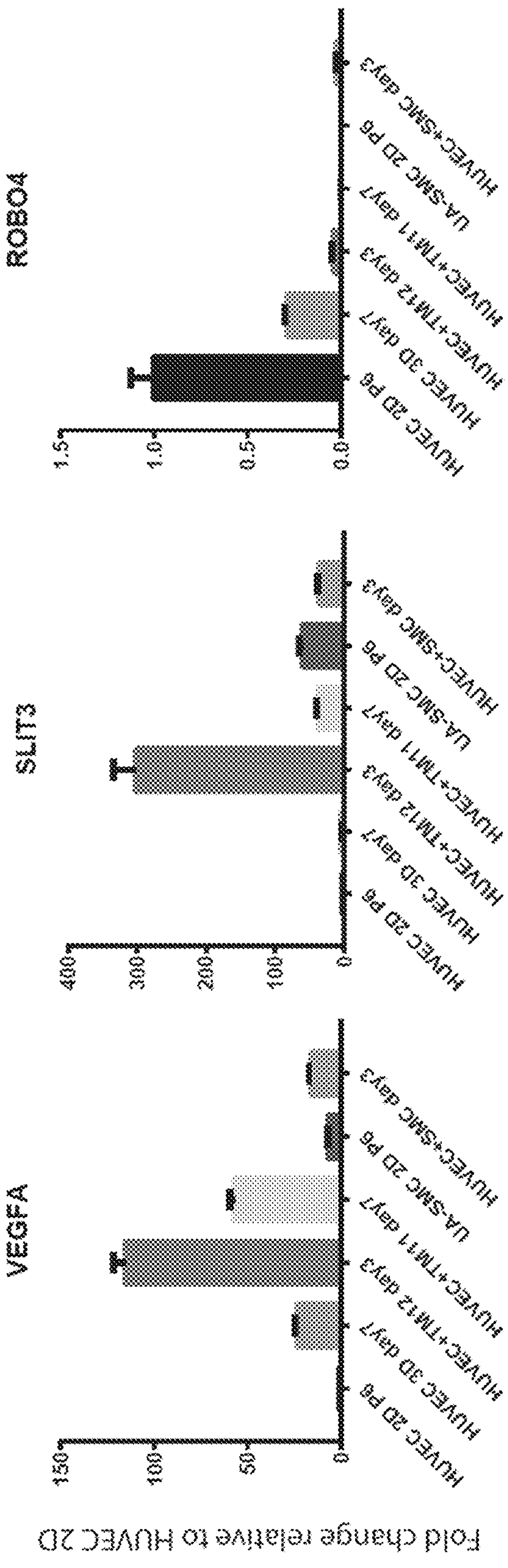
FIG. 12 is a series of bar plots showing that the expression of angiogenic genes (e.g., VEGFA and SLIT3) was increased in cylindrical organoids as determined by qPCR. Constructs comprising a combination of MSCs and ECs had the greatest expression of VEGFA and SLIT3, while constructs with only ECs had the highest expression of ROBO4, which encodes for the cognate receptor of SLIT3. "TM11" and "TM12" are individual thymus MSC lines isolated from discarded thymus tissue.

Experiments conducted during the development of embodiments of the technology provided herein were conducted to measure the expression of genes associated with angiogenesis in organoids. In particular, angiogenic gene expression was determined qPCR. Data collected indicated that VEGFA and SLIT3 was upregulated in cylindrical organoids (FIG. 12). Analysis of temporal expression patterns indicated that expression of these genes was highest early in the study and had tapered by 7 days. The greatest expression of VEGFA and SLIT3 was measured in engineered vascular constructs comprising both MSCs and ECs. Constructs comprising only ECs had the highest expression of ROBO4, which encodes for the cognate receptor of SLIT3.

Example 11—Sprouting and Patency of MSC-Based Engineered Vascular Networks are Independent of Formin Activity Recent work has shown that blood vessel lumen formation requires the presence of ECs and the activity of formins (see, e.g., 35). Formins regulate both actin and microtubule stabilization that promotes blood vessel morphogenesis. Thus, experiments were conducted during the development of embodiments of the technology provided herein to evaluate the role of formin activity for sprout formation in MSC-based engineered vascular networks. In particular, experiments were conducted in which cylindrical organoids were exposed to SMIFH2, a broad formin inhibitor (36). Data collected during these experiments indicated that SMIFH2 did not significantly affect engineered vascular network formation, indicating that formin activity is not central for the sprouting response in MSC+EC cylindrical organoids (FIG. 13A). In addition, experiments successfully perfused microbeads through SMIFH2-treated MSC+EC engineered vascular networks, which indicated that lumen formation in engineered vascular networks is not dependent on formin activity (FIG. 13B).

In experiments described above, data were collected that indicated that cylindrical organoids produced from UASMCs+ECs were not patent and those comprising MSCs+ECs were patent and perfusable. Furthermore, gene expression analysis of UASMCs and thymus MSCs in both two-dimensional and spherical organoid form indicated that MSCs expressed genes associated with lumen formation at a higher level than UASMCs (FIG. 13C).

Figure 14A:
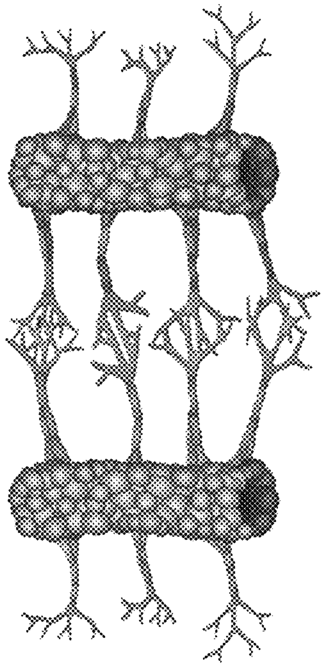
FIG. 14A shows a model of an embodiment of the technology provided herein, e.g., a vascular bed comprising a feeding artery, intervening arterioles, capillaries, venules, and a draining vein. The technology provided herein provides methods for producing a complete, multiscalar and multiphenotype vascular network comprising, e.g., an arterial EC+MSC based cylindrical organoid adjacent to a venous EC+MSC based cylindrical organoid. Embodiments of the technology provide an arterial EC+MSC based cylindrical organoid adjacent to a venous EC+MSC based cylindrical organoid and in which the emanating branches of the arterial organoid anastomose with the emanating branches of the venous organoid.

Example 12—Complete Engineered Vascular Network and Effects of Hydrostatic Pressure A vascular bed comprises, e.g., a feeding artery, intervening arterioles, capillaries, venules, and a draining vein. During the development of embodiments of the technology described herein, experiments were conducted to generate a complete, multiscalar, and multiphenotype vascular network, e.g., comprising these components. In particular, experiments were conducted in which arterial EC+MSC-based cylindrical organoids were placed adjacent to venous EC+MSC-based cylindrical organoids and anastomosis of emanating branches from one organoid to the other organoid was evaluated (FIG. 14A).

Figure 14B:
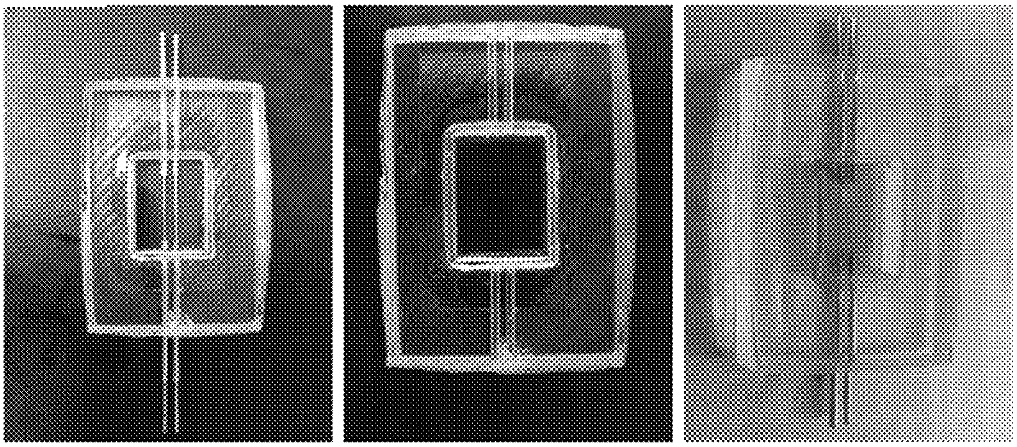
FIG. 14B shows images of embodiments of a tissue chamber for producing two parallel cylindrical organoids separated by a distance of approximately more than 1 mm.
Figure 14C:
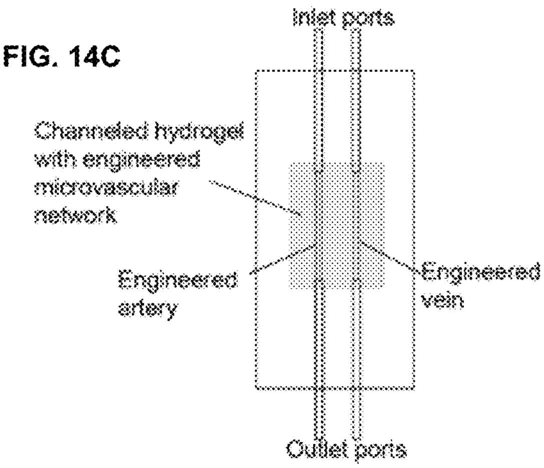
FIG. 14C shows a drawing of an embodiment of a tissue chamber comprising a cylindrical organoids produced from MSCs+HUAECs and another cylindrical organoid comprising MSCs+HUVECs to yield an engineered artery and engineered vein and an intervening microvascular network.
Figure 14D:
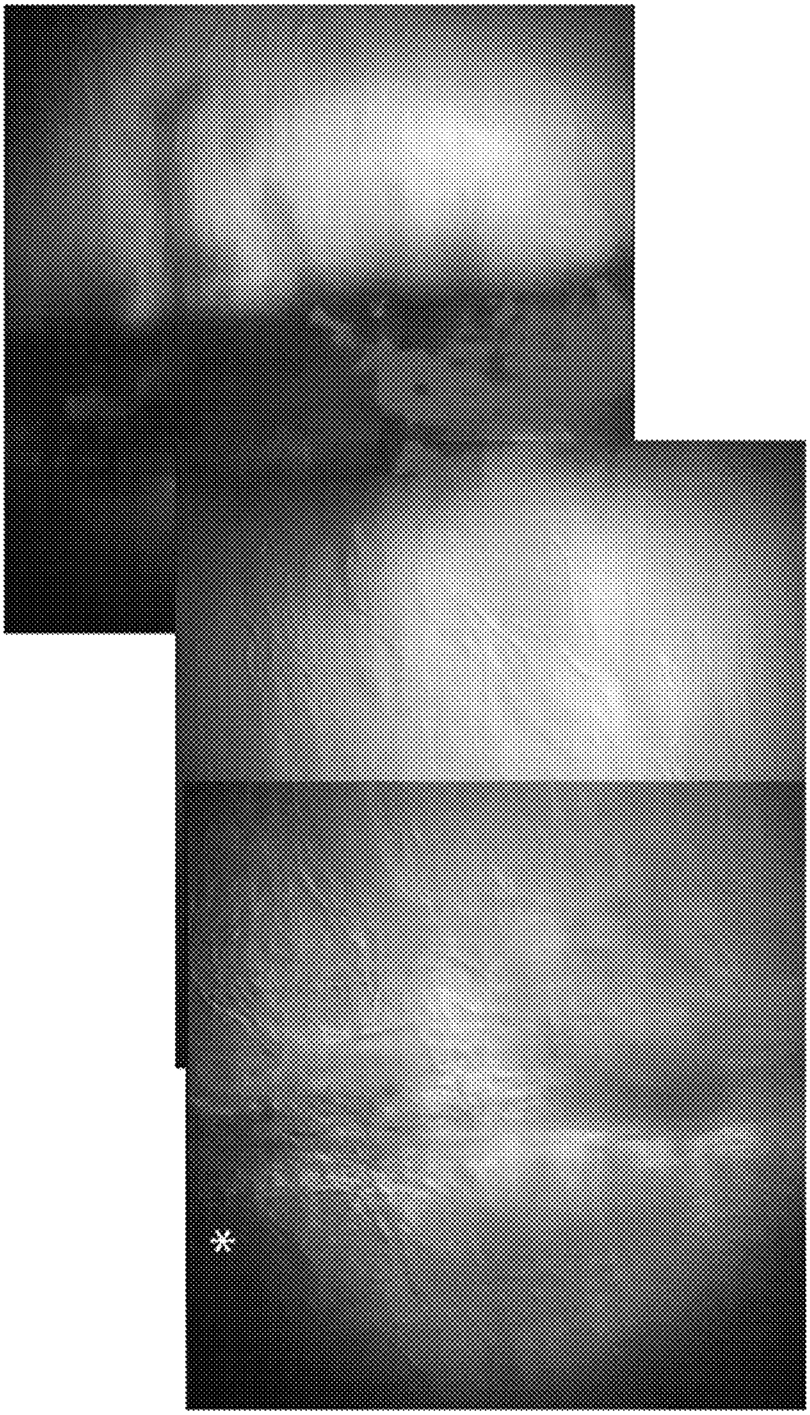
FIG. 14D shows a composite microscope image showing perfusion of the arterial engineered vessel with microspheres and flow of the microspheres within the lumens of branches and in the venous engineered vessel. The microspheres in the engineered vein are indicated by the asterisk. The image is a confocal fluorescent image with brightfield overlay after infusion of fluorescent microspheres (1 μm diameter) into the engineered artery (top of image). Microspheres fill the lumen of the engineered artery and its branches (arterioles and capillaries) and eventually reside within the lumen of the engineered vein.

Data were collected by modifying the tissue chamber described above to provide for the generation of two parallel cylindrical organoids separated by a distance of at least 1 mm (FIGS. 14B and 14C). One cylindrical organoid comprised MSCs+HUAECs (human umbilical artery endothelial cells) and the other cylindrical organoid comprised MSCs+HUVECs (human umbilical vein endothelial cells) to yield an engineered artery and vein with an intervening microvascular network. The branch density was sufficiently high and created a high degree of light scattering that prohibited attempts to visualize anastomotic connections between the two emanating engineered vascular networks. Therefore, a functional approach was used to identify anastomoses. In particular, arterial engineered vessels were perfused with microspheres and it was observed that that these microspheres became present within the lumens of branches and in the venous engineered vessel (FIG. 14D). In FIG. 14D, images were stitched together to visualized the perfused engineered artery (top) and the appearance of blue microspheres in the engineered vein (bottom, indicated by asterisk). Accordingly, these data indicated the existence of anastomosing networks between the adjacent engineered vessels.

Figure 14E:
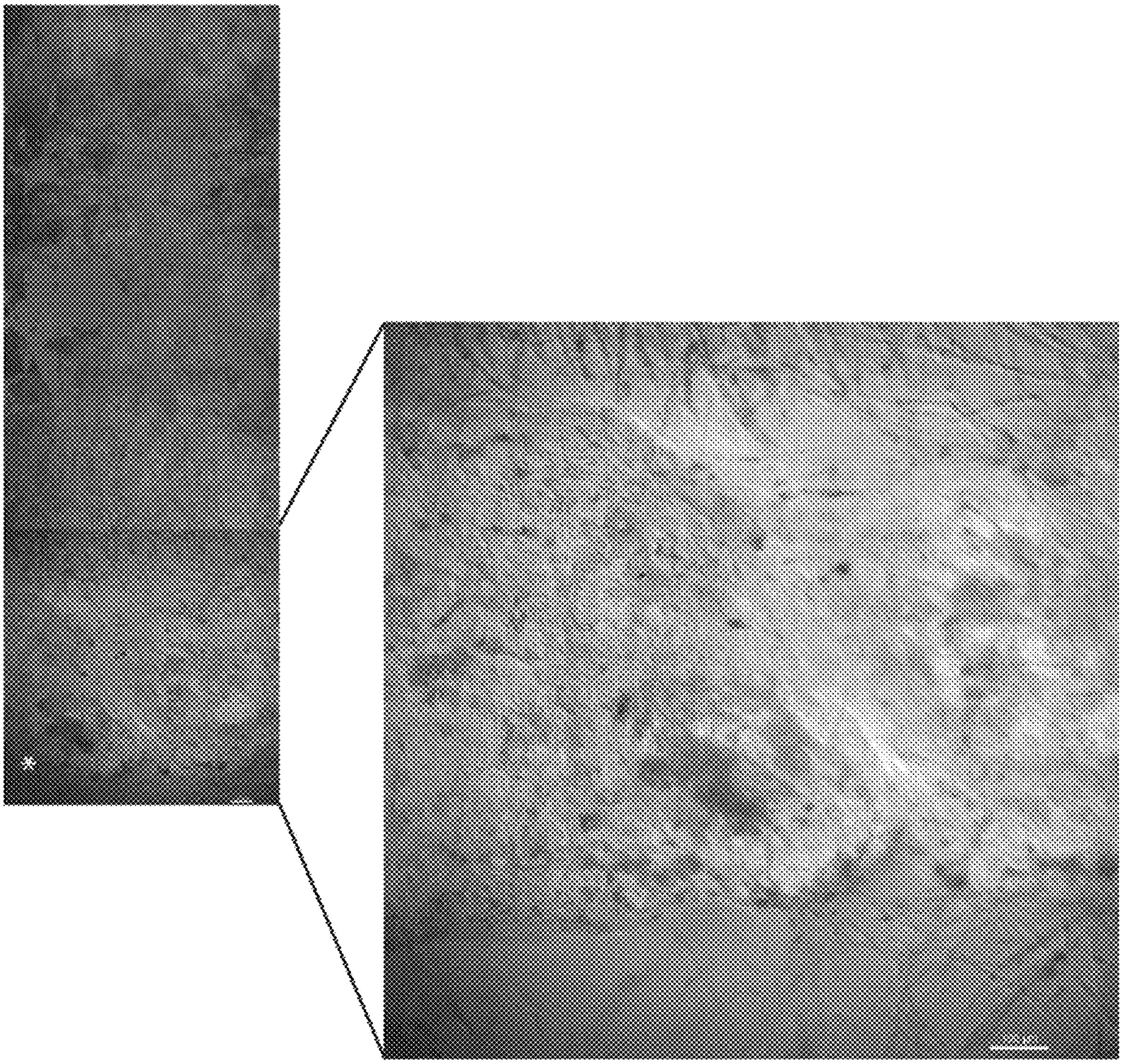
FIG. 14E shows a composite microscope image showing perfusion of a dual vascular construct comprising engineered vessels separated by 2 mm. The engineered artery was perfused with microspheres under a hydrostatic pressure (5 cm $H_2O$). The hydrostatic pressure improved the flow of microspheres into the small branches of the engineered artery: in particular, more microspheres appeared within the engineered vein than in the absence of pressure. Magnification of the engineered vein clearly demonstrated the presence of blue microspheres.
Figure 14F:
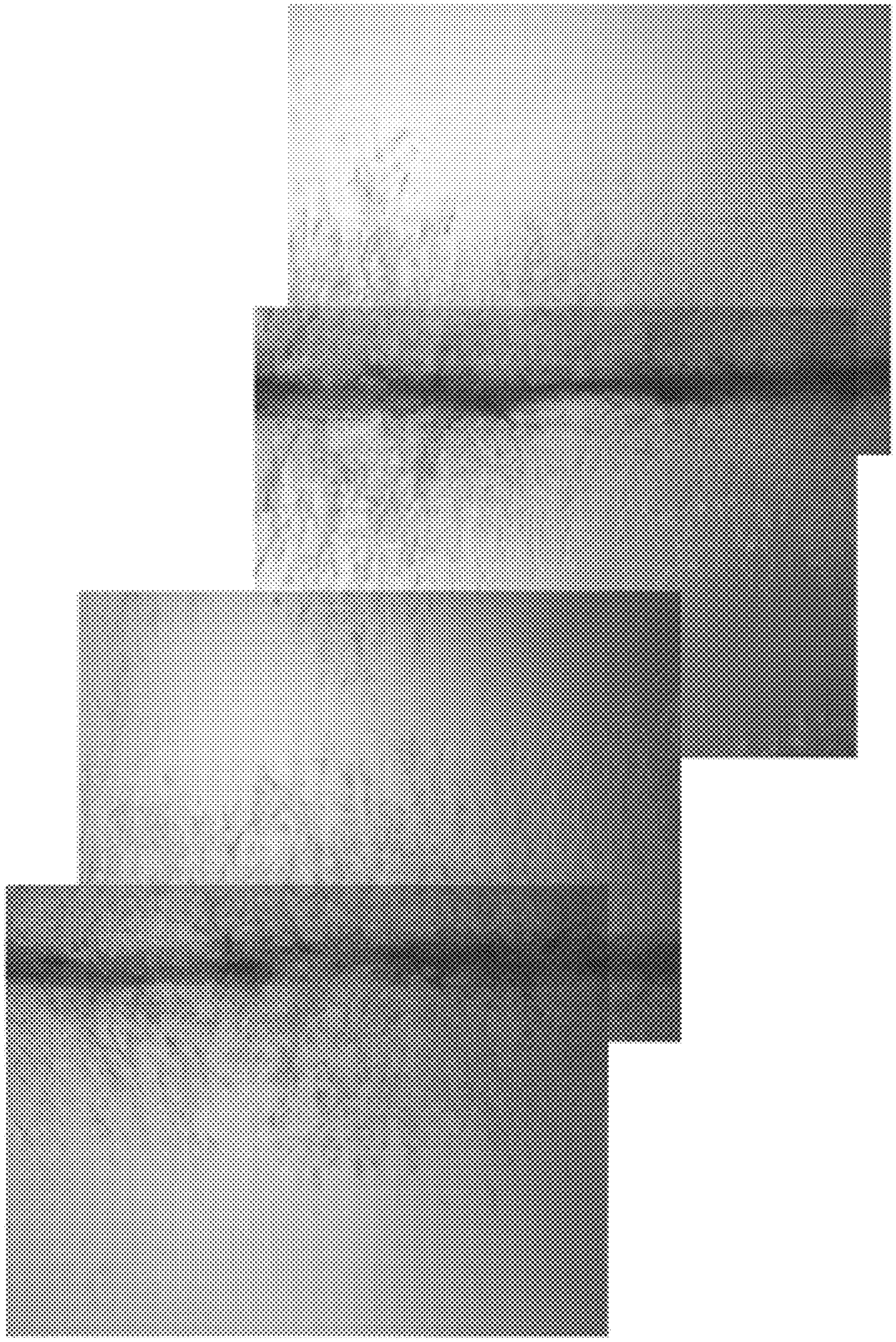
FIG. 14F shows images from the fabrication of a comprehensive, perfuseable vascular network. The microscope images show an engineered artery made from thymus MSCs and HUAECs located at the top and an engineered vein made from thymus MSCs and HUVECs is located at the bottom. Sprouting is evident from both engineered vessels.

In further experiments using a dual vascular construct comprising engineered vessels separated by 2 mm, the engineered artery was connected to a fluid column containing blue microspheres and a hydrostatic pressure of 5 cm $H_2O$. Data collected indicated that the hydrostatic pressure improved the flow of microspheres into the small branches of the engineered artery with more of them appearing within the engineered vein (FIG. 14E). Magnification of the engineered vein clearly indicated the presence of blue microspheres.

Example 13—Presence of Basement Membrane in MSC-Based Engineered Vessels

Figure 15:
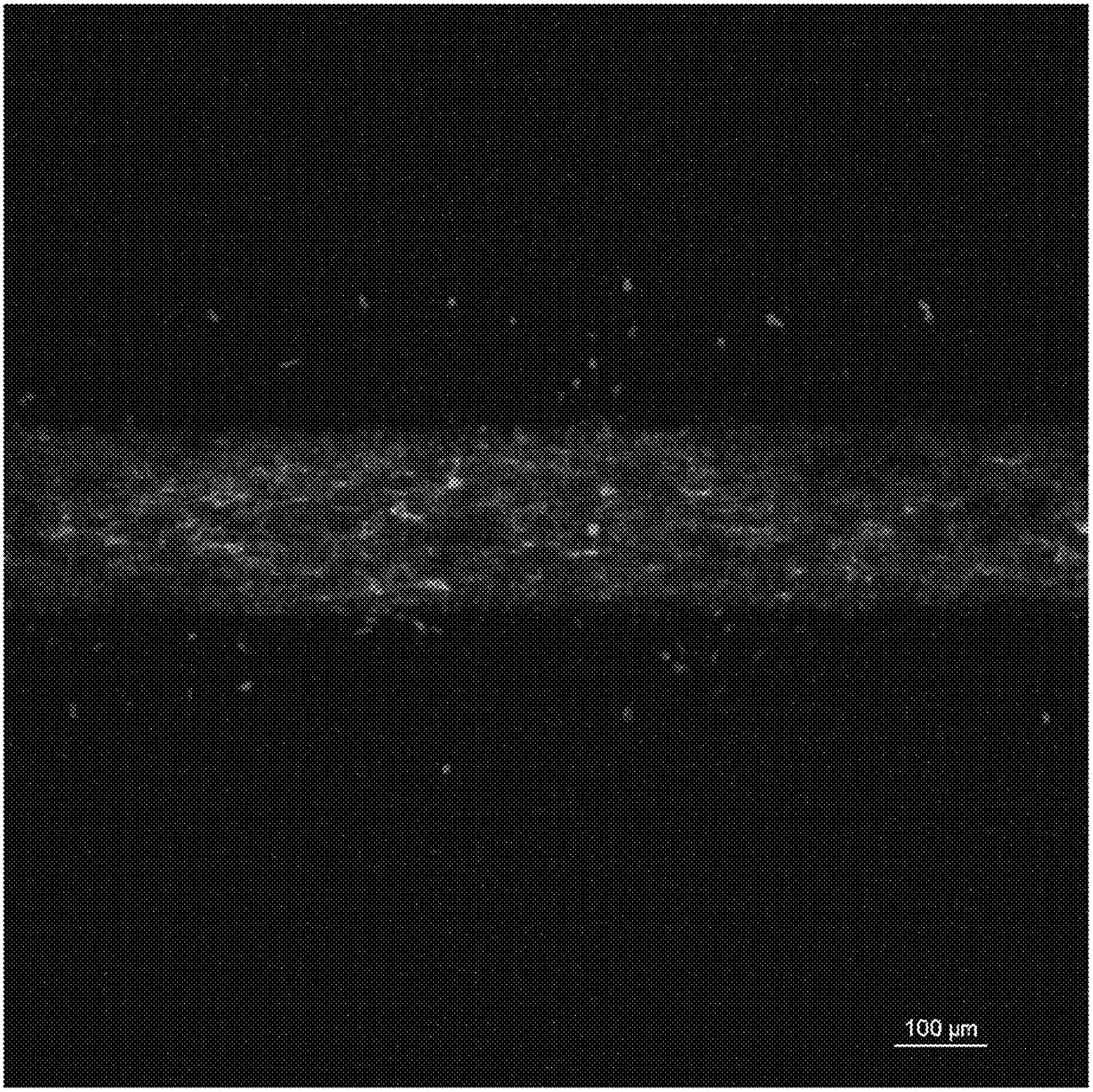
FIG. 15 shows an image of immunofluorescence staining indicating that MSC+EC engineered vessels expressed type IV collagen. The expression of type IV collagen was greatest in the central lumen of the cylindrical organoid with most of the cells (MSCs) on the abluminal side. No expression of either laminin or type IV collagen was identified in the sprouts emanating from the cylindrical organoid.

Native blood vessels are characterized by the presence of a basement membrane, of which laminin and type IV collagen are major components (see, e.g., 37, 38). Accordingly, experiments were conducted during the development of embodiments of the technology provided herein to determine if engineered vessels comprise a basement membrane. In particular, immunofluorescent staining was used to visualize MSC+EC based constructs. Data collected during the experiments indicated that MSC+EC engineered vessels lacked laminin expression but did express type IV collagen (FIG. 15). The expression of Type IV collagen was greatest in the central lumen of the cylindrical organoid with most of the cells (MSCs) on the abluminal side. No expression of either laminin or Type IV collagen was identified in the sprouts emanating from the cylindrical organoid.

Example 14—Four-Dimensional Bioprinting of Vasculature in Engineered Tissues

Three-dimensional (3D) bioprinting technologies have recently provided an improvement in creating branched vascular networks on the smaller end of the macroscopic scale and larger end of the mesoscopic scale. (see, e.g., Rouwkema & Khademhosseini (2016) "Vascularization and Angiogenesis in Tissue Engineering: Beyond Creating Static Networks" *Trends Biotechnol* 34: 733-745; Datta et al (2017) "Bioprinting for vascular and vascularized tissue biofabrication" *Acta Biomater* 51: 1-20). In some extant technologies, sacrificial substrates are 3D printed into the shape of vascular networks within a broader hydrogel structure. (see, e.g., Kolesky et al (2016) "Three-dimensional bioprinting of thick vascularized tissues" *Proc Natl Acad Sci USA* 113: 3179-3184). The sacrificial substrate is dissolved and the remaining channel network is seeded with ECs. Alternatively, in some technologies the sacrificial substrate takes the form of a fugitive ink containing cells that are then left behind as the fugitive ink liquefies (see, e.g., Lee et al. (2014) "Creating perfused functional vascular channels using 3D bio-printing technology" *Biomaterials* 35: 8092-8102). Another approach involves the direct ink writing (DIW) of bioink comprising vascular cell-containing spherical organoids in the form of vascular networks (see, e.g., Norotte et al. (2009) "Scaffold-free vascular tissue engineering using bioprinting" *Biomaterials* 30: 5910-5917). Three-dimensional bioprinting also permits the printing of adjacent parenchymal cells, thus yielding vascularized engineered tissue.

However, bioprinting of smaller (e.g., mesoscopic (e.g., approximately 20-100 μm diameter) and microscopic (approximately <20 μm diameter)) vessels represents a key challenge because of the limitations associated with print resolution (see, e.g., Datta, supra; Gauvin & Khademhosseini (2011) "Microscale technologies and modular approaches for tissue engineering: moving toward the fabrication of complex functional structures" *ACS Nano* 5: 4258-4264). Even if 3D bioprinters could achieve a resolution <5 μm, printing a patent microvasculature would meet physical, biological, and technical limitations. In particular, capillaries are made of single cells that are in a tubular form and 3D bioprinters can only deposit cells in a defined location without control of cellular morphology.

In contrast, a promising strategy for creating engineered branched vascular networks at relevant biological scales (e.g., the smaller end of the macroscopic scale and larger end of the mesoscopic scale) is "four-dimensional" (4D) bioprinting, where the time parameter is the 4th dimension (see, e.g., Li et al. (2016) "4D bioprinting: the next-generation technology for biofabrication enabled by stimuli-responsive materials" *Biofabrication* 9: 012001; Gao et al. (2016) "4D Bioprinting for Biomedical Applications" *Trends Biotechnol* 34: 746-756). In this strategy for producing an engineered vascular system, vascular cells are 3D printed into larger vascular structures and then conditions are provided under which the 3D printed structures undergo morphological changes (e.g., shape formation) to generate a sprouting mesoscopic and microscopic vascular network (see, e.g., Lee et al., supra).

A foundational technology that supports these nascent 4D bioprinting approaches comprises developing a culture environment and associated conditions in which the bioprinted vascular cells create pervasive networks that are dense and subtend large domains. Angiogenic/vasculogenic phenomena appropriate for producing engineered vasculature occur under specific controlled conditions. Conventional approaches to achieving angiogenesis by EC self-organization in vitro do not provide the proper growth environment and produce resultant networks that are inadequate because they are too simple and limited in domain.

As indicated by the results of experiments conducted during the development of embodiments of the technology described herein, human VMC (e.g., SMCs and MSCs) organoids manifest vasculogenic and angiogenic behavior in fibrin gel in vitro and sprouting behavior of VMCs is stimulated by high cell density in 3D culture and is associated with the activation of specific gene networks that are independent of EC transdifferentiation. Further, results of experiments conducted during the development of embodiments of the technology described herein indicated that cylindrical organoids (e.g., of 200 to 400 μm diameters) were produced from ECs, VMCs, or VMCs+ECs in vitro according to embodiments of the technology provided herein. In some embodiments, the technology provides a custom perfusion bioreactor (e.g., providing control of, e.g., temperature, oxygen tension, etc.) in which engineered vascular networks described herein are provided with continuous or pulsatile flow (e.g., for times of at least 14 days, e.g., for times of at least 30 days).

In sum, the data collected during experiments described herein indicate that VMCs drive mesoscopic and microscopic network formation in a natural scaffold (e.g., fibrin gel) in vitro. Further, the formation of the mesoscopic and microscopic network is independent of, and augmented by, ECs. And, even further, in some embodiments these mesoscopic and microscopic networks extend over mm-scale distances (e.g., 0.5 mm to 10 mm (e.g., 0.5, 1, 2, 3, 4, 5, 6, 7, 8, 9, 10 mm)). Further, experiments conducted during the development of embodiments of the technology described herein have defined several cellular and molecular mechanisms that influence the magnitude and extent of VMC-driven network formation. Specifically, data collected during these experiments have established that macroscopic linear structures made from VMCs yield complex perfusable branching networks over mm-scale domains that have been previously unattainable by conventional EC-based approaches.

Figure 26B:
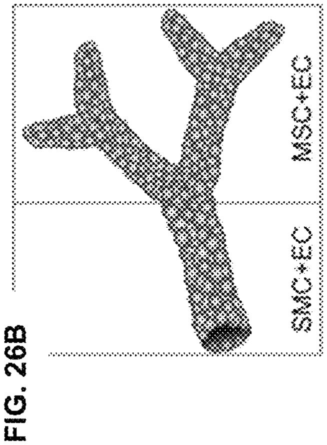
FIG. 26B shows direct ink writing of cells to create cellular heterogeneity throughout the branching structure. The main ("mother") part of the vascular structure is printed with SMCs+ECs and the daughter channels are printed with MSCs+ECs because MSCs drive the formation of the microscopic vascular networks as described herein.
Figure 26A:
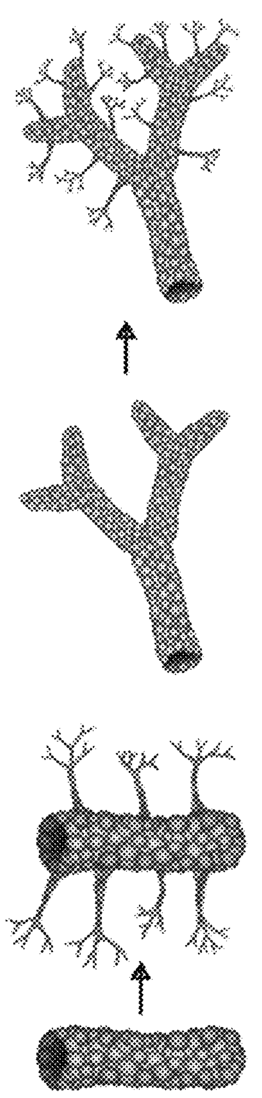
FIG. 26A shows 3D bioprinting branching macroscopic and mesoscopic VMC-based vascular structures and allowing the vascular mural cells (VMCs) to drive sprouting over time (4th dimension).
Figure 26C:
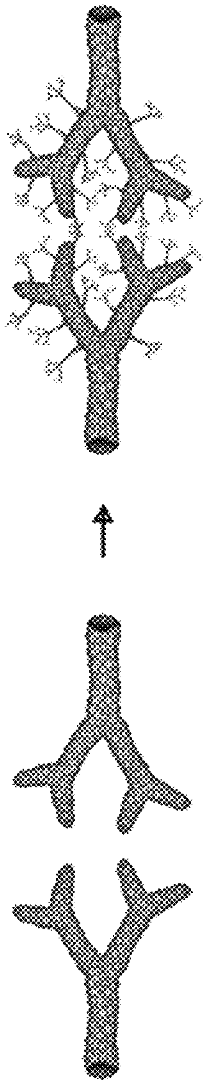
FIG. 26C shows the formation of a complete vascular network using 4D bioprinting of diametrically opposed branched vascular structures and permitting anastomosis/fusion between the two emanating microscopic networks. In some embodiments, this complete vascular network is perfused and serves as an engineered epicardium for cardiomyocytes to be seeded on the surface of the perfused vasculature.

Accordingly, in some embodiments the technology comprises use of VMCs or VMCs+ECs (e.g., in a 1:1 ratio, e.g., in a ratio ranging from 0.1:1 to 1:0.1) in a bioink. Further, in some embodiments, the technology comprises use of a bioink (e.g., comprising VMCs or VMCs+ECs (e.g., in a 1:1 ratio, e.g., in a ratio ranging from 0.1:1 to 1:0.1)) for 4D bioprinting of small macroscopic and large mesoscopic (e.g., 300 μm to 1 mm diameter, e.g., 0.3, 0.4, 0.5, 0.6, 0.7, 0.8, 0.9, or 1 mm in diameter) branching vascular structures. In some embodiments, the technology comprises use of an extrusion based bioprinter (CELLINK BIO-X, 50 μm resolution). In some embodiments, larger vascular structures (e.g., as described herein) give rise to smaller mesoscopic and microscopic branches and mesh-like networks that will extend over a large domain, thus providing the potential to support a large number of parenchymal cells in engineered tissues. In some embodiments, diametrically opposed branching vascular networks anastomose with each other, thus yielding a perfusable complete multiscalar and multiphenotype vascular network (FIG. 26A to FIG. 26C).

Accordingly, in some embodiments the technology provides a fabricated (e.g., engineered) macroscopic vascular network that produces mesoscopic and microscopic networks. In some embodiments, the technology comprises use of a direct ink writing (DIW) method (e.g., comprising use of a 3D bioprinting VMC-based bioink within a hydrogel (e.g., a fibrin hydrogel)). Embodiments of the technology comprise use of a VMC-based bioink that is bioprinted and preserves the vasculogenic/angiogenic potential of the VMCs in the bioink. In some embodiments, the technology provides a perfused, complete vascular network comprising a capillary bed that supplies an area of approximately 2 $cm^2$ (e.g., 1 to 5 $cm^2$, e.g., 0.5, 1, 1.5, 2, 2.5, 3, 3.5, 4, 4.5, or 5 $cm^2$), which forms the basis of a perfused engineered epicardium. In some embodiments, the technology comprises seeding cardiomyocytes on the perfused engineered epicardium to yield vascularized engineered heart tissue.

Accordingly, embodiments of the technology provide a DIW method and bioprint ink that do not diminish (e.g., do not effectively, significantly, detectably, and/or substantially diminish) the vasculogenic/angiogenic properties of bioprinted VMCs. Further, embodiments provide a DIW method and bioprint ink that retains its shape fidelity with minimal sagging after extrusion. Accordingly, embodiments provide a bioink that does not interfere with the ability of VMCs to become activated, form patent channels, and/or to generate sprouting networks.

In some embodiments, the technology comprises use of a VMC-based bioink comprising a hydrogel (e.g., a thermoresponsive hydrogel, e.g., a nano-cellulose/alginate mixture, a gelatin, a methylcellulose, a pluronic F-127). In some embodiments, the technology comprises use of a material that is shear-thinning and/or fast crosslinking; aqueous at 37° C. and a gel at a cooler temperature; and/or aids VMC activation.

In some embodiments, hydrogel concentration and crosslinking (if needed) is tuned to maximize VMC viability and printability without compromising the vasculogenic/angiogenic properties of the VMCs. Based on data collected during the development of embodiments of the technology provided herein, some embodiments comprise use of a VMC concentration that is $10\times10^6$ cells/ml in the bioink.

In some embodiments, a hydrogel is used in a bioink. For example, in some embodiments VMC spheroids (e.g., 400 MSCs or 400 SMCs per spheroid) are produced comprising varying concentrations of hydrogel and crosslinker, which are subsequently embedded in fibrin gel. In some embodiments, cell viability is determined using a standard LIVE/DEAD assay and the degree of sprouting is measured using methods as described elsewhere herein. In some embodiments, a bioink composition is used in a 3D-printed linear channel (e.g., comprising a diameter of, e.g., 300 μm to 1 mm, e.g., 0.3, 0.4, 0.5, 0.6, 0.7, 0.8, 0.9, or 1 mm in diameter) in fibrin gel within a PDMS tissue chamber. In some embodiments, hypodermic tubing is inserted into the ends of the channel to serve as inlet/outlet ports, e.g., as described elsewhere herein. In some embodiments, the degree of sprouting and patency of the main channel and sprouting branches is measured as described herein.

In some embodiments, 3D print macroscopic structures are formed with one, two, or more generations of smaller-caliber daughter branches designed according to the fractal rules of vascular branching (see, e.g., Glenny (2011) "Emergence of matched airway and vascular trees from fractal rules" *J Appl Physiol* (1985) 110: 1119-1129). In some embodiments, a main ("mother") channel is 3D printed with SMCs+ECs and, in some embodiments, the highest generation branches are 3D printed with MSCs+ECs because data indicated that these branches give rise to the microscopic vasculature (see, e.g., FIG. 26). In some embodiments, the DIW method provides a branching vascular structure with heterogeneous cellular composition. In some embodiments, the technology provides a perfuseable branching structure with at least two generations of branching that give rise to a microscopic vascular network (see, e.g., FIG. 26).

Some alternative embodiments comprise use of a sacrificial template method. For example, in some embodiments, a sacrificial substrate (e.g., comprising Pluronic F-127) is printed in the form of a branched macroscopic vascular structure on top of a fibrin gel slab. In some embodiments, an additional fibrin gel is cast on top of this structure to encapsulate it. Further, in some embodiments, hypodermic tubing is inserted into this structure. In some embodiments, the sacrificial substrate is liquefied, leaving a hollow channel network. In some embodiments, a vascular mural cell solution (e.g., comprising approximately $10\times10^6$ cells/ml) is instilled into the network. In some embodiments, the vascular network is placed on an incline to allow the bioink to flow into the most distal regions of the branched structure and to cause bubbles to escape.

In some embodiments, the domain (extent) of the perfused microscopic vascular network determines the size of the tissue construct, e.g., the larger the domain of the microscopic vascular network, the larger the tissue construct. Therefore, some embodiments of the technology comprise maximizing the domain of the perfused microscopic vascular network.

As indicated by data collected during experiments conducted and described herein, the MSC was the best VMC type that formed microscopic tubular sprouts. Further, data demonstrated that HIF1α stabilization increased the sprouting activity of MSCs in spherical organoids. These data indicated that the extent of the microscopic vascular network formation is regulated by HIF1α activity in MSCs. More specifically, these data indicated that stimulating HIF1α activity in MSCs increases the domain of the microscopic vascular network by: (1) increasing the length of mesoscopic and microscopic sprouting; and (2) increasing the frequency of microscopic tube fusion (anastomosis) to generate a complex mesh-like network.

Further, in some embodiments, the technology comprises use of sprouting mesoscopic linear channels made from MSCs or MSCs+ECs. In some embodiments, sprouting mesoscopic linear channels comprise MSCs or MSCs+ECs as a platform to measure HIF1α activity and the association of HIF1α with increased length of microscopic sprouts. In some embodiments, linear channels comprising MSCs are made either by a removable substrate method as described herein or by a DIW method as described herein. In some embodiments, HIF1α activity is stimulated by adding FG-4592 or by culturing under hypoxic (0.1% $O_2$) conditions for 1 to 10 days (e.g., 5 days, e.g., 1, 2, 3, 4, 5, 6, 7, 8, 9, or 10 days). In some embodiments, the length and density of sprouts is quantified using image analysis software. In some embodiments, FG-4592 and hypoxic conditions stimulate the length and density of microscopic sprouting from MSC based mesoscopic channels.

In *Drosophila*, Escargot (Esg), a zinc finger protein, is expressed in tracheal tip fusion cells and appears to drive gene expression specific for fusion cells. The mammalian homologue for Esg is SNAi2. SNAi2 has been shown to be important in EC angiogenesis and MSC invasion in collagen. Hypoxia has been shown to stimulate SNAi2 expression in human coronary artery ECs. Data also indicate in cancer stem cells that HIF1α stimulates the transcription of SNAi2. These data collectively indicate that MSC tube fusion is stimulated by a HIF1α-SNAi2 axis. See, e.g., Blum et al. (2008) "Complex cell rearrangements during intersegmental vessel sprouting and vessel fusion in the zebrafish embryo" *Dev Biol* 316: 312-322; Herwig. et al. (2011) "Distinct cellular mechanisms of blood vessel fusion in the zebrafish embryo" *Curr Biol*21: 1942-1948; Fantin et al. (2010) "Tissue macrophages act as cellular chaperones for vascular anastomosis downstream of VEGF-mediated endothelial tip cell induction" *Blood* 116: 829-840; Lenard et al. (2013) "In vivo analysis reveals a highly stereotypic morphogenetic pathway of vascular anastomosis" *Dev Cell* 25: 492-506; Miao & Hayashi) 2016) "Escargot controls the sequential specification of two tracheal tip cell types by suppressing FGF signaling in *Drosophila" Development* 143: 4261-4271; Yang et al. (2010) "Slug, mammalian homologue gene of *Drosophila* escargot, promotes neuronal-differentiation through suppression of HEB/daughterless" *Cell Cycle* 9: 2789-2802; Welch-Reardon et al. (2014) "Angiogenic sprouting is regulated by endothelial cell expression of Slug" *J Cell Sci* 127: 2017-2028; Lu et al. (2013) "Snail mediates PDGF-BB-induced invasion of rat bone marrow mesenchymal stem cells in 3D collagen and chick chorioallantoic membrane" *J Cell Physiol* 228: 1827-1833; Evrard et al. (2016) "Endothelial to mesenchymal transition is common in atherosclerotic lesions and is associated with plaque instability" *Nat Commun* 7: 11853; and D'Uva et al. (2013) "Beta-catenin/HuR post-transcriptional machinery governs cancer stem cell features in response to hypoxia" *PLoS One* 8: e80742.

Accordingly, in some embodiments, stimulation of HIF1α activity via FG-4592 or by hypoxic conditions leads to the upregulation of SNAi2 in MSCs (e.g., in monolayer and/or spherical organoid culture conditions).

As described herein, the technology provides a platform to produce engineered vascular networks, e.g., by fusion of microscopic networks comprising sprouting linear channels made of MSCs (or MSCs+ECs). Further, data were collected that indicated successful MSC tube fusion by perfusing fluorescent microspheres (5 μm diameter) into one channel (e.g., on one side of the capillary bed) and detecting fluorescence in the second channel (e.g., on the other side of the capillary bed). Similarly, in some embodiments experiments are conducted in which this platform finds use in studying the role of HIF1α and SNAi2 in tube fusion. For example, experiments establish that HIF1α stimulation with FG-4592 or hypoxia (0.1%) leads to an increase in tube fusion.

In some embodiments, the technology comprises a method to increase the domain of the microscopic vascular network. For example, in some embodiments the technology comprises adding additional MSCs to the region of fibrin gel. Data collected during experiments conducted during the development of embodiments of the technology described herein indicated that ECs do not readily self-organize into mesh like networks in fibrin gel. Data collected during experiments conducted during the development of embodiments of the technology described herein indicated that small spherical organoids comprising MSCs and MSCs+ ECs (e.g., as few as 20 total cells/organoid) readily sprout within fibrin gel. Confocal microscopy and histology data further suggested that many of the spherical organoids are hollow. Accordingly, in some embodiments, small spherical organoids serve as niduses for small sprouting networks that fuse with the sprouts emanating from the adjacent VMC-based vasculature structures and thus bridge the gap between the two structures.

In some embodiments, the technology comprises two linear vascular structures comprising MSCs (or MSCs+ECs) (e.g., made either by the removable substrate method or by DIW method) and separated by 1-20 mm (e.g., 1, 2, 3, 4, 5, 6, 7, 8, 9, 10, 11, 12, 13, 14, 15, 16, 17, 18, 19, or 20 mm). In some embodiments, spherical organoids are encapsulated in a fibrin gel between the linear vascular structures (e.g., to bridge the two linear vascular structures). In some embodiments, the organoids have a range of different spherical organoid densities. In some embodiments, the vascular structures are cultured for 3 to 10 days (e.g., 3, 4, 5, 6, 7, 8, 9, or 10 days). In some embodiments, fluorescent microspheres (5 μm diameter) are perfused into one of the channels (e.g., a first vascular structure anastomosed with a second vascular structure) and detected in the other channel (e.g., said second vascular structure anastomosed with said first vascular structure) to indicate fusion of the two vascular structures and formation of patent connections. Accordingly, related embodiments of the technology provide a microscopic vascular network domain of several square centimeters (e.g., at least 2 $cm^2$) in area.

Data collected during the development of embodiments of the technology described herein indicated that the technology provides a complete vascular network with engineered artery, capillaries, and vein that is perfusable for at least 14 days and, in some embodiments, up to more than 30 days (e.g., 10, 11, 12, 13, 14, 15, 16, 17, 18, 19, 20, 21, 22, 23, 24, 25, 26, 27, 28, 29, 30, 31, 32, 33, 34, 35, or more days). Accordingly, the technology further provides an engineered perfusable complete vascular network comprising an engineered artery, capillary network (e.g., comprising a domain of at least approximately 2 $cm^2$ (e.g., 1, 2, 3, 4, 5, 6, 7, 8, 9, 10 $cm^2$), and vein. In some embodiments, the perfusable complete vascular network functions as an engineered epicardium upon which cardiomyocytes are seeded, thereby producing and/or providing a vascularized engineered heart tissue (EHT). In some embodiments, cardiomyocytes are isolated from a mammal (e.g., neonatal rat hearts, a human, a patient) to test growth on the fibrin gel based engineered epicardium technology described herein. After generating a perfusable engineered epicardium, some embodiments comprise seeding cardiomyocytes (e.g., human, e.g., from a patient) at approximately 200,000 cells per 2 $cm^2$. In some embodiments, cells are labelled with fluorescent dyes, e.g., so that two-photon microscopy is used for imaging. In some embodiments, continuous and pulsatile perfusion of oxygenated EHT culture medium is performed for at least 14 days. Further, in some embodiments the mass transport function of the perfused vascular networks is measured. In particular, in some embodiments EHT viability is measured in normoxic and hypoxic conditions for 14 days while being perfused with media enriched with oxygen) and EHT beat frequency (e.g., as determined by video microscopy) is measured in response to perfusion of chronotropic agents through the engineered vasculature.

Accordingly, embodiments provide a vasculature for engineered tissues that is multiscalar and multiphenotype to distribute energy and mass flow to parenchymal cells. In some embodiments, the engineered vascular network comprises a perfused artery, capillaries, and a draining vein. In some embodiments, complexity of the vasculature is present at multiple scales: e.g., a branching and patent structure is present at the macroscopic (>500 μm diameter) and mesoscopic (100-500 μm) scale and a mesh-like tubular network structure is present at the microscopic scale (5-20 μm). In some embodiments, the walls of the macroscopic and mesoscopic vessels are multilayered and comprise different cell types. In some embodiments, the microscopic capillaries are a single layer thick and comprise, in some embodiments, vascular mural cell (VMC) coverage. In some embodiments, the artery and vein are sufficiently large and biomechanically robust to anastomose to a patient's vasculature. In some embodiments, the capillary network is sufficiently dense to provide mass transfer with adjacent parenchymal cells (e.g., each cardiomyocyte is surrounded by a capillary in the native heart) and occupies a sufficiently large domain to support the entire engineered tissue construct. In some embodiments, engineered vascular networks are perfused to permit in vitro scale-up of engineered tissues.

Example 15—Measurement of Biomechanical Properties of Engineered Vessels

During the development of embodiments of the technology described herein, experiments were conducted to test the tensile modulus (e.g., under pressure) of vascular structures described herein. In particular, MSC-based vascular structures are produced according do embodiments of the technology described herein. Next, a second parallel channel is created in the fibrin (e.g., 2 mm away from the MSC-based vascular structure) but does not comprise cells. After 7 days of culture, the structures are tested. In the test, MSC-based vascular structures and non-cell-seeded channels are primed with media and the inlet port is connected to pressure tubing. The outlet port is capped and the MSC-based vascular structure and non-cell-seeded channels are subjected to pressurization by elevating a column of media connected to the inlet port and tubing. An inline pressure transducer is used to measure pressure within the fluid filled circuits. Pressurization is performed at 0-10 mmHg above atmosphere in 1 mmHg increments.

Using an inverted brightfield microscope (40× magnification), digital images of the central 5 mm of the vascular structure and non-cell-seeded channels are taken after 1 minute of equilibration at each pressure. From these digital images taken at each pressure, the inner and outer diameters of the MSC-based vascular structure and the diameter of the non-cell-seeded channel are measured. These measurements are taken at each pressure increment and the average of the imaged MSC-based vascular structure/channel is calculated.

Figure 27:
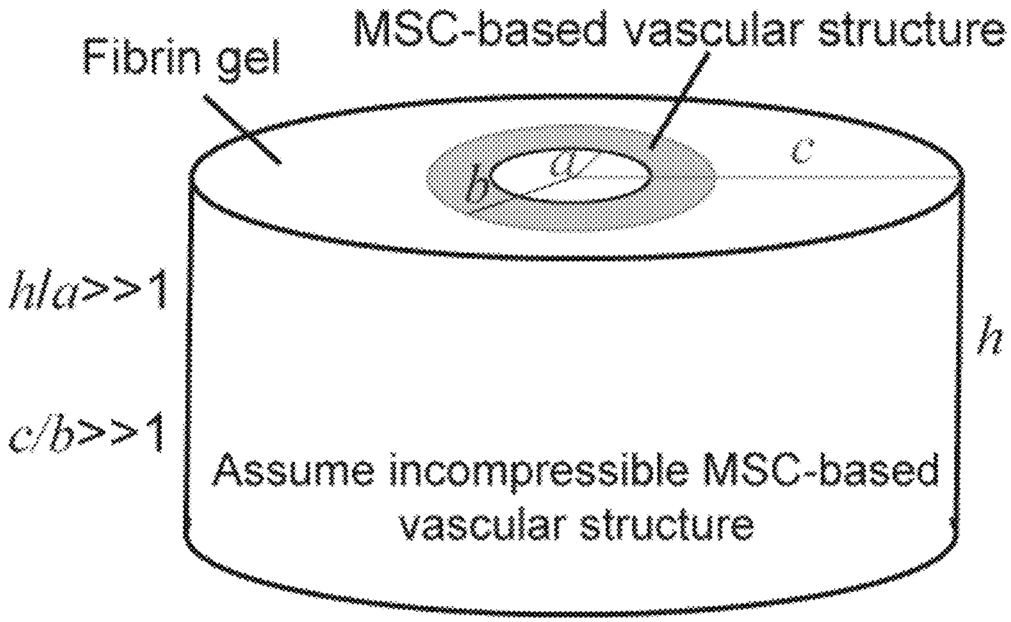
FIG. 27 is a drawing showing the model used to calculate tensile modulus of fibrin gel and MSC-based vascular structure (e.g., according to Equation 1 and Equation 2 infra).

In the experiment, the MSC-based vascular structure is modeled as a cylinder within a larger cylinder (e.g., fibrin gel) (FIG. 27). Accordingly, two fundamental equations allow calculation of the tensile modulus of fibrin gel (E) and tensile modulus of the MSC-based vascular structure (E).

$$\bar{P} = \left(\frac{2\hat{E}}{3}\right)\left(\frac{\mu_R(b)}{b}\right) \quad \text{(Equation 1)}$$

$$\mu_R(a) = \frac{a}{b^2 - a^2}\left(\frac{3b^2}{2E}\right)\left[1 - \left(\frac{2a^2}{\left(\frac{3E}{2\hat{E}}\right)(b^2 - a^2) + 2a^2}\right)\right]P_i \quad \text{(Equation 2)}$$

Equation 1 relates to pressurization of the non-cell-seeded channel, where $\bar{P}$ is the pressure and $\mu_R(b)$ is the change in radius (b) from a resting state. Equation 2 relates to the MSC-based vascular structure, where $P_i$ is the pressure, a is the inner radius, b is the outer radius, $\mu_R$ (a) is the difference in inner radius from a resting state, $\hat{E}$ is tensile modulus solved from the first equation, and Eis the tensile modulus of the MSC-based vascular structure. In some embodiments, Mathematica (Wolfram Alpha) is used to perform these calculations.

After pressure testing, constructs are assessed for fibronectin FN, collagen (type I, III and IV), and LOX expression, e.g., using qPCR.

During the development of embodiments of the technology provided herein, data were collected from measurements of three 7-day old vascular structures (e.g., comprising ntMSC+HUVECs). Calculated values included an E value of 160,570±56,394 Pa (mean±SD), which is similar to the value for native tissues (see, e.g., Akhtar et al. (2011) "Characterizing the elastic properties of tissues" *Mater Today* (Kidlington) 14: 96-105). Based on these values, 15 samples per experimental group allow detecting a difference of 25% between the experimental and control groups with a statistical power of 85% using a two-tailed student's t test. Gene expression values is averaged and compared with either the student's t test or one way ANOVA. It is contemplated that vascular structures made with MSCs having a higher SLIT3 expression demonstrate increased extracellular matrix and LOX expression and increased E while decreasing MSC SLIT3 expression decreases extracellular matrix and LOX expression and makes vascular structures less stiff.

REFERENCES

1 Bae, H. et al. Building vascular networks. Sci Transl Med 4, 160 ps123, doi:10.1126/scitranslmed.3003688 (2012).

2 Miller, J. S. et al. Rapid casting of patterned vascular networks for perfusable engineered three-dimensional tissues. Nat Mater 11, 768-774, doi:10.1038/nmat3357 (2012).

3 Bettex, D. A., Pretre, R. & Chassot, P. G. Is our heart a well-designed pump? The heart along animal evolution. Eur Heart J 35, 2322-2332, doi:10.1093/eurheartj/ehu222 (2014).

4 Monahan-Earley, R., Dvorak, A. M. & Aird, W. C. Evolutionary origins of the blood vascular system and endothelium. J Thromb Haemost 11 Suppl 1, 46-66, doi:10.1111/jth. 12253 (2013).

5 Bersini, S. et al. Cell-microenvironment interactions and architectures in microvascular systems. Biotechnol Adv, doi:10.1016/j.biotechadv.2016.07.002 (2016).

6 Laschke, M. W. & Menger, M. D. Prevascularization in tissue engineering: Current concepts and future directions. Biotechnol Adv 34, 112-121, doi:10.1016/j.biotechadv.2015.12.004 (2016).

7 Herbert, S. P. & Stainier, D. Y. Molecular control of endothelial cell behaviour during blood vessel morphogenesis. Nat Rev Mol Cell Biol 12, 551-564, doi:10.1038/nrm3176 (2011).

8 Wang, S., Mundada, L., Colomb, E., Ohye, R. G. & Si, M. S. Mesenchymal Stem/Stromal Cells from Discarded Neonatal Sternal Tissue: In Vitro Characterization and Angiogenic Properties. Stem Cells Int 2016, 5098747, doi:10.1155/2016/5098747 (2016).

9 Wang, S. et al. Characterization and angiogenic potential of human neonatal and infant thymus mesenchymal stromal cells. Stem Cells Transl Med 4, 339-350, doi: 10.5966/sctm.2014-0240 (2015).

10 Hofer, H. R. & Tuan, R. S. Secreted trophic factors of mesenchymal stem cells support neurovascular and musculoskeletal therapies. Stem Cell Res Ther 7, 131, doi: 10.1186/s13287-016-0394-0 (2016).

11 Ho, S. S., Murphy, K. C., Binder, B. Y., Vissers, C. B. & Leach, J. K. Increased Survival and Function of Mesenchymal Stem Cell Spheroids Entrapped in Instructive Alginate Hydrogels. Stem Cells Transl Med 5, 773-781, doi: 10.5966/sctm.2015-0211 (2016).

12 Lee, E. J. et al. Spherical bullet formation via E-cadherin promotes therapeutic potency of mesenchymal stem cells derived from human umbilical cord blood for myocardial infarction. Mol Ther 20, 1424-1433, doi: 10.1038/mt.2012.58 (2012).

13 De Smet, F., Segura, I., De Bock, K., Hohensinner, P. J. & Carmeliet, P. Mechanisms of vessel branching: filopodia on endothelial tip cells lead the way. Arterioscler Thromb Vasc Biol 29, 639-649, doi:10.1161/ATVBAHA.109.185165 (2009).

14 Eilken, H. M. & Adams, R. H. Dynamics of endothelial cell behavior in sprouting angiogenesis. Curr Opin Cell Biol 22, 617-625, doi:10.1016/j.ceb.2010.08.010 (2010).

15 Miguelino, M., Sahar, D. & Powell, J. Abstract 134: Adipose Derived Stem Cells Express von Willebrand Factor and Factor VIII. Plast Reconstr Surg 133, 150, doi:10.1097/01.prs.0000444961.82162.7f (2014).

16 Heydarkhan-Hagvall, S. et al. Human adipose stem cells: a potential cell source for cardiovascular tissue engineering. Cells Tissues Organs 187, 263-274, doi: 10.1159/000113407 (2008).

17 Shi, S. & Gronthos, S. Perivascular niche of postnatal mesenchymal stem cells in human bone marrow and dental pulp. J Bone Miner Res 18, 696-704, doi: 10.1359/jbmr.2003.18.4.696 (2003).

18 Gang, E. J. et al. In vitro endothelial potential of human UC blood-derived mesenchymal stem cells. Cytotherapy 8, 215-227, doi: 10.1080/14653240600735933 (2006).

19 Friis, T. et al. Comparison of mesenchymal stromal cells from young healthy donors and patients with severe chronic coronary artery disease. Scand J Clin Lab Invest 71, 193-202, doi:10.3109/00365513.2010.550310 (2011).

20 Ridley, A. J. Rho GTPase signalling in cell migration. Curr Opin Cell Biol 36, 103-112, doi:10.1016/j.ceb.2015.08.005 (2015).

21 Brinkmann, B. F. et al. VE-cadherin interacts with cell polarity protein Pals1 to regulate vascular lumen formation. Mol Biol Cell 27, 2811-2821, doi:10.1091/mbc.E16-02-0127 (2016).

22 Davis, G. E. & Camarillo, C. W. An alpha 2 beta 1 integrin-dependent pinocytic mechanism involving intracellular vacuole formation and coalescence regulates capillary lumen and tube formation in three-dimensional collagen matrix. Exp Cell Res 224, 39-51, doi:10.1006/excr.1996.0109 (1996).

23 Lampugnani, M. G. et al. CCM1 regulates vascular-lumen organization by inducing endothelial polarity. J Cell Sci 123, 1073-1080, doi:10.1242/jcs.059329 (2010).

24 Grikscheit, K. & Grosse, R. Formins at the Junction. Trends Biochem Sci 41, 148-159, doi:10.1016/j.tibs.2015.12.002 (2016).

25 Phng, L. K. et al. Formin-Mediated Actin Polymerization at Endothelial Junctions Is Required for Vessel Lumen Formation and Stabilization. Dev Cell 32, 123-132, doi:10.1016/j.devcel.2014.11.017 (2015).

26 Chaki, S. P. & Rivera, G. M. Integration of signaling and cytoskeletal remodeling by Nck in directional cell migration. Bioarchitecture 3, 57-63, doi:10.4161/bioa.25744 (2013).

27 Tung, J. J., Tattersall, I. W. & Kitajewski, J. Tips, stalks, tubes: notch-mediated cell fate determination and mechanisms of tubulogenesis during angiogenesis. Cold Spring Harb Perspect Med 2, a006601, doi:10.1101/cshperspect.a006601 (2012).

28 Koo, Y. et al. Rasip1 is essential to blood vessel stability and angiogenic blood vessel growth. Angiogenesis 19, 173-190, doi:10.1007/s10456-016-9498-5 (2016).

29 del Toro, R. et al. Identification and functional analysis of endothelial tip cell-enriched genes. Blood 116, 4025-4033, doi:10.1182/blood-2010-02-270819 (2010).

30 Nehls, V., Denzer, K. & Drenckhahn, D. Pericyte involvement in capillary sprouting during angiogenesis in situ. Cell Tissue Res 270, 469-474 (1992).

31 Ozerdem, U. & Stallcup, W. B. Early contribution of pericytes to angiogenic sprouting and tube formation. Angiogenesis 6, 241-249, doi:10.1023/B:AGEN.0000021401.58039.a9 (2003).

32 Wagenblast, E. et al. A model of breast cancer heterogeneity reveals vascular mimicry as a driver of metastasis. Nature 520, 358-+, doi: 10.1038/nature14403 (2015).

33 Demou, Z. N. & Hendrix, M. J. Microgenomics profile the endogenous angiogenic phenotype in subpopulations of aggressive melanoma. J Cell Biochem 105, 562-573, doi:10.1002/jcb.21855 (2008).

34 Mazzone, M. et al. Heterozygous deficiency of PHD2 restores tumor oxygenation and inhibits metastasis via endothelial normalization. Cell 136, 839-851, doi:10.1016/j.cell.2009.01.020 (2009).

35 Phng, L. K. et al. Formin-mediated actin polymerization at endothelial junctions is required for vessel lumen formation and stabilization. Dev Cell 32, 123-132, doi:10.1016/j.devcel.2014.11.017 (2015).

36 Rizvi, S. A. et al. Identification and characterization of a small molecule inhibitor of formin-mediated actin assembly. Chem Biol 16, 1158-1168, doi:10.1016/j.chembiol.2009.10.006 (2009).

37 Grant, D. S., Kleinman, H. K. & Martin, G. R. The role of basement membranes in vascular development. Ann N Y Acad Sci 588, 61-72 (1990).

38 Grant, D. S. & Kleinman, H. K. Regulation of capillary formation by laminin and other components of the extracellular matrix. EXS 79, 317-333 (1997).

39 Siemerink, M. J. et al. CD34 marks angiogenic tip cells in human vascular endothelial cell cultures. Angiogenesis 15, 151-163, doi:10.1007/s10456-011-9251-z (2012).

40 Hendrix, M. J. et al. Tumor cell vascular mimicry: Novel targeting opportunity in melanoma. Pharmacol Ther 159, 83-92, doi:10.1016/j.pharmthera.2016.01.006 (2016).

41 Maniotis, A. J. et al. Vascular channel formation by human melanoma cells in vivo and in vitro: vasculogenic mimicry. Am J Pathol 155, 739-752, doi:10.1016/S0002-9440(10)65173-5 (1999).

42 Caplan, A. I. & Hariri, R. Body Management: Mesenchymal Stem Cells Control the Internal Regenerator. Stem Cells Transl Med 4, 695-701, doi:10.5966/sctm.2014-0291 (2015).

43 Gokcinar-Yagci, B., Uckan-Cetinkaya, D. & Celebi-Saltik, B. Pericytes: Properties, Functions and Applications in Tissue Engineering. Stem Cell Rev 11, 549-559, doi:10.1007/s12015-015-9590-z (2015).

44 Horowitz, A. & Simons, M. Branching morphogenesis. Circ Res 103, 784-795, doi:10.1161/CIRCRESAHA.108.181818 (2008).

45 Ghabrial, A. S. & Krasnow, M. A. Social interactions among epithelial cells during tracheal branching morphogenesis. Nature 441, 746-749, doi:10.1038/nature04829 (2006).

47 Zotin A I, Zotina R S. Thermodynamic aspects of developmental biology. J Theor Biol. 1967; 17:57-75.

48 Simons M, Eichmann A. Molecular controls of arterial morphogenesis. Circ Res. 2015; 116:1712-1724.

49 Crisan M, Yap S, Casteilla L et al. A perivascular origin for mesenchymal stem cells in multiple human organs. Cell Stem Cell. 2008; 3:301-313.

50 Alexander M R, Owens G K. Epigenetic control of smooth muscle cell differentiation and phenotypic switching in vascular development and disease. Annu Rev Physiol. 2012; 74:13-40.

51 Melchiorri A J, Nguyen B N, Fisher J P. Mesenchymal stem cells: roles and relationships in vascularization. Tissue Eng Part B Rev. 2014; 20:218-228.

52 Skoog S A, Goering P L, Narayan R J. Stereolithography in tissue engineering. J Mater Sci Mater Med. 2014; 25:845-856.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A system for producing a perfusable engineered vasculature, the system comprising: a three-dimensional fibrin gel comprising a hollow channel formed within the fibrin gel, wherein the fibrin gel does not comprise cells within the fibrin gel itself, and a mixture of endothelial cells (ECs) and mesenchymal stem cells (MSCs) placed within the hollow channel of the fibrin gel, wherein the mixture of ECs and MSCs comprises approximately 10-100 million cells per cubic centimeter.

2. The system of claim 1, wherein the ECs are artery ECs or vein ECs.

3. The system of claim 1, wherein the MSCs are thymus MSCs.

4. The system of claim 1, further comprising an incubator.

5. The system of claim 1, further comprising a tissue chamber, wherein the tissue chamber is made from polydimethylsiloxane.

6. The system of claim 1, wherein the ratio of ECs to MSCs is 1 to 1.

7. The system of claim 1, wherein the MSCs are isolated from thymus, bone, adipose, or other tissue or cells.

8. The system of claim 4, wherein the incubator provides conditions of 37° C. and 5% $CO_2$.

9. The system of claim 1, wherein the ECs and MSCs are present at a density of at least 40 million cells per cubic centimeter.

10. The system of claim 1, wherein the hollow channel has a diameter greater than 1 mm.

11. The system of claim 1, further comprising a tissue chamber comprising an inlet port and an outlet port.

* * * * *